US006686188B2

(12) United States Patent
Gu et al.

(10) Patent No.: US 6,686,188 B2
(45) Date of Patent: Feb. 3, 2004

(54) POLYNUCLEOTIDE ENCODING A HUMAN MYOSIN-LIKE POLYPEPTIDE EXPRESSED PREDOMINANTLY IN HEART AND MUSCLE

(75) Inventors: Yizhong Gu, Sunnyvale, CA (US); Yonggang Ji, San Mateo, CA (US); Sharron Gaynor Penn, San Mateo, CA (US); David Kagen Hanzel, Palo Alto, CA (US); David Russell Rank, Fremont, CA (US); Wensheng Chen, Mountain View, CA (US); Mark E. Shannon, Livermore, CA (US)

(73) Assignee: Amersham PLC, Buckinghamshire (GB)

( * ) Notice: Subject to any disclaimer, the term of this patent is extended or adjusted under 35 U.S.C. 154(b) by 0 days.

(21) Appl. No.: 09/866,108

(22) Filed: May 25, 2001

(65) Prior Publication Data

US 2002/0048800 A1 Apr. 25, 2002

Related U.S. Application Data

(63) Continuation-in-part of application No. PCT/US01/00666, filed on Jan. 30, 2001, and a continuation-in-part of application No. PCT/US01/00667, filed on Jan. 30, 2001, and a continuation-in-part of application No. PCT/US01/00664, filed on Jan. 30, 2001, and a continuation-in-part of application No. PCT/US01/00669, filed on Jan. 30, 2001, and a continuation-in-part of application No. PCT/US01/00665, filed on Jan. 30, 2001, and a continuation-in-part of application No. PCT/US01/00668, filed on Jan. 30, 2001, and a continuation-in-part of application No. PCT/US01/00663, filed on Jan. 30, 2001, and a continuation-in-part of application No. PCT/US01/00662, filed on Jan. 30, 2001, and a continuation-in-part of application No. PCT/US01/00661, filed on Jan. 30, 2001, and a continuation-in-part of application No. PCT/US01/00670, filed on Jan. 30, 2001.
(60) Provisional application No. 60/207,456, filed on May 26, 2000, provisional application No. 60/234,687, filed on Sep. 21, 2000, provisional application No. 60/236,359, filed on Sep. 27, 2000, and provisional application No. 60/266,860, filed on Feb. 5, 2001.

(30) Foreign Application Priority Data

Oct. 4, 2000 (GB) .............................................. 0024263

(51) Int. Cl.[7] .......................... C12N 9/16; C12N 15/00; C12N 5/00; C07H 21/04
(52) U.S. Cl. ................. 435/196; 435/320.1; 435/287.2; 435/325; 435/419; 435/252.3; 435/254.11; 536/23.2; 536/23.5
(58) Field of Search ............................. 536/23.1, 23.2, 536/23.5, 24.31; 435/320.1, 196, 254.11, 325, 252.3, 287.2, 419; 514/44

(56) References Cited

U.S. PATENT DOCUMENTS

| 3,687,808 A | 8/1972 | Merigan, Jr. et al. |
| 3,980,986 A | 9/1976 | Baird et al. |
| 4,246,774 A | 1/1981 | Flesselles et al. |
| 4,469,863 A | 9/1984 | Ts'o et al. |
| 4,476,301 A | 10/1984 | Imbach et al. |
| 4,708,871 A | 11/1987 | Geysen |
| 5,023,243 A | 6/1991 | Tullis |
| 5,034,506 A | 7/1991 | Summerton et al. |
| 5,166,315 A | 11/1992 | Summerton et al. |
| 5,177,196 A | 1/1993 | Meyer, Jr. et al. |
| 5,185,444 A | 2/1993 | Summerton et al. |
| 5,186,042 A | 2/1993 | Miyazaki |
| 5,188,897 A | 2/1993 | Suhadolnik et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,071 A | 12/1993 | Chappel |
| 5,276,019 A | 1/1994 | Cohen et al. |
| 5,278,302 A | 1/1994 | Caruthers et al. |

(List continued on next page.)

FOREIGN PATENT DOCUMENTS

| WO | WO 84/03564 | 9/1984 |
| WO | WO 96/18412 | 6/1996 |
| WO | WO 96/32478 | 10/1996 |
| WO | WO 97/19193 | 5/1997 |
| WO | WO 97/34631 | 9/1997 |
| WO | WO 97/43316 | 11/1997 |
| WO | WO 98/12559 | 3/1998 |
| WO | WO 98/59360 | 12/1998 |
| WO | WO 98/59361 | 12/1998 |
| WO | WO 98/59362 | 12/1998 |
| WO | WO 99/58720 | 11/1999 |
| WO | WO 00/15779 | 3/2000 |
| WO | WO 00/26372 | 5/2000 |
| WO | WO 00/58473 | 10/2000 |
| WO | WO 00/77173 A1 | 12/2000 |
| WO | WO 01/57276 A1 | 8/2001 |

OTHER PUBLICATIONS

Seffernick et al. (2001) J Bacteriol 183:2405–2410.*

Lloyd, D., "Human DNA Sequence from Clone CTA–125H2 on Chromosome 22q11–12 Contains Part of the Gene for a Novel Protein Similar to KIAA0216 and Myosin Heavy Chain, ESTs, GSSs, and a CpG Island," *Database EMBL* (*Online*), Entry HS125H2, Accession No. Z98949 (Sep. 6, 1997).

(List continued on next page.)

Primary Examiner—Rebecca A. Prouty
Assistant Examiner—David J Steadman
(74) Attorney, Agent, or Firm—Fish & Neave; Daniel M. Becker; David A. Roise

(57) ABSTRACT

Presented are a novel myosin-like protein particularly expressed in human heart and muscle, isolated nucleic acids encoding the myosin-like protein, compounds and compositions derivable directly or indirectly therefrom, and diagnostic and therapeutic methods for using the same.

50 Claims, 19 Drawing Sheets

U.S. PATENT DOCUMENTS

| | | |
|---|---|---|
| 5,279,044 A | 1/1994 | Bremer |
| 5,286,717 A | 2/1994 | Cohen et al. |
| 5,321,131 A | 6/1994 | Agrawal et al. |
| 5,399,676 A | 3/1995 | Froehler |
| 5,405,938 A | 4/1995 | Summerton et al. |
| 5,405,939 A | 4/1995 | Suhadolnik et al. |
| 5,434,257 A | 7/1995 | Matteucci et al. |
| 5,445,934 A | 8/1995 | Fodor et al. |
| 5,453,496 A | 9/1995 | Caruthers et al. |
| 5,455,233 A | 10/1995 | Spielvogel et al. |
| 5,464,764 A | 11/1995 | Capecchi et al. |
| 5,466,677 A | 11/1995 | Baxter et al. |
| 5,470,967 A | 11/1995 | Huie et al. |
| 5,476,925 A | 12/1995 | Letsinger et al. |
| 5,487,992 A | 1/1996 | Capecchi et al. |
| 5,489,677 A | 2/1996 | Sanghvi et al. |
| 5,519,126 A | 5/1996 | Hecht |
| 5,527,695 A | 6/1996 | Hodges et al. |
| 5,536,821 A | 7/1996 | Agrawal et al. |
| 5,538,848 A | 7/1996 | Livak et al. |
| 5,539,082 A | 7/1996 | Nielsen et al. |
| 5,541,306 A | 7/1996 | Agrawal et al. |
| 5,541,307 A | 7/1996 | Cook et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,569,825 A | 10/1996 | Lonberg et al. |
| 5,570,694 A | 11/1996 | Rometsch |
| 5,571,799 A | 11/1996 | Tkachuk et al. |
| 5,587,361 A | 12/1996 | Cook et al. |
| 5,589,466 A | 12/1996 | Felgner et al. |
| 5,591,669 A | 1/1997 | Krimpenfort et al. |
| 5,595,915 A | 1/1997 | Geysen |
| 5,596,086 A | 1/1997 | Matteucci et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,396 A | 3/1997 | Bradley et al. |
| 5,618,704 A | 4/1997 | Sanghvi et al. |
| 5,623,070 A | 4/1997 | Cook et al. |
| 5,625,048 A | 4/1997 | Tsien et al. |
| 5,625,050 A | 4/1997 | Beaton et al. |
| 5,625,126 A | 4/1997 | Lonberg et al. |
| 5,627,052 A | 5/1997 | Schrader |
| 5,627,059 A | 5/1997 | Capecchi et al. |
| 5,631,153 A | 5/1997 | Capecchi et al. |
| 5,633,360 A | 5/1997 | Bischofberger et al. |
| 5,633,425 A | 5/1997 | Lonberg et al. |
| 5,661,016 A | 8/1997 | Lonberg et al. |
| 5,663,312 A | 9/1997 | Chaturvedula |
| 5,677,437 A | 10/1997 | Teng et al. |
| 5,677,439 A | 10/1997 | Weis et al. |
| 5,679,647 A | 10/1997 | Carson et al. |
| 5,693,761 A | 12/1997 | Queen et al. |
| 5,714,320 A | 2/1998 | Kool |
| 5,714,331 A | 2/1998 | Buchardt et al. |
| 5,719,262 A | 2/1998 | Buchardt et al. |
| 5,723,591 A | 3/1998 | Livak et al. |
| 5,731,181 A | 3/1998 | Kmiec |
| 5,741,668 A | 4/1998 | Ward et al. |
| 5,744,305 A | 4/1998 | Fodor et al. |
| 5,756,325 A | 5/1998 | Kmiec |
| 5,760,012 A | 6/1998 | Kmiec et al. |
| 5,766,886 A | 6/1998 | Studnicka et al. |
| 5,770,196 A | 6/1998 | Studnicka |
| 5,770,429 A | 6/1998 | Lonberg et al. |
| 5,777,079 A | 7/1998 | Tsien et al. |
| 5,780,296 A | 7/1998 | Holloman et al. |
| 5,789,650 A | 8/1998 | Lonberg et al. |
| 5,795,972 A | 8/1998 | Kmiec |
| 5,804,387 A | 9/1998 | Cormack et al. |
| 5,804,566 A | 9/1998 | Carson et al. |
| 5,807,715 A | 9/1998 | Morrison et al. |
| 5,814,318 A | 9/1998 | Lonberg et al. |
| 5,821,123 A | 10/1998 | Studnicka |
| 5,821,337 A | 10/1998 | Carter et al. |
| 5,824,269 A | 10/1998 | Kosaka et al. |
| 5,830,877 A | 11/1998 | Carson et al. |
| 5,843,913 A | 12/1998 | Li et al. |
| 5,846,726 A | 12/1998 | Nadeau et al. |
| 5,854,033 A | 12/1998 | Lizardi |
| 5,869,619 A | 2/1999 | Studnicka |
| 5,871,984 A | 2/1999 | Kmiec |
| 5,874,299 A | 2/1999 | Lonberg et al. |
| 5,874,304 A | 2/1999 | Zolotukhin et al. |
| 5,877,397 A | 3/1999 | Lonberg et al. |
| 5,880,104 A | 3/1999 | Li et al. |
| 5,888,983 A | 3/1999 | Kmiec et al. |
| 5,889,351 A | 3/1999 | Okumura et al. |
| 5,925,517 A | 7/1999 | Tyagi et al. |
| 5,930,143 A | 7/1999 | Savazzi |
| 5,939,598 A | 8/1999 | Kucherlapati et al. |
| 5,945,339 A | 8/1999 | Holloman et al. |
| 5,958,891 A | 9/1999 | Hsu et al. |
| 5,968,750 A | 10/1999 | Zolotukhin et al. |
| 5,981,214 A | 11/1999 | Skoultchi |
| 5,984,175 A | 11/1999 | Popp |
| 5,985,847 A | 11/1999 | Carson et al. |
| 5,990,689 A | 11/1999 | Poncon |
| 6,001,233 A | 12/1999 | Levy |
| 6,001,593 A | 12/1999 | Bandman et al. |
| 6,004,744 A | 12/1999 | Goelet et al. |
| 6,004,752 A | 12/1999 | Loewy et al. |
| 6,013,256 A | 1/2000 | Light et al. |
| 6,017,897 A | 1/2000 | Li et al. |
| 6,025,201 A | 2/2000 | Zelmanovic et al. |
| 6,027,881 A | 2/2000 | Pavlakis et al. |
| 6,046,800 A | 4/2000 | Ohtomo et al. |
| 6,048,524 A | 4/2000 | Selden et al. |
| 6,051,831 A | 4/2000 | Köster |
| 6,054,297 A | 4/2000 | Carter et al. |
| 6,054,321 A | 4/2000 | Tsien et al. |
| 6,063,630 A | 5/2000 | Treco et al. |
| 6,066,476 A | 5/2000 | Tsien et al. |
| 6,075,181 A | 6/2000 | Kucherlapati et al. |
| 6,090,919 A | 7/2000 | Cormack et al. |
| 6,096,548 A | 8/2000 | Stemmer |
| 6,096,865 A | 8/2000 | Michaels |
| 6,110,898 A | 8/2000 | Malone et al. |
| 6,114,598 A | 9/2000 | Kucherlapati et al. |
| 6,117,679 A | 9/2000 | Stemmer |
| 6,124,128 A | 9/2000 | Tsien et al. |
| 6,150,584 A | 11/2000 | Kucherlapati et al. |
| 6,162,963 A | 12/2000 | Kucherlapati et al. |
| 6,165,793 A | 12/2000 | Stemmer |
| 6,180,370 B1 | 1/2001 | Queen et al. |
| 6,180,377 B1 | 1/2001 | Morgan et al. |
| 6,180,406 B1 | 1/2001 | Stemmer |
| 6,187,305 B1 | 2/2001 | Treco et al. |
| 6,204,061 B1 | 3/2001 | Capecchi et al. |
| 6,204,250 B1 | 3/2001 | Bot et al. |

OTHER PUBLICATIONS

Lloyd, D., "BK125H2.1 (Novel Protein Similar to KIAA0216 and Myosin Heavy Chain) (Fragment)" *Database SWISSPROT* (Online), Entry/Acc. No. 060772 (Aug. 1, 1998).

Waye et al., "Hk594–f Adult Heart, Clontech *Homo Sapiens* cDNA Clone K594–f, mRNA," *Database EMBL (Online)*, Entry HS006124, Acc. No. R41006 (May 4, 2000).

Yokota et al., "*Homo Sapiens* bk125h2.1 mRNA, Complete CDs," *Database EMBL (Online)*, Entry/Acc. No. AB042648 (May 16, 2001).

Alers et al., "Universal Linkage System: An Improved Method for Labeling Archival DNA for Comparative Genomic Hybridization," *Genes, Chromosomes & Cancer*, vol. 25: pp. 301–305 (1999).

Bahler et al., "Are Class III and Class IX Myosins Motorized Signalling Molecules?" *Biochimica et Biophysica Acta 1496*:pp. 52–59 (2000).

Baker et al., "A Family of Unconventional Myosins from the Nematode *Caenorhabditis elegans*," *J. Mol. Biol.* vol. 272: pp. 523–535 (1997).

Baker et al., "Myosins: Matching Functions with Motors," *Current Opinion Cell Biology* vol. 10: pp. 80–86 (1998).

Banér et al., "More Keys to Padlock Probes: Mechanisms for High–Throughput Nucleic Acid Analysis," *Current Opinion in Biotechnology* vol. 12:pp. 11–15 (2001).

Bauer et al., "Human CLP36, a PDZ–Domain and LIM–Domain Protein, Binds to α–Actinin–1 and Associates with Actin Filaments and Stress Fibers in Activated Platelets and Endothelial Cells," *Blood* vol. 96 No. 13: pp. 4236–4245 (Dec. 15, 2000).

Brenner et al., "In Vitro Cloning of Complex Mixtures of DNA on Microbeads: Physical Separation of Differentially Expressed cDNAs," *Proc. Natl. Acad. Sci. USA* vol. 97 No. 4: pp. 1665–1670 (2000).

Brown, Susan S., "Myosins in Yeast," *Current Opinion in Cell Biology* vol. 9: pp. 44–48 (1997).

Chan et al., "Triplex DNA: Fundamentals, Advances, and Potential Applications for Gene Therapy," *J. Mol. Med.* vol. 75: pp. 267–282 (1997).

Clontech, *Retroviral Gene Transfer and Expression User Manual:* Jan. 11, 2001.

Culver et al., Correction of Chromosomal Point Mutations in Human Cells with Bifunctional Oligonucleotides, *Nature Biotechnology* vol. 17: pp. 989–993 (1999).

Escude et al., "Padlock Oligonucleotides for Duplex DNA Based on Sequence–Specific Triple Helix Formation," *Proc. Natl. Acad. Sci. USA* vol. 96: pp. 10603–10607 (1999).

Espreafico et al., "Primary Structure and Cellular Localization of Chicken Brain Myosin–V (p190), an Unconventional Myosin with Calmodulin Light Chains," *Journal of Cell Biology* vol. 119 No. 6: pp. 1541–1557 (Dec. 1992).

Finn et al., "Synthesis and Properties of DNA–PNA Chimeric Oligomers," *Nucleic Acids Research* vol. 24 No. 17: pp. 3357–3363 (1996).

Fox, Keith R., "Targeting DNA with Triplexes," *Current Medicinal Chemistry* vol. 7: pp. 17–37 (2000).

Furusawa et al., "Isolation of a Novel PDZ–Containing Myosin from Hematopoietic Supportive Bone Marrow Stromal Cell Lines," *Biochemical and Biophysical Research Communications* vol. 270: pp. 67–75 (2000).

Gamper et al., "The DNA Strand of Chimeric RNA/DNA Oligonecleotides Can Direct Gene Repair/Conversion Activity in Mammalian and Plant Cell–Free Extracts," *Nucleic Acids Research* vol. 28 No. 21:pp. 4332–4339 (2000).

Gautheret et al., "Alternate Polyadenylation in Human mRNAs: A Large–Scale Analysis by EST Clustering," *Genome Research* vol. 8: pp. 524–530 (1998).

Gee et al., "Single–Amino Acid Substitutions Alter the Specificity and Affinity of PDZ Domains for Their Legends," *Biochemistry* vol. 39: pp. 14638–14646 (2000).

Geysen et al., Use of Peptide Synthesis to Probe Viral Antigens for Epitopes to a Resolution of a Single Amino Acid, *Proc. Natl. Acad. Sci. USA* vol. 81: pp. 3998–4002 (Jul. 1984).

Gonnet et al., "Exhaustive Matching of the Entire Protein Sequence Database," *Science* vol. 256: pp. 1443–1445 (Jun. 5, 1992).

Harrington et al., "Formation of de novo Centromeres and Construction of First–Generation Human Artificial Microchromosomes," *Nature Genetics* vol. 15: pp. 345–355 (1997).

Hasson, Tama, "Unconventional Myosins, the Basis for Deafness in Mouse and Man," *Am. J. Hum. Genet.* vol. 61: pp. 801–805 (1997).

Heid et al., "Real Time Quantitative PCR," *Genome Research* vol. 6 No. 10: pp. 986–994 (1996).

Henegariu et al., "Custom Fluorescent–Nucleotide Synthesis as an Alternative Method for Nucleic Acid Labeling," *Nature Biotechnology* vol. 18: pp. 345–348 (Mar. 2000).

Henning et al., "Human Artificial Chromosomes Generated by Modification of a Yeast Artificial Chromosome Containing Both Human Alpha Satellite and Single–Copy DNA Sequences," *Proc. Natl. Acad. Sci. USA* vol. 96: pp. 592–597 (1999).

Holland et al., "Detection of Specific Polymerase Chain reaction Product by Utilizing the 5'→3' Exonuclease Activity of *Thermus Aquaticus* DNA Polymerase," *Proc. Natl. Acad. Sci. USA* vol. 88: pp. 7276–7280 (1991).

International Human Genome Sequencing Consortium, "Initial Sequencing and Analysis of the Human Genome," *Nature* vol. 409: pp. 860–921 (Feb. 15, 2001).

Jelsma et al., "Increase Labeling of DNA Probes for In Situ Hybridization with the Universal Linkage Systems (ULS)," *Journal of NIH Research* vol. 5: p. 82 (1994).

Kelley et al., "Mutation of MYH9, Encoding Non–Muscle Myosin Heavy Chain A, in May–Hegglin Anomaly," *Nature Genetics* vol. 26:106–108 (Sep. 2000).

Kochetkoca et al., "Triplex–Forming Oligonucleotides and Their Use in the Analysis of Gene Transcription," *Methods in Molecular Biology* vol. 130: pp. 189–201 (2000).

Kostrikis et al., "Spectral Genotyping of Human Alleles," *Science* vol. 279: pp. 1228–1229 (1998).

Kuimelis et al., "Structural Analogues of TaqMan Probes for Real–Time Quantitative PCR," *Nucleic Acids Symposium Series* No. 37: pp. 255–256 (1997).

Kuroiwa et al., "Manipulation of Human Minichromosomes to Carry Greater than Megabase–Sized Chromosome Inserts," *Nature Biotechnology* vol. 18: pp. 1086–1090 (Oct. 2000).

Lalwani et al., "Human Nonsyndromic Hereditary Deafness DFNA17 Is Due to a Mutation in Nonmuscle Myosin MYH9," *Am. J. Hum. Genet.* vol. 67: pp. 1121–1128 (2000).

Lander et al., "The Chipping Forecast," *Supplement to Nature Genetics* vol. 21 No. 1: pp. 1–60 (Jan. 1999).

Larsen et al., "Antisense Properties of Peptide Nucleic Acid," *Biochimica et Biophysica Acta* vol. 1489: pp. 159–166 (1999).

Lerner, "Tapping the immunological repertoire to produce antibodies of predetermined specificity," *Nature* vol. 299: pp. 592–596 (1982).

Lizardi et al., "Mutation Detection and Single–Molecule Counting Using Isothermal Rolling–Circle Amplification," *Nature Genetics* vol. 19: pp. 225–232 (1998).

Marras et al., "Multiplex Detection of Single–Nucleotide Variations Using Molecular Beacons," *Genetic Analysis: Biomolecular Engineering* vol. 14: pp. 151–156 (1999).

Misra et al., "Polyamide Nucleic Acid–DNA Chimera Lacking the Phosphate Backbone Arc Novel Primers for Polymerase Reaction Catalyzed by DNA Polymerases," *Biochemistry* vol. 37: pp. 1917–1925 (1998).

Nagase et al., "Predicting of the Coding Sequences of Unidentified Human Genes, VI. The Coding Sequences of 80 New Genes (KIAA0201–KIAA0280) Deduced by Analysis of cDNA Clones from Cell Line KG–1 and Brain," *DNA Research* vol. 3: pp. 321–329 (1996).

Nielsen, "Peptide Nucleic Acids as Therapeutic Agents," *Current Opinion in Structural Biology* vol. 9: pp. 353–357 (1999).

Nielsen et al., "Peptide Nucleid Acids: On the Road to New Gene Therapeutic Drugs," *Pharmacology & Toxicology* vol. 86: pp. 3–7 (2000).

Nielsen, "Applications of Peptide Nucleic Acids," *Current Opinion in Biotechnology* vol. 10: pp. 71–75 (1999).

Nilsson et al., "Padlock Probes: Cirularizing Oligonucleotides for Localized DNA Detection," *Science* vol. 265 No. 5181: pp. 2085–2088 (1994).

Praseuth et al., "Triple Helix Formation and the Antigene Strategy for Sequence–Specific Control of Gene Expression," *Biochimica et Biophysica Acta 1489:* pp. 181–206 (1999).

Ray et al., "Peptide Nucleic Acid (PNA): Its Medical and Biotechnical Applications and Promise for the Future," *The FASEB Journal* vol. 14: pp. 1041–1060 (Jun. 2000).

Redowicz, Maria J., "Myosins and Deafness," *Journal of Muscle Research & Cell Motility* vol. 20: pp. 241–248 (1999).

Schoner et al., "Translation of a Synthetic Two–Cistron mRNA in *Escherichia coli,*" *Proc. Natl. Acad. Sci. USA* vol. 83: pp. 8506–8510 (1986).

Schweitzer et al., "Combining Nucleic Acid Amplification and Detection," *Current Opinion in Biotechnology* vol. 12: pp. 21–27 (2001).

Sellers, James R., "Myosins: A Diverse Superfamily," *Biochimica et Biophysica Acta* 1496: pp. 3–22 (2000).

Shinnick et al., "Synthetic Peptide Immunogens as Vaccines," *Annual Review of Microbiology* vol. 37: pp. 425–446 (1983).

Shizuya et al., "The Development and Applications of the Bacterial Artificial Chromosome cloning System," *Keio J. Med.* vol. 50: pp. 26–30 (2001).

Shizuya et al., "Cloning and Stable Maintenance of 300–Kilobase–Pair Fragments of Human DNA in *Escherichia Coli* Using an F–Factor–Based Vector," *Proc. Natl. Acad. Sci. USA* vol. 89: pp. 8794–8797 (1992).

Sokol et al., "Real Time Detection of DNA–RNA Hybridization in Living Cells," *Proc. Natl. Acad. Sci. USA* vol. 95: pp. 11538–11543 (1998).

Sutcliffe et al., "Antibodies that react with predetermined sites on proteins," *Science* vol. 219: pp. 660–666 (1983).

Tatusova et al., "Blast 2 sequences—a new tool for comparing protein and nucleotides sequences," *FEMS Microbiology Letters* vol. 174: pp. 247–250 (1999).

Tyagi et al., "Molecular Beacons: Probes that Fluoresce upon Hybridization," *Nature Biotechnology* vol. 14: pp. 303–308 (1996).

Tyagi et al., "Multicolor Molecular Beacons for Allele Discrimination," *Nature Biotechnology* vol. 16: pp. 49–53 (1998).

Van Belkum et al., "Non–Isotopic Labeling of DNA by Newly Developed Hapten–Containing Platinum Compounds," *BioTechniques* vol. 16 No. 1: pp. 148–153 (1994).

\* cited by examiner cDNA: 1 - 8117 [SEQ ID NO:1]
CDS: 170 - 7876 [SEQ ID NO:2]
AA: [SEQ ID NO:3]

```
cacccggggagacgtcttagacagtcgtggttcctgtgatctgtgtcctctt     52 tgcagaagttctgtgtccatctcatgtgctgcgtgtgtctgtaaagcctcat    104 tccgtgctgtctggcaggaagctccatctcatctcatcatctcacggccctg    156

M   A   I   S   S   R   L   A   L      9
gcactgcctcagc ATG GCC ATC TCA TCA CGC CTC GCC CTG          196

W   E   Q   K   I   R   E   E   D   K   S   P   P       22
 TGG GAG CAG AAG ATT CGG GAA GAG GAC AAG AGC CCT CCA       235

P   S   S   P   P   P   L   F   S   V   I   P   G       35
 CCA TCC TCG CCC CCT CCT CTT TTC TCT GTC ATC CCA GGG       274

G   F   I   K   Q   L   V   R   G   T   E   K   E       48
 GGC TTC ATT AAG CAA CTG GTC CGG GGG ACT GAA AAA GAG       313

A   K   E   A   R   Q   R   K   Q   L   A   V   A       61
 GCC AAG GAA GCG AGA CAG AGG AAG CAG TTA GCT GTC GCC       352

S   P   E   R   E   I   P   E   I   S   I   S   Q       74
 TCT CCA GAA CGA GAG ATC CCA GAA ATT TCC ATC AGC CAA       391

P   N   S   K   S   S   S   G   T   R   S   G   S       87
 CCC AAC AGC AAG TCC AGC AGT GGC ACC AGA TCT GGA AGC       430

Q   Q   I   S   Q   D   D   Q   S   S   S   P   G      100
 CAG CAG ATC TCT CAG GAC GAC CAG TCA AGC TCT CCT GGG       469

S   S   D   I   L   G   K   E   S   E   G   S   R      113
 AGC TCA GAC ATT CTG GGC AAG GAG AGC GAG GGG TCC CGC       508

S   P   D   P   E   Q   M   T   S   I   N   G   E      126
 AGC CCC GAC CCT GAG CAG ATG ACA AGC ATC AAT GGT GAG       547

K   A   Q   E   L   G   S   S   A   T   P   T   K      139
 AAG GCC CAG GAG CTG GGC TCC AGT GCG ACA CCA ACC AAA       586

K   T   V   P   F   K   R   G   V   R   R   G   D      152
 AAG ACT GTC CCC TTC AAG AGG GGC GTG AGG AGG GGT GAT       625

V   L   L   M   V   A   K   L   D   P   D   S   A      165
 GTG TTG TTG ATG GTG GCC AAG CTG GAC CCG GAC TCA GCC       664

```
              AAG CCA GAG AAG ACT CAT CCC CAT GAC GCC CCC CCT TGC   703
               K   T   S   P   P   A   T   D   T   G   K   E   K   191
              AAG ACC TCT CCC CCC GCC ACA GAT ACT GGA AAG GAA AAG   742
               K   G   E   T   S   R   T   P   C   G   S   Q   A   204
              AAA GGG GAG ACC TCT AGG ACT CCT TGT GGC TCC CAG GCC   781
               S   T   E   I   L   A   P   K   A   E   K   T   R   217
              AGC ACC GAG ATC TTG GCC CCG AAA GCT GAG AAG ACC CGG   820
               T   G   G   L   G   D   P   G   Q   G   T   V   A   230
              ACT GGG GGT CTT GGG GAC CCA GGC CAA GGA ACT GTG GCA   859
               L   K   K   G   E   E   G   Q   S   I   V   G   K   243
              CTG AAA AAA GGC GAG GAG GGT CAA AGC ATA GTG GGG AAG   898
               G   L   G   T   P   K   T   T   E   L   K   E   A   256
              GGG CTT GGG ACC CCC AAG ACC ACA GAG CTG AAA GAG GCT   937
               E   P   Q   G   K   D   R   Q   G   T   R   P   Q   269
              GAG CCC CAG GGC AAA GAC AGG CAG GGG ACC AGG CCC CAA   976
               A   Q   G   P   G   E   G   V   R   P   G   K   A   282
              GCC CAA GGG CCC GGC GAG GGG GTG CGA CCA GGG AAA GCA   1015
               E   K   E   G   A   E   P   T   N   T   V   E   K   295
              GAG AAG GAG GGA GCA GAG CCC ACA AAC ACG GTG GAA AAG   1054
               G   N   V   S   K   D   V   G   S   E   G   K   H   308
              GGG AAT GTC TCT AAG GAC GTA GGG AGT GAA GGG AAG CAC   1093
               V   R   P   Q   I   P   G   R   K   W   G   G   F   321
              GTA AGG CCC CAA ATC CCT GGG AGA AAG TGG GGA GGT TTC   1132
               L   G   R   R   S   K   W   D   G   P   Q   N   K   334
              CTG GGA AGA AGG AGT AAG TGG GAC GGT CCC CAG AAT AAG   1171
               K   D   K   E   G   V   L   L   S   K   A   E   K   347
              AAG GAC AAA GAA GGG GTG CTC TTA AGT AAG GCA GAG AAG   1210
               T   G   E   P   Q   T   Q   M   E   K   T   S   Q   360
              ACA GGT GAG CCT CAG ACC CAG ATG GAG AAG ACA AGC CAA   1249
               V   Q   G   E   L   G   D   D   L   R   M   G   E   373
              GTG CAG GGC GAG TTG GGG GAC GAT CTG AGA ATG GGG GAG   1288
               K   A   G   E   L   R   S   T   T   G   K   A   G   386
              AAA GCA GGT GAG CTT CGG AGC ACG ACT GGG AAG GCA GGT   1327
               E   S   W   D   K   K   E   K   M   G   Q   P   Q   399
              GAG TCC TGG GAT AAG AAG GAA AAG ATG GGG CAA CCC CAG   1366
```

FIG. 2B

```
  G   K   S   G   N   A   G   E   A   R   S   Q   T    412
GGT AAG TCC GGG AAC GCA GGT GAA GCT CGG AGT CAG ACA   1405

E   K   G   C   E   A   P   K   E   V   S   T   M    425
GAG AAG GGC TGT GAA GCC CCA AAG GAG GTG AGC ACA ATG   1444

V   E   S   P   A   A   P   G   K   G   G   W   P    438
GTG GAG TCG CCA GCA GCT CCT GGG AAG GGA GGC TGG CCA   1483

G   S   R   G   Q   E   A   E   E   P   C   S   R    451
GGA AGC CGT GGG CAG GAA GCA GAG GAG CCC TGC TCA AGA   1522

A   G   D   G   A   G   A   L   E   T   E   L   E    464
GCA GGT GAT GGG GCT GGT GCC CTG GAG ACA GAG CTG GAA   1561

G   P   S   Q   P   A   L   E   K   D   A   E   R    477
GGA CCC AGC CAG CCT GCT CTG GAG AAG GAT GCA GAA AGG   1600

P   R   I   R   K   E   N   Q   D   G   P   A   P    490
CCT CGG ATA CGG AAG GAG AAC CAA GAC GGG CCA GCC CCG   1639

Q   E   E   G   K   G   G   Q   S   R   D   S   D    503
CAG GAG GAG GGC AAA GGA GGC CAG AGC AGA GAC TCA GAC   1678

Q   A   P   E   D   R   W   Y   E   A   E   K   V    516
CAG GCT CCT GAG GAC AGA TGG TAT GAG GCA GAG AAA GTC   1717

W   L   A   Q   K   D   G   F   T   L   A   T   V    529
TGG CTG GCT CAG AAG GAT GGA TTT ACT CTT GCT ACG GTG   1756

L   K   P   D   E   G   T   A   D   L   P   A   G    542
CTA AAG CCA GAT GAG GGA ACA GCA GAC CTG CCA GCA GGA   1795

R   V   R   L   C   I   D   A   D   K   T   I   T    555
AGG GTG AGA CTT TGC ATT GAT GCT GAC AAA ACC ATC ACT   1834

E   V   D   E   E   H   V   H   R   A   N   P   P    568
GAG GTG GAT GAG GAG CAT GTC CAT CGG GCC AAC CCT CCT   1873

E   L   D   Q   V   E   D   L   A   S   L   I   S    581
GAG CTG GAC CAG GTC GAG GAC CTG GCC TCT CTC ATC AGT   1912

V   N   E   S   S   V   L   N   T   L   L   Q   R    594
GTC AAC GAA TCC AGT GTC CTG AAC ACG CTT CTG CAG CGC   1951

Y   K   A   Q   L   L   H   T   C   T   G   P   D    607
TAC AAA GCT CAG CTG CTG CAC ACC TGC ACA GGG CCT GAT   1990

L   I   V   L   Q   P   R   G   P   S   V   P   S    620
CTG ATT GTC CTC CAG CCC CGG GGG CCC TCG GTG CCT TCT   2029
```

FIG. 2C

```
  A   G   K   V   P   K   G   R   R   D   G   L   P    633
 GCA GGG AAG GTG CCC AAG GGC CGC CGG GAT GGC CTG CCT  2068
  A   H   I   G   S   M   A   Q   R   A   Y   W   A    646
 GCC CAC ATT GGC TCC ATG GCA CAG CGG GCA TAC TGG GCG  2107
  L   L   N   Q   R   R   D   Q   S   I   V   A   L    659
 CTG CTG AAC CAG CGG AGA GAC CAG AGC ATT GTG GCC CTG  2146
  G   R   S   G   A   G   K   T   T   C   C   E   Q    672
 GGC CGG AGT GGC GCT GGG AAG ACC ACC TGC TGT GAG CAG  2185
  V   L   E   H   L   V   G   M   A   G   S   V   D    685
 GTC CTG GAA CAC CTG GTG GGG ATG GCA GGC AGT GTG GAT  2224
  G   R   V   S   V   E   K   I   R   A   T   F   T    698
 GGC AGG GTC TCA GTG GAG AAG ATC CGA GCC ACC TTC ACT  2263
  V   L   R   A   F   G   S   V   S   M   A   H   S    711
 GTC CTC CGG GCC TTC GGC TCT GTG TCC ATG GCC CAC AGC  2302
  R   S   A   T   R   F   S   M   V   M   S   L   D    724
 CGC AGT GCC ACC CGG TTC TCC ATG GTG ATG TCG CTG GAC  2341
  F   N   A   T   G   R   I   T   A   A   Q   L   Q    737
 TTC AAC GCT ACA GGC CGC ATC ACA GCT GCT CAG CTC CAG  2380
  T   M   L   L   E   K   S   R   V   A   R   Q   P    750
 ACA ATG CTT TTG GAG AAG AGC CGC GTG GCA CGG CAG CCG  2419
  E   G   E   S   N   F   L   V   F   S   Q   M   L    763
 GAA GGG GAA AGT AAC TTC CTG GTT TTC TCC CAG ATG CTG  2458
  A   G   L   D   L   D   L   R   T   E   L   N   L    776
 GCT GGA TTG GAC TTG GAT CTC AGG ACG GAG CTG AAC CTG  2497
  H   Q   M   A   D   S   S   F   G   M   G   V        789
 CAC CAG ATG GCA GAT AGC AGC TCC TTT GGC ATG GGC GTG  2536
  W   S   K   P   E   D   K   Q   K   A   A   A   A    802
 TGG TCC AAG CCT GAA GAT AAA CAG AAG GCG GCA GCT GCC  2575
  F   A   Q   L   Q   G   A   M   E   M   L   G   I    815
 TTT GCC CAG CTC CAG GGT GCC ATG GAG ATG CTG GGC ATC  2614
  S   E   S   E   Q   R   A   V   W   R   V   L   A    828
 TCA GAG AGC GAG CAG CGG GCT GTT TGG CGG GTC CTG GCA  2653
  A   I   Y   H   L   G   A   A   G   A   C   K   V    841
 GCC ATC TAC CAC CTG GGC GCG GCG GGG GCC TGC AAA GTG  2692
  G   R   K   Q   F   M   R   F   E   W   A   N   Y    854
```

FIG. 2D

```
                GGT CGG AAG CAG TTC ATG AGG TTT GAG TGG GCA AAC TAC  2731
  A   A   E   A   L   G   C   E   Y   E   E   L   N           867
GCA GCT GAG GCC CTG GGC TGC GAG TAT GAG GAG CTG AAC            2770
  T   A   T   F   K   H   H   L   R   Q   I   I   Q           880
ACG GCC ACC TTC AAG CAC CAC CTT CGA CAG ATC ATC CAG            2809
  Q   M   T   F   G   P   S   R   W   G   L   E   D           893
CAA ATG ACG TTT GGG CCA AGC CGA TGG GGC CTC GAG GAT            2848
  E   E   T   S   S   G   L   K   M   T   G   V   D           906
GAG GAA ACC AGC TCA GGG CTC AAG ATG ACA GGA GTG GAC            2887
  C   V   E   G   M   A   S   G   L   Y   Q   E   L           919
TGT GTG GAG GGG ATG GCC TCG GGC CTG TAC CAG GAA CTC            2926
  F   A   A   V   V   S   L   I   N   R   S   F   S           932
TTT GCG GCT GTG GTC TCA CTC ATC AAC AGA TCC TTT TCC            2965
  S   H   H   L   S   M   A   S   I   M   V   V   D           945
TCC CAC CAT CTC TCC ATG GCC TCC ATC ATG GTG GTG GAC            3004
  S   P   G   F   Q   N   P   R   H   Q   G   K   D           958
TCT CCA GGC TTC CAG AAC CCC CGG CAC CAG GGC AAG GAC            3043
  R   A   A   T   F   E   E   L   C   H   N   Y   A           971
CGG GCG GCC ACC TTT GAG GAG CTG TGC CAC AAC TAC GCC            3082
  H   E   R   L   Q   L   L   F   Y   Q   R   T   F           984
CAT GAG CGC CTG CAG CTG CTG TTC TAC CAG CGG ACC TTT            3121
  V   S   T   L   Q   R   Y   Q   E   E   G   V   P           997
GTC TCC ACG CTA CAG CGA TAT CAA GAG GAA GGT GTT CCT            3160
  V   Q   F   D   L   P   D   P   S   P   G   T   T          1010
GTG CAG TTT GAC CTC CCG GAC CCC TCC CCA GGG ACC ACC            3199
  V   A   V   V   D   Q   N   P   S   Q   Q   V   R          1023
GTG GCT GTT GTG GAT CAA AAT CCC TCT CAG CAG GTC CGC            3238
  L   P   A   G   G   G   A   Q   D   A   R   G   L          1036
TTA CCA GCT GGA GGA GGT GCC CAG GAT GCC AGA GGC CTT            3277
  F   W   V   L   D   E   E   V   H   V   E   G   S          1049
TTC TGG GTC TTA GAT GAG GAA GTC CAT GTA GAG GGC TCC            3316
  S   D   S   V   V   L   E   R   L   C   A   T   F          1062
AGT GAC AGT GTG GTG CTC GAG CGT CTG TGT GCT ACT TTC            3355
  E   K   K   G   A   G   T   E   G   S   S   A   L          1075
GAG AAG AAA GGA GCT GGG ACT GAA GGG TCC TCT GCC CTG            3394
```

FIG. 2E

```
      R   T   C   E   Q   P   L   Q   C   E   I   F   H   1088
    CGG ACC TGT GAG CAG CCC CTC CAG TGT GAG ATT TTC CAC 3433

Q   L   G   W   D   P   V   R   Y   D   L   T   G   1101
    CAG TTG GGA TGG GAC CCT GTG CGG TAC GAC CTC ACG GGC 3472

W   L   H   R   A   K   P   N   L   S   A   L   D   1114
    TGG CTC CAC AGA GCC AAG CCC AAC CTC TCG GCC CTG GAT 3511

A   P   Q   V   L   Q   Q   S   K   R   E   E   L   1127
    GCA CCC CAG GTC CTG CAA CAG TCA AAA AGA GAG GAG CTG 3550

R   S   L   F   Q   A   R   A   K   L   P   P   V   1140
    CGG AGT CTA TTC CAG GCC CGG GCC AAG CTG CCT CCT GTG 3589

C   R   A   V   A   G   L   E   G   T   S   Q   Q   1153
    TGC CGG GCT GTG GCA GGC CTG GAG GGC ACC TCC CAG CAG 3628

A   L   Q   R   S   R   M   V   R   R   T   F   A   1166
    GCC CTG CAG AGG AGC CGC ATG GTG AGG AGG ACC TTT GCC 3667

S   S   L   A   A   V   R   R   K   A   P   C   S   1179
    AGC AGC CTT GCC GCG GTG AGG AGG AAA GCC CCG TGC TCC 3706

Q   I   K   L   Q   M   D   A   L   T   S   M   I   1192
    CAG ATC AAG CTG CAG ATG GAT GCG CTG ACC AGC ATG ATC 3745

K   R   S   R   L   H   F   I   H   C   L   V   P   1205
    AAA AGG TCC CGG CTG CAC TTT ATC CAC TGC CTG GTA CCA 3784

N   P   V   V   E   S   R   S   G   Q   E   S   P   1218
    AAC CCT GTG GTG GAA AGC AGG AGT GGG CAG GAA TCT CCA 3823

P   P   P   Q   P   G   R   D   K   P   G   A   G   1231
    CCA CCA CCG CAG CCT GGT AGA GAC AAG CCT GGG GCA GGT 3862

G   P   L   A   L   D   I   P   A   L   R   V   Q   1244
    GGA CCT CTG GCC CTG GAT ATC CCA GCA CTG AGG GTC CAG 3901

L   A   G   F   H   I   L   E   A   L   R   L   H   1257
    CTT GCT GGG TTC CAC ATC CTG GAG GCT CTG CGT CTG CAT 3940

R   T   G   Y   A   D   H   M   G   L   T   R   F   1270
    AGG ACA GGC TAT GCT GAC CAC ATG GGG CTC ACT CGC TTC 3979

R   R   Q   F   Q   V   L   D   A   P   L   L   K   1283
    CGC CGG CAA TTC CAG GTG CTG GAC GCT CCA CTC CTG AAG 4018

K   L   M   S   T   S   E   G   I   D   E   R   K   1296
    AAG CTC ATG TCG ACC TCC GAG GGA ATA GAT GAA AGG AAG 4057
```

FIG. 2F

```
  A   V   E   E   L   L   E   T   L   D   L   E   K   1309
GCC GTG GAG GAG CTC CTG GAG ACC CTG GAT CTG GAA AAG  4096

K   A   V   A   V   G   H   S   Q   V   F   L   K   1322
AAG GCG GTG GCT GTG GGG CAC AGC CAA GTT TTT CTC AAG  4135

A   G   V   I   S   R   L   E   K   Q   R   E   K   1335
GCA GGT GTG ATC TCC AGG CTT GAG AAG CAG CGA GAG AAG  4174

L   V   S   Q   S   I   V   L   F   Q   A   A   C   1348
CTG GTA TCT CAG AGC ATC GTT CTC TTC CAG GCG GCT TGC  4213

K   G   F   L   S   R   Q   E   F   K   K   L   K   1361
AAG GGC TTT CTG TCT CGC CAG GAA TTC AAG AAG CTG AAG  4252

I   R   R   L   A   A   Q   C   I   Q   K   N   V   1374
ATT CGC CGA CTG GCT GCA CAG TGC ATC CAG AAG AAT GTG  4291

A   V   F   L   A   V   K   D   W   P   W   W   Q   1387
GCT GTG TTC CTC GCA GTC AAG GAC TGG CCA TGG TGG CAG  4330

L   L   G   S   L   Q   P   L   L   S   A   T   I   1400
CTG CTT GGT TCC CTC CAG CCT CTA CTT AGT GCC ACC ATT  4369

G   T   E   Q   L   R   A   K   E   E   E   L   T   1413
GGA ACT GAG CAG CTC CGA GCC AAG GAG GAG GAG CTT ACA  4408

T   L   R   R   K   L   E   K   S   E   K   L   R   1426
ACG CTA AGA CGG AAG CTA GAA AAA TCA GAG AAG TTG CGG  4447

N   E   L   R   Q   N   T   D   L   L   E   S   K   1439
AAT GAA CTC CGG CAG AAC ACA GAT CTG CTA GAA AGC AAG  4486

I   A   D   L   T   S   D   L   A   D   E   R   F   1452
ATT GCT GAC TTG ACC TCT GAC CTT GCC GAT GAG CGC TTC  4525

K   G   D   V   A   C   Q   V   L   E   S   E   R   1465
AAA GGT GAT GTG GCC TGC CAG GTG CTG GAG AGT GAG CGG  4564

A   E   R   L   Q   A   F   R   E   V   Q   E   L   1478
GCA GAG CGG CTA CAG GCC TTC CGG GAG GTC CAG GAG CTC  4603

K   S   K   H   E   Q   V   Q   K   K   L   G   D   1491
AAG AGC AAG CAT GAA CAA GTC CAG AAA AAA CTG GGA GAT  4642

V   N   K   Q   L   E   E   A   Q   Q   K   I   Q   1504
GTG AAT AAA CAG TTG GAA GAA GCC CAG CAG AAA ATT CAG  4681

L   N   D   L   E   R   D   P   T   G   G   A   D   1517
TTG AAT GAC TTG GAA AGG GAT CCC ACT GGA GGA GCA GAC  4720

```
                                                              GAG TGG CAG ATG CGC TTC GAC TGT GCT CAG ATG GAG AAC  4759
 E   F   L   R   K   R   L   Q   Q   C   E   E   R   1543
GAG TTC CTC AGA AAG CGT CTG CAG CAA TGC GAG GAG AGG           4798
 L   D   S   E   L   T   A   R   K   E   L   E   Q   1556
CTG GAC TCG GAG CTG ACA GCC AGG AAA GAG CTG GAG CAA           4837
 K   L   G   E   L   Q   S   A   Y   D   G   A   K   1569
AAG CTT GGG GAG TTG CAA AGT GCT TAT GAC GGG GCC AAG           4876
 K   M   A   H   Q   L   K   R   K   C   H   H   L   1582
AAG ATG GCT CAC CAA CTG AAG AGG AAG TGC CAC CAT CTT           4915
 T   C   D   L   E   D   T   C   V   L   L   E   N   1595
ACC TGT GAC CTT GAG GAT ACC TGC GTC CTG CTA GAG AAC           4954
 Q   Q   S   R   N   H   E   L   E   K   K   Q   K   1608
CAA CAA AGT CGA AAC CAT GAG CTG GAG AAG AAG CAG AAG           4993
 K   F   D   L   Q   L   A   Q   A   L   G   E   S   1621
AAG TTT GAC CTG CAG CTG GCC CAG GCC CTA GGT GAG TCA           5032
 V   F   E   K   G   L   R   E   K   V   T   Q   E   1634
GTG TTT GAG AAG GGT CTC CGT GAG AAA GTG ACC CAG GAG           5071
 N   T   S   V   R   W   E   L   G   Q   L   Q   Q   1647
AAC ACC AGT GTC CGG TGG GAG CTA GGC CAG CTT CAG CAG           5110
 Q   L   K   Q   K   E   Q   E   A   S   Q   L   K   1660
CAG CTG AAG CAA AAG GAG CAG GAA GCC TCA CAG CTG AAG           5149
 Q   Q   V   E   M   L   Q   D   H   K   R   E   L   1673
CAG CAG GTG GAG ATG CTA CAG GAC CAT AAA CGG GAG CTG           5188
 L   G   S   P   S   L   G   E   N   C   V   A   G   1686
CTG GGG TCA CCC TCT CTG GGG GAA AAT TGC GTT GCT GGC           5227
 L   K   E   R   L   W   K   L   E   S   S   A   L   1699
TTG AAG GAG AGG CTC TGG AAG TTG GAA TCC AGC GCC CTT           5266
 E   Q   Q   K   I   Q   S   Q   Q   E   N   T   I   1712
GAG CAA CAG AAA ATC CAG AGC CAG CAG GAA AAC ACC ATC           5305
 K   Q   L   E   Q   L   R   Q   R   F   E   L   E   1725
AAG CAG CTG GAG CAG CTC CGC CAG CGG TTT GAG CTG GAG           5344
 I   E   R   M   K   Q   M   H   Q   K   D   R   E   1738
ATC GAG CGG ATG AAG CAG ATG CAC CAG AAG GAC CGT GAG           5383
 D   Q   E   E   E   L   E   D   V   R   Q   S   C   1751
GAC CAG GAG GAG GAA CTG GAG GAT GTC CGT CAG TCC TGC           5422
```

FIG. 2H

```
  Q   K   R   L   H   Q   L   E   M   Q   L   E   Q   1764
CAG AAG CGG CTT CAT CAG CTG GAA ATG CAG CTG GAG CAA  5461

E   Y   E   E   K   Q   M   V   L   H   E   K   Q   1777
GAG TAT GAA GAG AAG CAG ATG GTC CTC CAT GAG AAG CAA  5500

D   L   E   G   L   I   G   T   L   C   D   Q   I   1790
GAT TTG GAA GGC TTG ATC GGA ACC CTC TGT GAC CAG ATT  5539

G   H   R   D   F   D   V   E   K   R   L   R   R   1803
GGC CAT CGG GAC TTT GAT GTG GAG AAG CGA CTT CGG AGA  5578

D   L   R   R   T   H   A   L   L   S   D   V   Q   1816
GAC CTC AGG AGG ACA CAT GCA CTG TTG TCA GAC GTG CAG  5617

L   L   L   G   T   M   E   D   G   K   T   S   V   1829
CTC CTT CTG GGC ACC ATG GAG GAT GGC AAG ACA TCA GTC  5656

S   K   E   E   L   E   K   V   H   S   Q   L   E   1842
AGC AAG GAG GAG CTG GAG AAA GTG CAC AGC CAG CTG GAG  5695

Q   S   E   A   K   C   E   E   A   L   K   T   Q   1855
CAG AGT GAA GCC AAG TGT GAG GAG GCC TTG AAG ACG CAG  5734

K   V   L   T   A   D   L   E   S   M   H   S   E   1868
AAG GTG CTC ACA GCG GAC CTG GAG AGC ATG CAC AGC GAG  5773

L   E   N   M   T   R   N   K   S   L   V   D   E   1881
CTG GAG AAC ATG ACG CGG AAC AAG AGC CTG GTG GAT GAG  5812

Q   L   Y   R   L   Q   F   E   K   A   D   L   L   1894
CAG CTG TAC AGG CTG CAG TTT GAG AAG GCG GAC CTC CTG  5851

K   R   I   D   E   D   Q   D   D   L   N   E   L   1907
AAG CGC ATC GAT GAG GAC CAG GAT GAC CTG AAT GAG CTG  5890

M   Q   K   H   K   D   L   I   A   Q   S   A   A   1920
ATG CAG AAG CAC AAG GAC CTC ATT GCT CAG TCT GCT GCT  5929

D   I   G   Q   I   Q   E   L   Q   L   Q   L   E   1933
GAC ATT GGG CAG ATC CAA GAA CTG CAG CTG CAG CTG GAG  5968

E   A   K   K   E   K   H   K   L   Q   E   Q   L   1946
GAA GCC AAG AAG GAG AAG CAC AAG CTA CAA GAA CAA CTG  6007

Q   V   A   Q   M   R   I   E   Y   L   E   Q   S   1959
CAG GTG GCT CAG ATG CGC ATC GAG TAC CTG GAA CAG TCC  6046

T   V   D   R   A   I   V   S   R   Q   E   A   V   1972
ACC GTG GAT CGA GCC ATC GTC AGC AGG CAG GAG GCG GTC  6085
```

FIG. 21

```
  I   C   D   L   E   N   K   T   E   F   Q   K   V   1985
ATC TGT GAC CTA GAG AAC AAG ACA GAG TTC CAG AAG GTG 6124

Q   I   K   R   F   E   V   L   V   I   R   L   R   1998
CAG ATT AAG AGA TTT GAG GTC CTG GTG ATC CGG CTT CGG 6163

D   S   L   I   K   M   G   E   E   L   S   Q   A   2011
GAC AGC CTG ATC AAG ATG GGG GAG GAG CTT TCA CAG GCG 6202

A   T   S   E   S   Q   Q   R   E   S   S   Q   Y   2024
GCC ACC TCC GAG TCC CAG CAG CGG GAG AGC AGC CAG TAC 6241

Y   Q   R   R   L   E   E   L   K   A   D   M   E   2037
TAC CAG CGG CGC CTG GAA GAG CTG AAG GCC GAC ATG GAA 6280

E   L   V   Q   R   E   A   E   A   S   R   R   C   2050
GAG CTG GTG CAG CGG GAG GCA GAG GCC AGC CGG CGG TGC 6319

M   E   L   E   K   Y   V   E   E   L   A   A   V   2063
ATG GAG CTG GAG AAG TAC GTG GAG GAA CTT GCA GCA GTG 6358

R   Q   T   L   Q   T   D   L   E   T   S   I   R   2076
AGG CAA ACC CTC CAG ACA GAC CTG GAG ACA TCC ATT CGG 6397

R   I   A   D   L   Q   A   A   L   E   E   V   A   2089
CGG ATT GCC GAC CTG CAG GCT GCC TTG GAA GAA GTG GCA 6436

S   S   D   S   D   T   E   S   V   Q   T   A   V   2102
TCC AGT GAC AGT GAT ACT GAG AGT GTC CAG ACG GCA GTG 6475

D   C   G   S   S   G   R   K   E   M   D   N   V   2115
GAT TGT GGC AGC AGC GGC CGA AAA GAG ATG GAT AAC GTC 6514

S   I   L   S   S   Q   P   E   G   S   L   Q   S   2128
TCC ATC CTC AGC TCC CAG CCA GAG GGC AGC CTG CAG TCC 6553

W   L   S   C   T   L   S   L   A   T   D   T   M   2141
TGG TTG AGC TGT ACT CTG TCC CTG GCC ACA GAT ACT ATG 6592

R   T   P   S   R   Q   S   A   T   S   S   R   I   2154
AGG ACT CCT TCT CGA CAG TCA GCC ACC AGC AGC CGC ATC 6631

L   S   P   R   I   N   E   E   A   G   D   T   E   2167
CTC AGC CCC AGG ATA AAC GAA GAG GCT GGG GAC ACT GAG 6670

R   T   Q   S   A   L   A   L   S   R   A   R   S   2180
AGG ACC CAG TCG GCA TTG GCA CTG AGC AGA GCC CGG TCC 6709

T   N   V   H   S   K   T   S   G   D   K   P   V   2193
ACC AAT GTC CAC AGC AAG ACC TCA GGA GAC AAG CCT GTT 6748

```
                    TC  CCC CAC TTT GTC CGC CGG CAA AAG TAC TGT CAT TTT  6787
     G   D   G   E   V   L   A   V   Q   R   K   S   T         2219
    GGG GAC GGC GAA GTG CTT GCC GTC CAG AGA AAG TCC ACA         6826
     E   R   L   E   P   A   S   S   P   L   A   S   R         2232
    GAG AGA TTA GAA CCT GCT TCC TCT CCC CTG GCT TCT CGG         6865
     S   T   N   T   S   P   L   S   R   E   K   L   P         2245
    AGT ACA AAT ACA TCC CCG CTG TCG AGG GAA AAG CTG CCC         6904
     S   P   S   A   A   L   S   E   F   V   E   G   L         2258
    AGT CCT TCA GCG GCC CTC TCG GAG TTC GTG GAA GGG CTC         6943
     R   R   K   R   A   Q   R   G   Q   G   S   T   L         2271
    CGG AGG AAG AGA GCC CAG AGA GGC CAG GGG TCC ACG CTG         6982
     G   L   E   D   W   P   T   L   P   I   Y   Q   T         2284
    GGC CTA GAG GAC TGG CCC ACT CTC CCC ATT TAC CAG ACG         7021
     T   G   A   S   T   L   R   R   G   R   A   G   S         2297
    ACT GGG GCC TCC ACA CTA AGG AGG GGC AGG GCT GGC AGT         7060
     D   E   G   N   L   S   L   R   V   G   A   K   S         2310
    GAC GAG GGA AAC CTC TCG CTG AGG GTT GGG GCA AAG TCA         7099
     P   L   E   I   E   G   A   A   G   G   L   L   R         2323
    CCC CTG GAA ATC GAA GGG GCC GCT GGT GGT CTC TTG AGG         7138
     S   T   S   L   K   C   I   S   S   D   G   V   G         2336
    TCC ACC AGC CTC AAA TGC ATC TCT TCA GAC GGT GTT GGG         7177
     G   T   T   L   L   P   E   K   S   K   T   Q   F         2349
    GGC ACA ACC CTA CTC CCC GAA AAG TCG AAA ACC CAA TTC         7216
     S   S   C   E   S   L   L   E   S   R   P   S   M         2362
    AGT TCC TGC GAG TCC CTC TTA GAA TCC AGA CCG AGC ATG         7255
     G   R   K   L   S   S   P   T   T   P   R   D   M         2375
    GGG AGA AAA CTG AGC TCT CCG ACC ACA CCC AGG GAC ATG         7294
     L   L   S   P   T   L   R   P   R   R   R   C   L         2388
    CTG TTG TCG CCC ACA CTG CGT CCT CGG AGG CGG TGT CTG         7333
     E   S   S   V   D   D   A   G   C   P   D   L   G         2401
    GAG TCC TCT GTG GAC GAT GCG GGC TGT CCA GAC CTT GGA         7372
     K   E   P   L   V   F   Q   N   R   Q   F   A   H         2414
    AAG GAG CCG CTT GTT TTC CAG AAC CGC CAG TTT GCC CAC         7411
     L   M   E   E   P   L   G   S   D   P   F   S   W         2427
    CTG ATG GAG GAA CCT CTA GGC AGT GAC CCA TTC AGC TGG         7450
```

FIG. 2K

```
     K   L   P   S   L   D   Y   E   R   K   T   K   V   2440
    AAA CTC CCA AGC CTC GAC TAC GAA CGC AAG ACC AAA GTG   7489
     D   F   D   D   F   L   P   A   I   R   K   P   Q   2453
    GAC TTC GAT GAC TTC CTC CCA GCT ATC CGG AAG CCC CAG   7528
     T   P   T   S   L   A   G   S   A   K   G   G   Q   2466
    ACA CCT ACC TCC TTG GCT GGA TCA GCC AAA GGT GGG CAA   7567
     D   G   S   Q   R   S   S   I   H   F   E   T   E   2479
    GAC GGT TCA CAG CGT TCA AGC ATC CAC TTT GAA ACG GAA   7606
     E   A   N   R   S   F   L   S   G   I   K   T   I   2492
    GAG GCT AAC CGT TCC TTT CTC TCG GGG ATC AAG ACC ATT   7645
     L   K   K   S   P   E   P   K   E   D   P   A   H   2505
    TTG AAG AAG AGC CCG GAG CCC AAG GAG GAT CCC GCT CAC   7684
     L   S   D   S   S   S   S   S   G   S   I   V   S   2518
    CTG TCT GAC TCG TCC TCA TCC TCC GGC TCC ATC GTG TCC   7723
     F   K   S   A   D   S   I   K   S   R   P   G   I   2531
    TTC AAA AGT GCT GAC AGC ATC AAA AGT CGA CCA GGA ATC   7762
     P   R   L   A   G   D   G   G   E   R   T   S   P   2544
    CCA CGA CTT GCG GGT GAC GGT GGC GAG CGA ACG TCC CCC   7801
     E   R   R   E   P   G   T   G   R   K   D   D   D   2557
    GAG CGG AGA GAG CCA GGG ACG GGG AGG AAA GAC GAC GAT   7840
     V   A   S   I   M   K   K   Y   L   Q   K   *       2569
    GTT GCG AGC ATA ATG AAG AAA TAC CTC CAG AAG TAG gaa   7879
    ccagttcagcctccttgaagctgcccttgaagacttcccgactctacaataa  7931
    cttggagacagagagactggccaggcctccccggtggccagagccagccagc  7983
    atggccaccctcaagaggcgagatgagcccacagaggcatatcctgcgggga  8035
    tgctgggctcccagtgtggttggcctgaacaaaataaagtgttgactcctgg  8087
    gcaaaaaaaaaaaaaaaaaaaaaaaaaaaa                        8117
```

FIG. 2L

```
HGDMLP-1   APEDRWYEAEKVWLAQKDGFTLATVLKPDEGTADLPAGRVRLCIDADKTITEVDEEHVHR  60
BAA93660   AAEEAWYETEKVWLVHRDGFSLASQLKSEE--LSLPEGKARVKLDHDGAILDVDEDDIEK  58
BAA13206   ------------------------------------------------------------

HGDMLP-1   ANPPELDQVEDLASLISVNESSVLNTLLQRYKAQLLHTCTGPDLIVLQPRGP----SVPS  116
BAA93660   ANAPSCDRLEDLASLVYLNESSVLHTLRQRYGASLLHTYAGPSLLVLSTRGAPAVYSEKV  118
BAA13206   ------------------------------------------------------------

HGDMLP-1   AGKVPKGRRDGLPAHIGSMAQRAYWALLNQRRDQSIVALGRSGAGKTTCCEQVLEHLVGM  176
BAA93660   MHMFKGCRREDMAPHIYAVAQTAYRAMLMSRQDQSIVLLGSSGSGKTTSFQHLVQYLATI  178
BAA13206   MHMFKGCRREDMAPHIYAVAQTAYRAMLMSRQDQSIILLGSSGSGKTTSCQHLVQYLATI  60
                 **  :.:,.**  ::** ** *.* *.**** ** **.****  :::::*. :

HGDMLP-1   AGSVDGRVS-VEKIRATFTVLRAFGSVSMAHSRSATRFSMVMSLDFNATGRITAAQLQTM  235
BAA93660   AGTSGTKVFSVEKWQALSTLLEAFGNSPTIMNGSATRFSQILSLDFDQAGQVASASIQTM  238
BAA13206   AGISGNKVFSVEKWQALYTLLEAFGNSPTIINGNATRFSQILSLDFDQAGQVASASIQTM  120
           ** .:* ***.**  *.* ***  . .    .***** ::****: .*.:::*.:***

HGDMLP-1   LLEKSRVARQPEGESNFLVFSQMLAGLDLDLRTELNLHQMADSSSFGMGVWSKPEDKQKA  295
BAA93660   LLEKLRVARRPASEATFNVFYYLLACGDATLRTELHLNHLAENNVFGIVPLSKPEEKQKA  298
BAA13206   LLEKLRVARRPASEATFNVFYYLLACGDGTLRTELHLNHLAENNVFGIVPLAKPEEKQKA  180
           **** ****.*  .* * ** :::* *  * ***** *::.:*;.. **: :***.****

HGDMLP-1   AAAFAQLQGAMEMLGISESEQRAVWRVLAAIYHLGAAG----ACKVGRKQFMRFEWANYA  351
BAA93660   AQQFSKLQAAMKVLAISPEEQKTCWLILASIYHLGAAGATKEAAEAGRKQFARHEWAQKA  358
BAA13206   AQQFSKLQAAMKVLGISPDEQKACWFILAAIYHLGAAGATKEAAEAGRKQFARHEWAQKA  240
           *  *::** **:.** ** . **:: * *.:************ *.:: ***** * **: *

HGDMLP-1   AEALGCEYEELNTATFKHHLRQIIQQMTFGPSRWGLEDEETSSGL--KMTGVDCVEGMAS  409
BAA93660   AYLLGCSLEELSSAIFKHQLKGGTLQRSTS-FRQGPEESGLGEGT--KLSALECLEGMAS  415
BAA13206   AYLLGCSLEELSSAIFKHQHKGGTLQRSTS-FRQGPEESGLGDGTGPKLSALECLEGMAA  299
           * ***. ***..* ***:   * :,   *  ; ,*** *:.   ..* *::;:*.****:

HGDMLP-1   GLYQELFAAVVSLINRSFSSHHLSMASIMVVDSPGFQNPRHQGKDRAATFEELCHNYAHE  469
BAA93660   GLYSELFTLLISLVNRALKSSQHSLCSMMIVDTPGFQNPEWGGSARGASFEELCHNYAQD  475
BAA13206   GLYSELFTLLVSLVNRALKSSQHSLCSMMIVDTPGFQNPEQGGSARGASFEELCHNYTQD  359
           ***.***:  ::.:**.**::  : * :.*:.**::******  *. *.*******:::

HGDMLP-1   RLQLLFYQRTFVSTLQRYQEEGVPVQFDLPDPSPGTTVAVVDQNPSQQVRLPAGGGAQDA  529
BAA93660   RLQRLFHERTFLQELERYKEDNIELAFDDLEPVADDSVAAVDQ-ASH--LVRSLAHADEA  532
BAA13206   RLQRLFHERTFVQELERYKEENIELAFDDLEPPTDDSVAAVDQ-ASHQSLVRSLARTDEA  418
           *** **::***:. * **::: :       ** .. :* ***  *  :  : : ::::*

HGDMLP-1   RGLFWVLDEEVHVEGSSDSVVLERLCATFEKKGAGTEGSSALRTCEQPLQCEIFHQLGWD  589
BAA93660   RGLLWLLEEEALVPGATEDALLDRLFSYYGPQEGDKKGQSPLLRSSKPRHFLLGHSHGTN  592
BAA13206   RGLLWLLEEEALVPGASEDTLLERLFSYYGPQEGDKKGQSPLLHSSKPHHFLLGHSHGTN  478
           ***:*:*:.**   * * :: :**  :  * :::.  :.  :* * ..*  .* : *.*  *  ;

HGDMLP-1   PVRYDLTGWLHRAKPNLSALDAPQVLQQSKREELRSLFQARAKLPPVCR-AVAGLEGTSQ  648
BAA93660   WVEYNVAGWLNYTKQNPATQNAPRLLQDSQKKIISNLFLGRAGSATVLSGSIAGLEGGSQ  652
BAA13206   WVEYNVTGWLNYTKQNPATQNVPRLLQDSQKKIISNLFLGRAGSATVLSGSIAGLEGGSQ  538
            * :*::.***: :*.* ::: * ::*:*::: :.** .**. . * . ::*******

HGDMLP-1   QALQRSRMVRRTFASSLAAVRRKAPCSQIKLQMDALTSMIKRSRLHFIHCLVPNPV---V  705
BAA93660   LALRRATSMRKTFTTGMAAVKKKSLCIQIKLQVDALIDTIKRSKMHFVHCFLPVAEGWPG  712
BAA13206   LALRRATSMRKTFTTGMVAVKKKSLCIQMKLQVDALIDTIKKSKLHFVHCFLPVAEGWAG  598
           **:*:. .:*:**::::.**::*: * *:***:***. :**:*::**:***::*  *
```

FIG. 3A

```
HGDMLP-1    ESRSGQESPPPPQPGRDKPGAG----GPLALDIPALRVQLAGFHILEALRLHRTGYADHM  761
BAA93660    EPRSASSRRVSSSSELDLPPGDPCEAGLLQLDVSLLRAQLRGSRLLDAMRMYRQGYPDHM  772
BAA13206    EPRSASSRRVSSSSELDLPSGDHCEAGLLQLDVPLLRTQLRGSRLLDAMRMYRQGYPDHM  658
            *.**...    .... * .. ***.** * ..*.*.*.* *.***

HGDMLP-1    GLTRFRRQFQVLDAPLLKKLMSTSEGIDERKAVEELLETLDLEKKAVAVGHSQVFLKAGV  821
BAA93660    VFSEFRRRFDVLAPHLTKKHGRNYIVVDEKRAVEELLESLDLEKSSCCLGLSRVFFRAGT  832
BAA13206    VFSEFRRRFDVLAPHLTKKHGRNYIVVDERRAVEELLBCLDLEKSSCCMGLSRVFFRAGT  718
             :.***.*:.** . * **    . :**::******* **** .  ..* *:.**:.**

HGDMLP-1    ISRLEKQREKLVSQSIVLFQAACKGFLSRQEFKKLKIRRLAAQCIQKNVAVFLAVKDWPW  881
BAA93660    LARLEEQRDEQTSRHLTLFQAACRGYLARQHFKKRKIQDLAIRCVQKNIKKNKGVKDWPW  892
BAA13206    LARLEEQRDEQTSRNLTLFQAACRGYLARQHFKKRKIQDLAIRCVQKNIKKNKGVKDWPW  778
            :.***.**.:  .*: ****** *:*** ****:**. ** :  *:.***:     ******

HGDMLP-1    WQLLGSLQPLLSATIGTEQLRAKEEELTTLRRKLEKSEKLRNELRQNTDLLESKIADLTS  941
BAA93660    WKLFTTVRPLIQVQLSEEQIRNKDEEIQQLRSKLVEKERNELRLSSDRLETRISELTS   952
BAA13206    WKLFTTVRPLIEVQLSEEQIRNKDEEIQQLRSKLEKAEKERNELRLNSDRLESRISELTS  838
            *:*. :::.**:. :. *::*  * *:** **** **  *:* *.* **:.*::**

HGDMLP-1    DLADERFKGDVACQVLESERAERLQAPREVQELKSKHEQVQKKLGDVNKQLEEAQQKIQL 1001
BAA93660    ELTDERNTGESASQLLDAETAERLRTEKEMKELQTQYDALKKQMEVMEMEVMEARLIRAA 1012
BAA13206    ELTDERNTGESASQLLDAETAERLRAEKEMKELQTQYDALKKQMEVMEMEVMEARLIRAA  898
            :* ***  *.:  .*  *.:*.***:       **.     ::*  **     :  **

HGDMLP-1    N-DLERDPTGGADEWQMRFDCAQMENEFLRKRLQQ-CEERLDSELTARKELEQKLGELQS 1059
BAA93660    EINGEVDDDDAGGEWRLKYERAVREVDFTKKRLQQELEDKMEVEQQSRRQLERRLGDLQA 1072
BAA13206    EINGEVDDDDAGGEWRLKYERAVREVDFTKKRLQQEFEDKLEVEQQNKRQLERRLGDLQA  958
            :   * *    ..,**::::. * .:*  *****  *::: * .:    :..** **.**:

HGDMLP-1    AYDGAKKMAHQLKRKCHHLTCDLEDTCVLLENQQSRNHELEKKQKKFDLQLAQALGESVF 1119
BAA93660    DSDESQRALQQLKKKCQRLTAELQDTKLHLEGQQVRNHELEKKQRRFDSELSQAHEETQR 1132
BAA13206    DSEESQRALQQLKKKCQRLTAELQDTKLHLEGQQVRNHELEKKQRRFDSELSQAHEEAQR 1018
            :  ::   .:***:**.:**  .:** .:**  .  ** ********.:.**   *:**   *:

HGDMLP-1    EKGLREKVTQENTSVRWELGQLQQQLKQEQEASQLKQQVEMLQDHKRELLGSPSLGENC  1179
BAA93660    EKLQREKLQREKDMLLAEAFSLKQQMEEKDLDIAGFTQKVVSLEAELQDISSQESKDEAS 1192
BAA13206    EKLQREKLQREKDMLLAEAFSLKQQLEEKDMDIAGFTQKVVSLEAELQDISSQESKDEAS 1078
            **  ***. :*: :   *  *.:**::. :  *  *.*:   *: ::..*    * .*  .

HGDMLP-1    VAGLKERLWKLESSSALEQQKIQSQQENTIKQLEQLRQRFELEIERMKQMHQKDREDQEEE 1239
BAA93660    LAKVKKQLRDLEAKVKDQEEELDEQAGSIQMLEQAKLRLEMEMERMRQTHSKEMESRDEE 1252
BAA13206    LAKVKKQLRDLEAKVKDQEEELDEQAGTIQMLEQAKLRLEMEMERMRQTHSKEMESRDEE 1138
            :.* .*::*. .**:. .*: . :*: **:  *:*.*: *.**  *.*:   * :.:.**

HGDMLP-1    LEDVRQSCQKRLHQLEMQLEQEYEEKQMVLHEKQDLEGLIGTLCDQIGHRDFDVEKRLRR 1299
BAA93660    VEEARQSCQKKLKQMEVQLEBEYEDKQKALREKRELESKLSTLSDQVNQRDFESEKRLRK 1312
BAA13206    VEEARQSCQKKLKQMEVQLEEEYEDKQKVLREKRELEGKLATLSDQVNRRDFESEKRLRK 1198
            :*:.******:*:*:*:***.***:**  * ** :** .* ***.*:. ***.*****:

HGDMLP-1    DLRRTHALLSDVQLLLGTMEDGKTSVSKEELEKVHSQLEQSEAKCEEALKTQKVLTADLE 1359
BAA93660    DLKRTKALLADAQIMLDHLKN--NAPSKREIAQLKNQLEESEFTCAAAVKARKAMEVEME 1370
BAA13206    DLKRTKALLADAQLMLDHLKN--SAPSKREIAQLKNQLEESEFTCAAAVKARKAMEVEIE 1256
            **:**:***:*.*::*   :    . *:**.*:: ***:**  *  *:*::** * :*

HGDMLP-1    SMHSELENMTRNKSLVDEQLYRLQFEKADLLKRIDEDQDDLNELMQKHKDLIAQSAADIG 1419
BAA93660    DLHLQIDDIAKAKTALEEQLSRLQREKNEIQNRLEEDQEDMNELMKKHKAAVAQASRDMA 1430
BAA13206    DLHLQIDDIAKAKTALEEQLSRLQREKNEIQNRLEEDQEDMNELMKKHKAAVAQASRDLA 1316
            .:*  :::::::  *: :::*** *:  :.:** *** ****:***.  .*:*::* *..
```

FIG. 3B

```
HGDMLP-1   QIQELQLQLEEAKKEKHKLQEQLQVAQMRIEYLEQSTVDRAIVSRQEAVICDLENKTEFQ  1479
BAA93660   QMNDLQAQIEESNKEKQELQEKLQALQSQVEFLEQSMVDKSLVSRQEAKIRELETRLEFE  1490
BAA13206   QINDLQAQLEEANKEKQELQEKLQALQSQVEFLEQSMVDKSLVSRQEAKIRELETRLEFE  1376
           *:.:**  *:**::***:;.***.**.  *  *::*:*** **::;******  *  .**:  **:

HGDMLP-1   KVQIKRFEVLVIRLRDSLIKMGEELSQAATSESQQRESSQYYQRRLEELKADMEELVQRE  1539
BAA93660   KTQVKRLENLASRLKETMEKLTEERDQRAAAENREKEQNKRLQRQLRDTKEEMSELARKE  1550
BAA13206   RTQVKRLESLASRLKENMEKLTEERDQRIAAENREKEQNKRLQRQLRDTKEEMGELARKE  1436
           ;.*:**:*.* *. **:;.: *: ** .*  ;;:*..::*..:  **:*.:  * :* **.::*

HGDMLP-1   AEASRRCMELEKYVEELAAVRQTLQTDLETSIRRIADLQAALEEVASSDSDTESVQTAVD  1599
BAA93660   AEASRKKHELEMDLESLEAANQSLQADLKLAFKRIGDLQAAIEDEMESDENEDLINSEGD  1610
BAA13206   AEASRKKHELEMDLESLEAANQSLQADLKLAFKRIGDLQAAIEDEMESDENEDLINSEGD  1496
           *****:   ***  :*,* .*.  *:**:** :::**.*****:*:   .**.:  : :::   *

HGDMLP-1   CGSSGRKEMDNVSILSSQPEGSLQSWLSCTLSLATDTMRTPSRQSATSSRILSPRINEEA  1659
BAA93660   S--------DVDSELEDRVDG-VKSWLS--------KNKGPSK-----------------  1636
BAA13206   S--------DVDSELEDRVDG-VKSWLS--------KNKGPSK-----------------  1522
           .     *   *  *..: :*  ;;****          . : **;

HGDMLP-1   GDTERTQSALALSRARSTNVHSKTSGDKPVSPHFVRRQKYCHFGDGEVLAVQRKSTERLE  1719
BAA93660   ----------APSDDGSLKSSSPTSHWKPLAPDPSDDE--------------HDPVD    1669
BAA13206   ----------AASDDGSLKSSSPTSYWKSLAPDRSDDE--------------HDPLD    1555
                     * *  *:  : *  ** *.;:*.   :                    :  ::

HGDMLP-1   PASSPLASRSTNTSPLSREKLPSPSA  1745
BAA93660   SISRPRFSHSYLSDSDTEAKLTETSA  1695
BAA13206   NTSRPRYSHSYLSDSDTEAKLTETNA  1581
           .  *  *:*  ;.. :.  **....*
```

FIG. 3C

Sequences Aligned

Query: myocilin [Homo sapiens]: Length 504 (1 .. 504)

Sbjct: hGDMLP-1: Length 2568 (1 .. 2568)

Region of Optimal Alignment

```
Query:   82  RLDLEATKARLSSLESLLHQLTLDQAARPQETQEGLQRELGTLRRERDQ-LETQ---TRE  137
             R DL  T A LS ++ LL  +   + +E  E +  +L     +  ++ L+TQ   T +
Sbjct: 1802  RRDLRRTHALLSDVQLLLGTMEDGKTSVSKEELEKVHSQLEQSEAKCEEALKTQKVLTAD  1861

Query:  138  LETAYS---NLLRDKSVLEEEKKRLRQENENLARRLESSSQEVARL  180
             LE+ +S    N+ R+KS+++E+  RL+ E  +L +R++    ++ L
Sbjct: 1862  LESMHSELENMTRNKSLVDEQLYRLQFEKADLLKRIDEDQDDLNEL  1907
```

Statistics

Identities = 30/106 (28%), Positives = 58/106 (54%), Gaps = 7/106 (6%)

FIG. 4

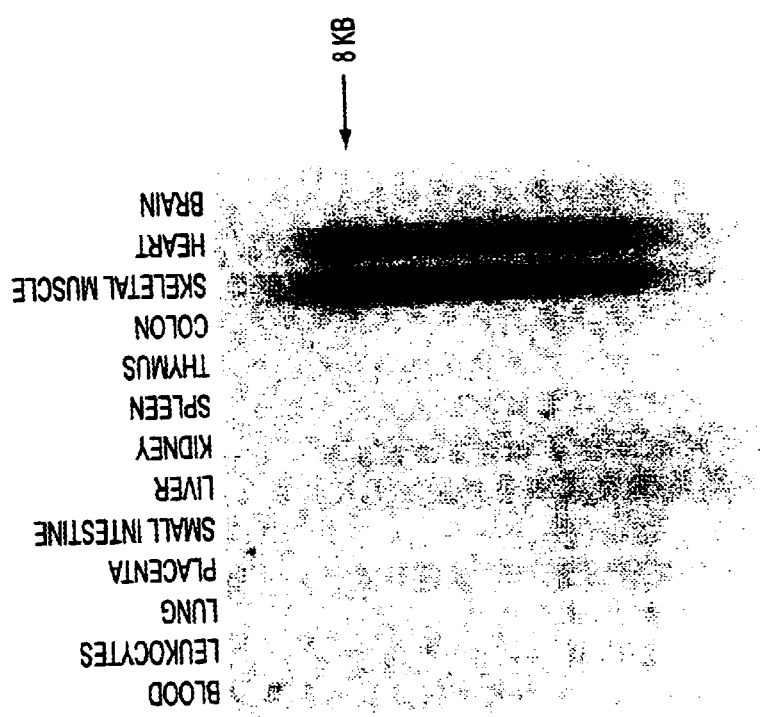

POLYNUCLEOTIDE ENCODING A HUMAN MYOSIN-LIKE POLYPEPTIDE EXPRESSED PREDOMINANTLY IN HEART AND MUSCLE

CROSS REFERENCE TO RELATED APPLICATIONS

This application claims priority under 35 U.S.C. §119(e) to provisional applications for U.S. Patent No. 60/207,456, filed May 26, 2000, No. 60/234,687, filed Sep. 21, 2000, No. 60/236,359, filed Sep. 27, 2000, and No. 60/266,860, filed Feb. 5, 2001, claims priority under 35 U.S.C. §365(c) and is a continuation-in-part of international application nos. PCT/US01/00666, PCT/US01/00667, PCT/US01/00664, PCT/US01/00669, PCT/US01/00665, PCT/US01/00668, PCT/US01/00663, PCT/US01/00662, PCT/US01/00661, PCT/US01/00670, all filed Jan. 30, 2001, and claims priority under 35 U.S.C. §119(a) to GB 0024263.6, filed Oct. 4, 2000, the disclosures of which are incorporated herein by reference in their entireties.

The present application includes a Sequence Listing filed herewith on a single (CD-R) compact disc, provided in duplicate. The Sequence Listing is presented in a single file named "amended sequence.txt", last modified Nov. 26, 2002 2:32:50 am, and having 2,312,956 bytes, the disclosure of which is incorporated herein by reference in its entirety.

FIELD OF THE INVENTION

The present invention relates to a novel myosin-like protein particularly expressed in human heart and muscle, isolated nucleic acids encoding the myosin-like protein, compounds and compositions derivable directly or indirectly therefrom, and diagnostic and therapeutic methods for using the same.

BACKGROUND OF THE INVENTION

Myosins are ubiquitous proteins that act as intracellular engines, typically motoring along tracks of actin filaments within the cell to drive a variety of cellular processes including muscular contraction, cytokinesis, membrane trafficking and signal transduction. Baker et al., *Curr. Opin. Cell Biol.* 10: 80–86 (1998). Given the range of intracellular passengers and itineraries, some form of the myosin protein is found in virtually all eukaryotic cells.

The myosin gene superfamily has at least seventeen members, or classes, encoded by multiple genes.

Mammalian cells have the largest number of myosin genes, with the 28 identified myosin genes belonging to nine classes. Sellers, *Biochim. Biophys. Acta* 1496: 3–22 (2000). The genome of the yeast, *Saccharomyces cerevisiae*, contains just 5 myosin genes. Brown, *Curr. Opin. Cell Biol.* 9: 44–48 (1997). Between these extremes, the nematode *Caenorhabditis elegans* has 14 identified myosin genes. Baker et al., *J. Mol. Biol.* 172: 523–535 (1997). Myosins are also found in plant cells, with myosin genes in classes VIII, XI and XIII expressed exclusively in plants.

The structure of myosin always includes one or two heavy chains and several light chains.

The heavy chain is composed of three structurally and functionally different domains. The head domain, which is highly conserved across the myosin family, functions to generate force, and contains actin-binding and ATP-binding sites; the ATPase activity of the head domain is activated by actin binding. The neck region, which mediates association with the light chains, regulates the adjacent head domain. The tail domain regulates the specific activity of each myosin.

The light chains of myosin I and myosin V are calmodulin, which is a calcium-binding regulatory subunit in certain enzymes. Myosin II is also regulated by calcium-binding light chains, but not calmodulin.

Together, the disparate myosin heavy and light chains permit myosins to serve disparate cellular roles.

For example, in brush border microvilli, myosin I, one of the two most abundant forms of myosin, links the microfilament bundles to the plasma membrane.

Myosin II, the other of the two most abundant myosin classes, forms dimers in muscle cells that associate to form thick filaments, which are part of the contractile apparatus.

In addition to its well characterized role in contraction and force production in skeletal, cardiac, and smooth muscles, myosin II is required for cytokinesis, cell motility, cell polarity/chemotaxis, maintaining cell architecture and development in nonmuscle cells. Sellers, *Biochim. Biophys. Acta* 1496:3–22 (2000).

Thus, contractile bundles, which comprise both actin and myosin II filaments, are found in numerous cell types. In epithelial cells, these bundles are called the circumferential belt and can function structurally (e.g., as an internal brace helping to control cell shape), or for motility (e.g., in wound healing, contraction seals the gap in a sheet of cells).

Myosin II is an integral component to the cytoskeletal substructure, acting to stiffen cortical membranes. In cytokinesis, myosin II plays an essential role performing the motor function for the contractile ring which constricts to form the cleavage furrow.

Myosin IXs, identified in rat, human and *C. elegans*, are expressed in a wide variety of tissues and cell types and are believed to be involved in intracellular signaling pathways. Myosin IX acts as a negative regulator of Rho (a G-protein), suggesting that it may control the Rho signaling pathways involved in cytoskeleton reorganization and other cellular processes. Bahler et al., *Biochim. Biophys. Acta* 1496:52–59 (2000). However the precise cellular functions of the myosin IXs and their exact roles in the Rho signaling pathways have still to be determined.

Membrane-bound myosins of various classes, particularly myosin I and myosin V, have been implicated in movement of vesicles within the cell. Due to its co-localization with Golgi membrane, myosin I is thought to move membrane vesicles between membrane compartments in the cytoplasm. Myosin I also serves as a membrane-microfilament linkage in microvilli.

In yet other examples of myosin function, protein secretion in yeast is disrupted by mutation in the myosin V gene, suggesting an important role for myosin V. In vertebrate brain tissue, myosin V is concentrated in the Golgi stacks and at the tips of membrane processes extending from neuronal cells. Espreafico et al., *J. Cell Biol.* 119: 1541 (1992). This type of membrane association would be consistent with the effects of myosin V mutations in mice, which adversely affect synaptic transmission, resulting in seizures and eventually death. In cell migration, different myosins localize to different regions of the cell. Myosin I localizes to the leading edge of a crawling amoeba, possibly participating in the translocation phase, whereas myosin II is more concentrated at the tail, where it is involved in retraction of the cell body.

Given their ubiquity, and the wide variety of tasks driven by myosins, it is not surprising that myosin defects have been implicated in a wide variety of diseases.

For example, as noted above, myosin V mutations in mice adversely affect synaptic transmission, resulting in seizures and eventually death.

Myosin and myosin-like genes have also been implicated in a number of human diseases.

For example, myosin plays a role in hypertrophic cardiomyopathy. An autosomally dominant form of the disease is frequently caused by a missense point mutation in exon 13 of the cardiac myosin heavy chain gene on chromosome 14. Less often, an abnormal cardiac myosin heavy chain hybrid gene is present.

As another example, mutation in the gene encoding myosin VIIA is responsible for some forms of Usher syndrome. Weil et al., *Nature* 374:60–61 (1995). Usher Syndrome is characterized by hearing impairment associated with retinitis pigmentosa.

Three classes of myosins, VI, VII and XV have been associated with genetic deafness disorders in mammals. Hasson, *Am. J. Hum. Genet.* 61:801–5 (1997); Redowicz, *J. Muscle Res. Cell Mot.* 20:241–248 (1999). Mutations in these myosins result in abnormalities in the stereocilia in the sensory cells of the inner ear of mice.

Other myosin-like genes may also be needed for normal stereociliary function in the inner ear, and mutations in these additional myosin-like genes may thus underlie or contribute to various forms of congenital deafness. For example, nonsyndromic hereditary deafness (DFNA17), mapped to chromosome 22q12.2-q13.3 in 1997, has now been associated with mutation in MYH9, a nonmuscle-myosin heavy-chain gene, located within the linked region. Lalwani et al., *Am. J. Hum. Genet.* 67:1121–8 (2000).

Despite the long-standing interest in myosins and sequence similarity among classes and across species, not all myosin and myosin-like genes have yet been identified, even in species that are genetically well characterized.

For example, a novel myosin-like gene (MysPDZ) has recently been cloned from mouse bone marrow stromal cells. The protein encoded by this newly identified gene contains a PDZ domain but no actin-binding domain. Furusawa et al., *Biochem. Biophys. Res. Comm.* 270: 67–75 (2000). PDZ domains are implicated in modular protein—protein interactions, also binding to specific C-terminal sequences of membrane proteins. Gee et al., *Biochem.* 39: 14638–46 (2000).

MysPDZ appears to localize in the cytoskeleton. Furusawa et al. show significant similarity between MysPDZ and a genomic clone from human chromosome 17; a human orthologue has been identified which contains an ATP/GTP-binding site. Nagase et al., *DNA Res.* 3: 321–329 (1996). Another PDZ-domain containing protein in humans has been shown to associate with actin filaments, possibly through binding to alpha-actinin. Bauer et al., *Blood* 96: 4236–45 (2000).

And in humans, genes for other new myosin-like proteins have recently been cloned. See, e.g., WO 00/26372, and U.S. Pat. No. 6,001,593, the disclosures of which is incorporated herein by reference in its entirety.

Given the importance of myosins in normal cellular processes and in disease, there is a need in the art for access to as yet undiscovered myosin and myosin-like genes.

Furthermore, diseases of the heart and vascular system are a significant cause of human morbidity and mortality. Increasingly, genetic factors are being found that contribute to predisposition, onset, and/or aggressiveness of most, if not all, of these diseases. There is a need for methods and apparatus that permit prediction, diagnosis and prognosis of diseases of the human heart.

SUMMARY OF THE INVENTION

These and other needs in the art are satisfied by the present invention, which provides compounds, compositions and methods based upon the identification and cloning of a novel human myosin-like protein, hGDMLP-1, which is expressed at high levels in human heart and also in skeletal muscle.

In a first aspect, the invention provides an isolated nucleic acid comprising: (i) the nucleotide sequence of SEQ ID NO:1, the full length cDNA sequence, (ii) the nucleotide sequence of SEQ ID NO:2, which presents the hGDMLP-1 cDNA open reading frame, (iii) a nucleotide sequence that is a degenerate variant of the nucleotide sequence of SEQ ID NO:2, (iv) a nucleotide sequence that encodes a polypeptide with the amino acid sequence of SEQ ID NO:3, which is the full length amino acid sequence of hGDMLP-1, (v) a nucleotide sequence that encodes a polypeptide with the amino acid sequence of SEQ ID NO:3 with conservative amino acid substitutions; (vi) a nucleotide sequence that encodes a polypeptide with the amino acid sequence of SEQ ID NO:3 with moderately conservative amino acid substitutions, or (vii) a nucleotide sequence that is the complement of the nucleotide sequence of any one of (i)–(vi).

As would be understood, the isolated nucleic acid that encodes hGDMLP-1 can be either genomic or transcript-derived.

The invention also provides an isolated nucleic acid comprising a nucleotide sequence that hybridizes under high stringency conditions to a probe, the sequence of which probe (i) consists of SEQ ID NO:2, (ii) encodes a polypeptide having the sequence of SEQ ID NO:3, (iii) encodes a polypeptide having the sequence of SEQ ID NO:3 with conservative amino acid substitutions, or (iv) is the complement of (i)–(iii), wherein the isolated nucleic acid is nonidentical in sequence to GenBank accession no. AA993492 and is less than 50 kb in length.

As further described below, GenBank accession no. AA993492 is an anonymous EST identical in sequence to portions of exons 15 and 16 of hGDMLP-1. By "nonidentity" is intended that the nucleic acid of the present invention have fewer, additional, or at least one nucleotide different from that of AA993492.

The invention further provides an isolated nucleic acid comprising a nucleotide sequence that hybridizes under moderate stringency conditions to a probe, the sequence of which probe (i) consists of SEQ ID NO:2, (ii) encodes a polypeptide having the sequence of SEQ ID NO:3, (iii) encodes a polypeptide having the sequence of SEQ ID NO:3 with conservative amino acid substitutions; or (iv) is the complement of (i)–(iii), wherein the isolated nucleic acid is nonidentical in sequence to GenBank accession no. AA993492 and is less than 50 kb in length.

In a related aspect, the invention provides an isolated nucleic acid comprising a nucleotide sequence that encodes at least 8 contiguous amino acids of SEQ ID NO:3, wherein the isolated nucleic acid is nonidentical in sequence to GenBank accession no. AA993492 and is less than 50 kb in length.

The invention also provides an isolated polynucleotide comprising a fragment of at least 17 nucleotides of the isolated nucleic acid of any one of claims 1–3, wherein the isolated nucleic acid is nonidentical in sequence to GenBank accession no. AA993492 and is less than 50 kb in length.

In useful embodiments of the isolated nucleic acids of the present invention, the isolated nucleic acid encodes a polypeptide having ATPase activity. In further useful embodiments, the isolated nucleic acids encode a polypeptide capable of binding calmodulin. Typically, the nucleic acids of the present invention are expressed in both skeletal muscle and heart muscle.

In another aspect, the invention provides the isolated nucleic acid molecule of the present invention operably linked to one or more expression control elements.

The invention further provides a replicable vector comprising an isolated nucleic acid molecule of the present invention.

In a further aspect, the invention provides a host cell transformed to contain the nucleic acid molecule of the present invention, or the progeny thereof.

In a related aspect, the invention provides a method for producing a polypeptide, the method comprising: culturing the transformed host cell of the present invention under conditions in which the protein encoded by the nucleic acid molecule is expressed.

Accordingly, the invention provides hGDMLP-1 polypeptides. In some embodiments, the polypeptide of the present invention is produced by the method described above.

In other embodiments, the invention provides an isolated polypeptide selected from the group consisting of: (a) an isolated polypeptide comprising the amino acid sequence of SEQ ID NO:3; (b) an isolated polypeptide comprising a fragment of at least 8 amino acids of SEQ ID NO: 3; (c) an isolated polypeptide according to (a) or (b) in which at least 95% of deviations from the sequence of (a) or (b) are conservative substitutions; and (d) an isolated polypeptide having at least 65% amino acid sequence identity to the isolated polypeptide of (a) or (b).

In another aspect, the invention provides an isolated antibody or antigen-binding fragment or derivative thereof, the binding of which can be competitively inhibited by a polypeptide of the present invention.

The invention also provides a method of identifying binding partners for a polypeptide according to the present invention, the method comprising: contacting the polypeptide to a potential binding partner; and determining if the potential binding partner binds to said polypeptide.

In another aspect, the invention provides a method of modulating the expression of a nucleic acid of the present invention, the method comprising: administering an effective amount of an agent which modulates the expression of the nucleic acid. The invention further provides a method of modulating at least one activity of a polypeptide according to the present invention, the method comprising: administering an effective amount of an agent which modulates at least one activity of a polypeptide according to the present invention.

In another aspect, the invention provides a transgenic non-human animal or transgenic plant modified to contain a nucleic acid molecule of the present invention and a transgenic non-human animal unable to express the orthologue of the polypeptide of the present invnetion.

In another aspect, the invention provides a method of diagnosing a disease caused by mutation in human hGDMLP-1, comprising: detecting the mutation in a sample of nucleic acids that derives from a subject suspected to have said disease.

In a further aspect, the invention provides a method of diagnosing or monitoring a disease caused by altered expression of human hGDMLP-1, comprising: determining the level of expression of human hGDMLP-1 in a sample of nucleic acids or proteins that derives from a subject suspected to have said disease, alterations from a normal level of expression providing diagnostic and/or monitoring information.

The invention further provides pharmaceutical compositions, including compositions separately comprising the nucleic acids, proteins, antibodies, antagonists and agonists of the present invention and a pharmaceutically acceptable excipient.

In a related aspect, the invention provides a method for treating or preventing a disorder associated with decreased expression or activity of human hGDMLP-1, the method comprising administering to a subject in need of such treatment an effective amount of the pharmaceutical composition comprising the nucleic acid, protein, or hGDMLP-1 agonist of the present invention.

Analogously, the invention further provides a method for treating or preventing a disorder associated with increased expression or activity of human hGDMLP-1, the method comprising administering to a subject in need of such treatment an effective amount of the pharmaceutical composition comprising an antibody or antagonist of the present invention.

The invention provides diagnostic compositions comprising, e.g., the nucleic acid, antibody, or polypeptide of the present invention, the nucleic acid being detectably labeled. In some embodiments, the diagnostic composition is suitable for in vivo administration.

In another embodiment, the invention provides the isolated nucleic acid molecule of the present invention attached to a substrate, and a microarray, at least one probe of which microarray is a nucleic acid according to the present invention.

The invention further provides a method for detecting a target nucleic acid in a sample, the target being a nucleic acid of the present invention, the method comprising: a) hybridizing the sample with a probe comprising at least 30 contiguous nucleotides of a sequence complementary to the target nucleic acid in the sample under hybridization conditions sufficient to permit detectable binding of said probe to said target, and b) detecting the presence or absence, and optionally the amount, of said binding.

The invention also provides a fusion protein, the fusion protein comprising a polypeptide of the present invention fused to a heterologous amino acid sequence. In certain particularly useful embodiments, the heterologous amino acid sequence is a detectable moiety, such as a fluorescent moiety. In other embodiments, the heterologous amino acid sequence is an Ig Fc region.

In yet another aspect, the invention provides a method of screening for agents that modulate the expression of human hGDMLP-1, the method comprising: contacting a cell or tissue sample believed to express human hGDMLP-1 with a chemical or biological agent, and then comparing the amount of human hGDMLP-1 expression with that of a control.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which:

FIGS. 2A–2L collectively show the sequence of the cDNA encoding the human genome-derived myosin-like protein (hGDMLP-1) of the present invention (full-length cDNA (bases 1–8117)=SEQ ID NO:1; coding sequence (bases 170–7876)=SEQ ID NO:2), with its predicted amino acid sequence (SEQ ID NO:3);

FIGS. 3A–3C collectively show an alignment of residues 505–2249 of the hGDMLP-1 coding sequence of the present invention (SEQ ID NO:3) with the two closest known orthologues (BAA93660=SEQ ID NO:15753; BAA13206=SEQ ID NO:15754);

FIG. 4 shows an alignment of residues 1802–1907 of the amino acid sequence of hGDMLP-1 of the present invention (SEQ ID NO:3) and residues 82–180 of human myocilin (SEQ ID NO:15755);

FIG. 6 is a northern blot probed with a labeled fragment of hGDMLP-1, according to the present invention, showing muscle- and heart-specific expression of an 8 kb transcript corresponding to hGDMLP-1.

DETAILED DESCRIPTION OF THE INVENTION

Figure 1:
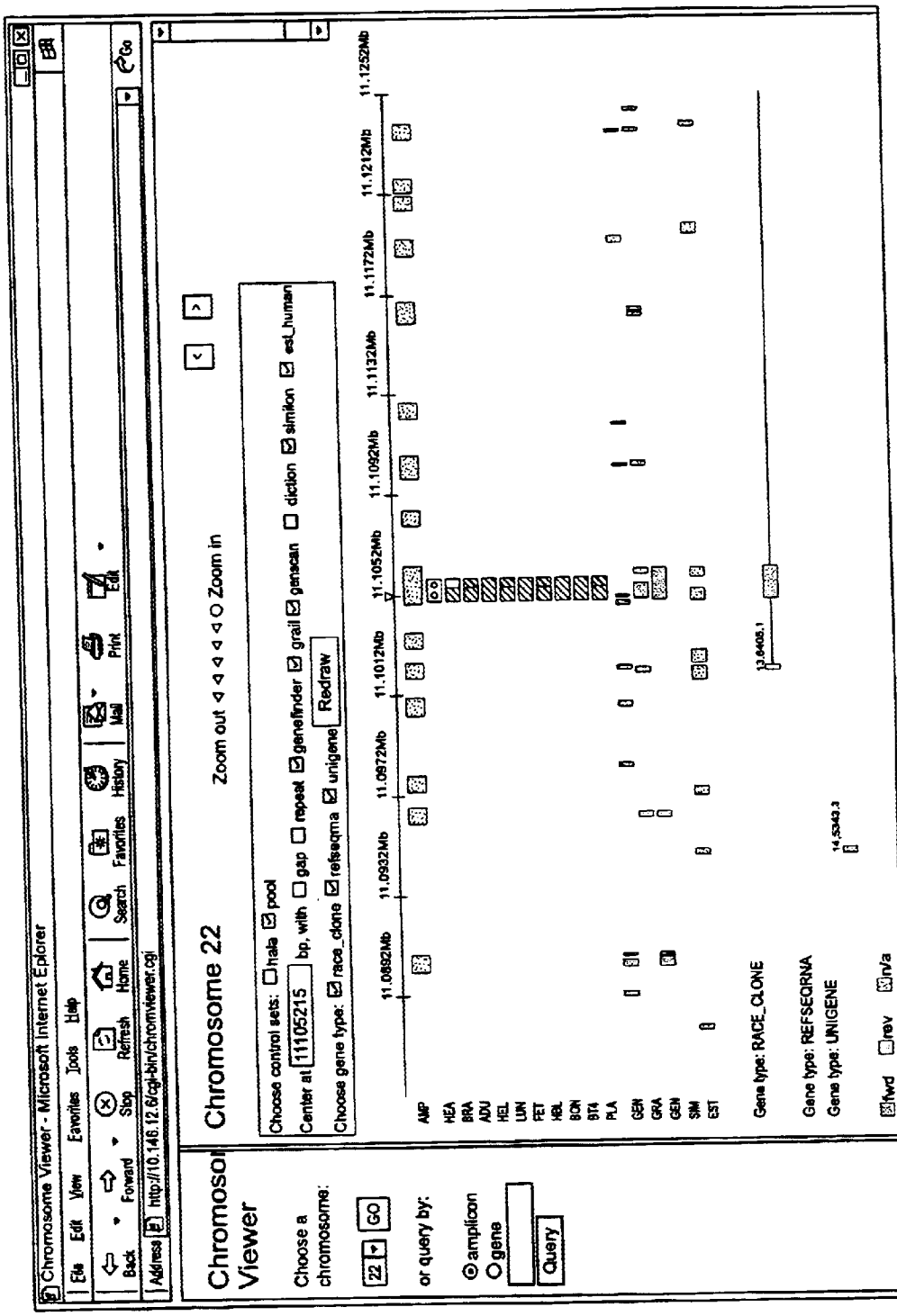
FIG. 1 is a screen shot of a graphical display that facilitates identification of exons in genomic sequence the expression of which meets user criteria, particularly identifying heart-specific expression of one exon of the gene of the present invention.

The present invention is based on the discovery of a new human myosin heavy chain-like protein, hGDMLP-1, the polynucleotides encoding hGDMLP-1, and the use of these compositions, inter alia, for the diagnosis, prevention, or treatment of disorders.

Definitions

Unless defined otherwise, all technical and scientific terms used herein have the meaning commonly understood by one of ordinary skill in the art to which this invention belongs. As used herein and in the appended claims, the singular forms "a", "an", and "the" include plural reference unless the context clearly dictates otherwise.

As used herein, "nucleic acid" (synonymously, "polynucleotide") includes polynucleotides having natural nucleotides in native 5'-3' phosphodiester linkage—e.g., DNA or RNA—as well as polynucleotides that have non-natural nucleotide analogues, nonnative internucleoside bonds, or both, so long as the nonnatural polynucleotide is capable of sequence-discriminating basepairing under experimentally desired conditions. Unless otherwise specified, the term "nucleic acid" includes any topological conformation; the term thus explicitly comprehends single-stranded, double-stranded, partially duplexed, triplexed, hairpinned, circular, and padlocked conformations.

As used herein, an "isolated nucleic acid" is a nucleic acid molecule that exists in a physical form that is nonidentical to any nucleic acid molecule of identical sequence as found in nature; "isolated" does not require, although it does not prohibit, that the nucleic acid so described has itself been physically removed from its native environment.

For example, a nucleic acid can be said to be "isolated" when it includes nucleotides and/or internucleoside bonds not found in nature. When instead composed of natural nucleosides in phosphodiester linkage, a nucleic acid can be said to be "isolated" when it exists at a purity not found in nature, where purity can be adjudged with respect to the presence of nucleic acids of other sequence, with respect to the presence of proteins, with respect to the presence of lipids, or with respect the presence of any other component of a biological cell, or when the nucleic acid lacks sequence that flanks an otherwise identical sequence in an organism's genome, or when the nucleic acid possesses sequence not identically present in nature.

As so defined, "isolated nucleic acid" includes nucleic acids integrated into a host cell chromosome at a heterologous site, recombinant fusions of a native fragment to a heterologous sequence, recombinant vectors present as episomes or as integrated into a host cell chromosome.

As used herein, an isolated nucleic acid "encodes" a reference polypeptide when at least a portion of the nucleic acid, or its complement, can be directly translated to provide the amino acid sequence of the reference polypeptide, or when the isolated nucleic acid can be used, alone or as part of an expression vector, to express the reference polypeptide in vitro, in a prokaryotic host cell, or in a eukaryotic host cell.

As used herein, the term "exon" refers to a nucleic acid sequence found in genomic DNA that is bioinformatically predicted and/or experimentally confirmed to contribute contiguous sequence to a mature mRNA transcript.

As used herein, the phrase "open reading frame" and the equivalent acronym "ORF" refer to that portion of a transcript-derived nucleic acid that can be translated in its entirety into a sequence of contiguous amino acids. As so defined, an ORF has length, measured in nucleotides, exactly divisible by 3. As so defined, an ORF need not encode the entirety of a natural protein.

As used herein, the phrase "ORF-encoded peptide" refers to the predicted or actual translation of an ORF.

As used herein, the phrase "degenerate variant" of a reference nucleic acid sequence intends all nucleic acid sequences that can be directly translated, using the standard genetic code, to provide an amino acid sequence identical to that translated from the reference nucleic acid sequence.

As used herein, the term "microarray" and the equivalent phrase "nucleic acid microarray" refer to a substrate-bound collection of plural nucleic acids, hybridization to each of the plurality of bound nucleic acids being separately detectable. The substrate can be solid or porous, planar or non-planar, unitary or distributed.

As so defined, the term "microarray" and phrase "nucleic acid microarray" include all the devices so called in Schena (ed.), *DNA Microarrays: A Practical Approach* (*Practical Approach Series*), Oxford University Press (1999) (ISBN: 0199637768); *Nature Genet.* 21(1)(suppl):1–60 (1999); and Schena (ed.), *Microarray Biochip: Tools and Technology*, Eaton Publishing Company/BioTechniques Books Division (2000) (ISBN: 1881299376), the disclosures of which are incorporated herein by reference in their entireties.

As so defined, the term "microarray" and phrase "nucleic acid microarray" include substrate-bound collections of plural nucleic acids in which the plurality of nucleic acids are distributably disposed on a plurality of beads, rather than on a unitary planar substrate, as is described, inter alia, in Brenner et al., *Proc. Natl. Acad. Sci. USA* 97(4):166501670 (2000), the disclosure of which is incorporated herein by reference in its entirety; in such case, the term "microarray" and phrase "nucleic acid microarray" refer to the plurality of beads in aggregate.

As used herein with respect to solution phase hybridization, the term "probe", or equivalently, "nucleic acid probe" or "hybridization probe", refers to an isolated nucleic acid of known sequence that is, or is intended to be, detectably labeled. As used herein with respect to a nucleic acid microarray, the term "probe" (or equivalently "nucleic acid probe" or "hybridization probe") refers to the isolated nucleic acid that is, or is intended to be, bound to the substrate. In either such context, the term "target" refers to nucleic acid intended to be bound to probe by sequence complementarity.

As used herein, the expression "probe comprising SEQ ID NO:X", and variants thereof, intends a nucleic acid probe, at least a portion of which probe has either (i) the sequence directly as given in the referenced SEQ ID NO:X, or (ii) a sequence complementary to the sequence as given in the referenced SEQ ID NO:X, the choice as between sequence directly as given and complement thereof dictated by the requirement that the probe be complementary to the desired target.

As used herein, the phrases "expression of a probe" and "expression of an isolated nucleic acid" and their linguistic equivalents intend that the probe (or, respectively, isolated nucleic acid), or a probe (or, respectively, isolated nucleic acid) complementary in sequence thereto, can hybridize detectably under high stringency conditions to a sample of nucleic acids that derive from mRNA transcripts from a given source. For example, and by way of illustration only, expression of a probe in "liver" means that the probe can hybridize detectably under high stringency conditions to a sample of nucleic acids that derive from mRNA obtained from liver.

As used herein, "a single exon probe" comprises at least part of an exon ("reference exon") and can hybridize detectably under high stringency conditions to transcript-derived nucleic acids that include the reference exon. The single exon probe will not, however, hybridize detectably under high stringency conditions to nucleic acids that lack the reference exon but include one or more exons that are found adjacent to the reference exon in the genome.

For purposes herein, "high stringency conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for at least 8 hours, followed by one or more washes in 0.2×SSC, 0.1% SDS at 65° C. "Moderate stringency conditions" are defined for solution phase hybridization as aqueous hybridization (i.e., free of formamide) in 6×SSC, 1% SDS at 65° C. for at least 8 hours, followed by one or more washes in 2×SSC, 0.1% SDS at room temperature.

For microarray-based hybridization, standard "high stringency conditions" are defined as hybridization in 50% formamide, 5×SSC, 0.2 $\mu g/\mu l$ poly(dA), 0.2 $\mu g/\mu l$ human cot1 DNA, and 0.5% SDS, in a humid oven at 42° C. overnight, followed by successive washes of the microarray in 1×SSC, 0.2% SDS at 55° C. for 5 minutes, and then 0.1×SSC, 0.2% SDS, at 55° C. for 20 minutes. For microarray-based hybridization, "moderate stringency conditions", suitable for cross-hybridization to mRNA encoding structurally- and functionally-related proteins, are defined to be the same as those for high stringency conditions but with reduction in temperature for hybridization and washing to room temperature (approximately 25° C.).

As used herein, the terms "protein", "polypeptide", and "peptide" are used interchangeably to refer to a naturally-occurring or synthetic polymer of amino acid monomers (residues), irrespective of length, where amino acid monomer here includes naturally-occurring amino acids, naturally-occurring amino acid structural variants, and synthetic non-naturally occurring analogs that are capable of participating in peptide bonds. The terms "protein", "polypeptide", and "peptide" explicitly permits of post-translational and post-synthetic modifications, such as glycosylation.

The term "oligopeptide" herein denotes a protein, polypeptide, or peptide having 25 or fewer monomeric subunits.

The phrases "isolated protein", "isolated polypeptide", "isolated peptide" and "isolated oligopeptidel" refer to a protein (or respectively to a polypeptide, peptide, or oligopeptide) that is nonidentical to any protein molecule of identical amino acid sequence as found in nature; "isolated" does not require, although it does not prohibit, that the protein so described has itself been physically removed from its native environment.

For example, a protein can be said to be "isolated" when it includes amino acid analogues or derivatives not found in nature, or includes linkages other than standard peptide bonds.

When instead composed entirely of natural amino acids linked by peptide bonds, a protein can be said to be "isolated" when it exists at a purity not found in nature—where purity can be adjudged with respect to the presence of proteins of other sequence, with respect to the presence of non-protein compounds, such as nucleic acids, lipids, or other components of a biological cell, or when it exists in a composition not found in nature, such as in a host cell that does not naturally express that protein.

A "purified protein" (equally, a purified polypeptide, peptide, or oligopeptide) is an isolated protein, as above described, present at a concentration of at least 95%, as measured on a mass basis with respect to total protein in a composition. A "substantially purified protein" (equally, a substantially purified polypeptide, peptide, or oligopeptide) is an isolated protein, as above described, present at a concentration of at least 70%, as measured on a mass basis with respect to total protein in a composition.

As used herein, the phrase "protein isoforms" refers to a plurality of proteins having nonidentical primary amino acid sequence but that share amino acid sequence encoded by at least one common exon.

As used herein, the phrase "alternative splicing" and its linguistic equivalents includes all types of RNA processing that lead to expression of plural protein isoforms from a single gene; accordingly, the phrase "splice variant(s)" and its linguistic equivalents embraces mRNAs transcribed from a given gene that, however processed, collectively encode plural protein isoforms. For example, and by way of illustration only, splice variants can include exon insertions, exon extensions, exon truncations, exon deletions, alternatives in the 5' untranslated region ("5' UT") and alternatives in the 3' untranslated region ("3' UT"). Such 31 alternatives include, for example, differences in the site of RNA transcript cleavage and site of poly(A) addition. See, e.g., Gautheret et al., Genome Res. 8:524–530 (1998).

As used herein, "orthologues" are separate occurrences of the same gene in multiple species. The separate occurrences have similar, albeit nonidentical, amino acid sequences, the degree of sequence similarity depending, in part, upon the evolutionary distance of the species from a common ancestor having the same gene.

As used herein, the term "paralogues" indicates separate occurrences of a gene in one species. The separate occurrences have similar, albeit nonidentical, amino acid sequences, the degree of sequence similarity depending, in part, upon the evolutionary distance from the gene duplication event giving rise to the separate occurrences.

As used herein, the term "homologues" is generic to "orthologues" and "paralogues".

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives.

Fragments within the scope of the term "antibody" include those produced by digestion with various proteases, those produced by chemical cleavage and/or chemical dissociation, and those produced recombinantly, so long as the fragment remains capable of specific binding to a target molecule. Among such fragments are Fab, Fab', Fv, F(ab)'$_2$ and single chain Fv (scFv) fragments.

Derivatives within the scope of the term "antibody" include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., Marasco (ed.), *Intracellular Antibodies: Research and Disease Applications*, Springer-Verlag New York, Inc. (1998) (ISBN: 3540641513), the disclosure of which is incorporated herein by reference in its entirety).

As used herein, "antigen" refers to a ligand that can be bound by an antibody; an antigen need not itself be immunogenic. The portions of the antigen that make contact with the antibody are denominated "epitopes".

"Specific binding" refers to the ability of two molecular species concurrently present in a heterogeneous (inhomogeneous) sample to bind to one another in preference to binding to other molecular species in the sample. Typically, a specific binding interaction will discriminate over adventitious binding interactions in the reaction by at least two-fold, more typically by at least 10-fold, often at least 100-fold; when used to detect analyte, specific binding is sufficiently discriminatory when determinative of the presence of the analyte in a heterogeneous (inhomogeneous) sample. Typically, the affinity or avidity of a specific binding reaction is least about $10^{-7}$ M, with specific binding reactions of greater specificity typically having affinity or avidity of at least $10^{-8}$ M to at least about $10^{-9}$ M.

As used herein, "molecular binding partners"—and equivalently, "specific binding partners"—refer to pairs of molecules, typically pairs of biomolecules, that exhibit specific binding. Nonlimiting examples are receptor and ligand, antibody and antigen, and biotin to any of avidin, streptavidin, neutrAvidin and captAvidin.

Unless made otherwise clear by context, "hGDMLP-1" as used herein includes both human hGDMLP-1 and orthologues from other species. Particularly useful orthologues are those from other primate species, such as chimpanzee, rhesus macaque monkey, baboon, orangutan, and gorilla; from rodents, such as rats, mice, guinea pigs; from lagomorphs, such as rabbits, and from domestic livestock, such as cow, pig, sheep, horse, goat.

The term "agonist", as used herein, refers to a molecule which, when bound to hGDMLP-1, increases or prolongs the duration of the effect of hGDMLP-1, or stimulates the function of hGDMLP-1. Conversely, an "antagonist", as used herein, refers to a molecule which, when bound to hGDMLP-1, decreases the amount or the duration of the effect of the biological or immunological activity of hGDMLP-1, or reduces the function of hGDMLP-1.

The term "antisense", as used herein, refers to a nucleic acid molecule sufficiently complementary in sequence and sufficiently long in complementary sequence as to hybridize under intracellular conditions to (i) a target mRNA transcript or (ii) the genomic DNA strand complementary to that transcribed to produce the target mRNA transcript.

A "biologically active" hGDMLP-1 protein, derivative, or fragment thereof has at least one measurable biological, biochemical, structural, or regulatory activity of hGDMLP-1. An "immunologically active" hGDMLP-1 protein, derivative, or fragment thereof is able to induce a specific cellular or humoral immune response to the immunizing protein, derivative, or fragment; although preferred, it is not required that the response be cross-reactive with native hGDMLP-1.

An agent is said to "modulate" the activity of hGDMLP-1 protein when it measurably changes at least one biological or immunological activity of hGDMLP-1; such change can, but need not, be effected by change in the amount of hGDMLP-1 present in a cell.

A "consensus sequence", as used herein, is a nucleic acid sequence that has been formulated by any or all of (i) resequencing to resolve uncalled bases, (ii) extension (e.g. by RACE or anchored PCR), or (iii) assembly from overlapping sequences of more than one clone.

The term "portion", as used with respect to nucleic acids, proteins, and antibodies, is synonymous with "fragment".

A "variant" of hGDMLP-1, as used herein, refers to a protein having a sequence that is altered from hGDMLP-1 by one or more amino acids. The term includes proteins having conservative or moderately conservative replacements, amino acid deletions, amino acid insertions, or combinations thereof. Guidance in determining which amino acid residues can be substituted, inserted, or deleted without abolishing biological or immunological activity is set forth herein below.

Nucleic Acid Molecules

In a first aspect, the invention provides isolated nucleic acids that encode hGDMLP-1, variants having at least 65% sequence identity thereto, degenerate variants thereof, variants that encode hGDMLP-1 proteins having conservative or moderately conservative substitutions, cross-hybridizing nucleic acids, and fragments thereof.

FIG. 2 presents the nucleotide sequence of the hGDMLP-1 cDNA clone, with predicted amino acid translation; the sequences are further presented in the Sequence Listing, incorporated herein by reference in its entirety, as follows:

| | |
|---|---|
| SEQ ID NO: 1 | (nt; full length cDNA) |
| SEQ ID NO: 2 | (nt; cDNA ORF) |
| SEQ ID NO: 3 | (aa; full length protein) |
| SEQ ID NO: 4 | (nt; cDNA nt 1–2953) |
| SEQ ID NO: 5 | (nt; cDNA nt 3175–end) |
| SEQ ID NOs: 6–2,942 | (nt; 17-mers scanning SEQ ID NO: 4) |
| SEQ ID NOs: 2,943–5,871 | (nt; 25-mers scanning SEQ ID NO: 4) |
| SEQ ID NOs: 5,872–10,771 | (nt; 17-mers scanning SEQ ID NO: 5) |
| SEQ ID NOs: 10,772–15,663 | (nt; 25-mers scanning SEQ ID NO: 5) |
| SEQ ID NOs: 15,664–15,707 | (nt; exons) |
| SEQ ID NOs: 15,708–15,751 | (nt; amplicons) |
| SEQ ID NO: 15,752 | (nt; putative promoter sequence) |

Unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

Unless otherwise indicated, nucleotide sequences of the isolated nucleic acids of the present invention were determined by sequencing a DNA molecule that had resulted, directly or indirectly, from at least one enzymatic polymerization reaction (e.g., reverse transcription and/or polymerase chain reaction) using an automated sequencer (such as the MegaBACE™ 1000, Molecular Dynamics, Sunnyvale, Calif., USA), or by reliance upon such sequence or upon genomic sequence prior-accessioned into a public database. Unless otherwise indicated, all amino acid sequences of the polypeptides of the present invention were predicted by translation from the nucleic acid sequences so determined.

As a consequence, any nucleic acid sequence presented herein may contain errors introduced by erroneous incorporation of nucleotides during polymerization, by erroneous base calling by the automated sequencer (although such sequencing errors have been minimized for the nucleic acids directly determined herein, unless otherwise indicated, by the sequencing of each of the complementary strands of a duplex DNA), or by similar errors accessioned into the public database.

Accordingly, the hGDMLP-1 cDNA clone described herein has been deposited in a public repository (American Type Culture Collection, Manassas, Va., USA). The deposit, made according to the Budapest Treat on the International Recognition of the Deposit of Microorganisms for the Purposes of Patent Procedure, was received at ATCC on May 23, 2001 and given an accession number of PTA-3397. Any errors in sequence reported herein can be determined and corrected by sequencing nucleic acids propagated from the deposited clones using standard techniques.

Single nucleotide polymorphisms (SNPs) occur frequently in eukaryotic genomes—more than 1.4 million SNPs have already identified in the human genome, International Human Genome Sequencing Consortium, *Nature* 409:860–921 (2001)—and the sequence determined from one individual of a species may differ from other allelic forms present within the population. Additionally, small deletions and insertions, rather than single nucleotide polymorphisms, are not uncommon in the general population, and often do not alter the function of the protein.

Accordingly, it is an aspect of the present invention to provide nucleic acids not only identical in sequence to those described with particularity herein, but also to provide isolated nucleic acids at least about 65% identical in sequence to those described with particularity herein, typically at least about 70%, 75%, 80%, 85%, or 90% identical in sequence to those described with particularity herein, usefully at least about 91%, 92%, 93%, 94%, or 95% identical in sequence to those described with particularity herein, usefully at least about 96%, 97%, 98%, or 99% identical in sequence to those described with particularity herein, and, most conservatively, at least about 99.5%, 99.6%, 99.7%, 99.8% and 99.9% identical in sequence to those described with particularity herein. These sequence variants can be naturally occurring or can result from human intervention, as by random or directed mutagenesis.

For purposes herein, percent identity of two nucleic acid sequences is determined using the procedure of Tatiana et al., "Blast 2 sequences—a new tool for comparing protein and nucleotide sequences", FEMS Microbiol Lett. 174:247–250(1999), which procedure is effectuated by the computer program BLAST 2 SEQUENCES, available online at the National Center for Biotechnology Information (NCBI) website. To assess percent identity of nucleic acids, the BLASTN module of BLAST 2 SEQUENCES is used with default values of (i) reward for a match: 1; (ii) penalty for a mismatch: −2; (iii) open gap 5 and extension gap 2 penalties; (iv) gap X_dropoff 50 expect 10 word size 11 filter, and both sequences are entered in their entireties.

As is well known, the genetic code is degenerate, with each amino acid except methionine translated from a plurality of codons, thus permitting a plurality of nucleic acids of disparate sequence to encode the identical protein. As is also well known, codon choice for optimal expression varies from species to species. The isolated nucleic acids of the present invention being useful for expression of hGDMLP-1 proteins and protein fragments, it is, therefore, another aspect of the present invention to provide isolated nucleic acids that encode hGDMLP-1 proteins and portions thereof not only identical in sequence to those described with particularity herein, but degenerate variants thereof as well.

As is also well known, amino acid substitutions occur frequently among natural allelic variants, with conservative substitutions often occasioning only de minimis change in protein function.

Accordingly, it is an aspect of the present invention to provide nucleic acids not only identical in sequence to those described with particularity herein, but also to provide isolated nucleic acids that encode hGDMLP-1, and portions thereof, having conservative amino acid substitutions, and also to provide isolated nucleic acids that encode hGDMLP-1, and portions thereof, having moderately conservative amino acid substitutions.

Although there are a variety of metrics for calling conservative amino acid substitutions, based primarily on either observed changes among evolutionarily related proteins or on predicted chemical similarity, for purposes herein a conservative replacement is any change having a positive value in the PAM250 log-likelihood matrix reproduced herein below (see Gonnet et al., *Science* 256(5062):1443–5 (1992)):

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 2 | −1 | 0 | 0 | 0 | 0 | 0 | 0 | −1 | −1 | −1 | 0 | −1 | −2 | 0 | 1 | 1 | −4 | −2 | 0 |
| R | −1 | 5 | 0 | 0 | −2 | 2 | 0 | −1 | 1 | −2 | −2 | 3 | −2 | −3 | −1 | 0 | 0 | −2 | −2 | −2 |
| N | 0 | 0 | 4 | 2 | −2 | 1 | 1 | 0 | 1 | −3 | −3 | 1 | −2 | −3 | −1 | 1 | 0 | −4 | −1 | −2 |
| D | 0 | 0 | 2 | 5 | −3 | 1 | 3 | 0 | 0 | −4 | −4 | 0 | −3 | −4 | −1 | 0 | 0 | −5 | −3 | −3 |
| C | 0 | −2 | −2 | −3 | 12 | −2 | −3 | −2 | −1 | −1 | −2 | −3 | −1 | −1 | −3 | 0 | 0 | −1 | 0 | 0 |
| Q | 0 | 2 | 1 | 1 | −2 | 3 | 2 | −1 | 1 | −2 | −2 | 2 | −1 | −3 | 0 | 0 | 0 | −3 | −2 | −2 |
| E | 0 | 0 | 1 | 3 | −3 | 2 | 4 | −1 | 0 | −3 | −3 | 1 | −2 | −4 | 0 | 0 | 0 | −4 | −3 | −2 |
| G | 0 | −1 | 0 | 0 | −2 | −1 | −1 | 7 | −1 | −4 | −4 | −1 | −4 | −5 | −2 | 0 | −1 | −4 | −4 | −3 |
| H | −1 | 1 | 1 | 0 | −1 | 1 | 0 | −1 | 6 | −2 | −2 | 1 | −1 | 0 | −1 | 0 | 0 | −1 | 2 | −2 |
| I | −1 | −2 | −3 | −4 | −1 | −2 | −3 | −4 | −2 | 4 | 3 | −2 | 2 | 1 | −3 | −2 | −1 | −2 | −1 | 3 |
| L | −1 | −2 | −3 | −4 | −2 | −2 | −3 | −4 | −2 | 3 | 4 | −2 | 3 | 2 | −2 | −2 | −1 | −1 | 0 | 2 |

-continued

|   | A  | R  | N  | D  | C  | Q  | E  | G  | H  | I  | L  | K  | M  | F  | P  | S  | T  | W  | Y  | V  |
|---|----|----|----|----|----|----|----|----|----|----|----|----|----|----|----|----|----|----|----|----|
| K | 0  | 3  | 1  | 0  | -3 | 2  | 1  | -1 | 1  | -2 | -2 | 3  | -1 | -3 | -1 | 0  | 0  | -4 | -2 | -2 |
| M | -1 | -2 | -2 | -3 | -1 | -1 | -2 | -4 | -1 | 2  | 3  | -1 | 4  | 2  | -2 | -1 | -1 | -1 | 0  | 2  |
| F | -2 | -3 | -3 | -4 | -1 | -3 | -4 | -5 | 0  | 1  | 2  | -3 | 2  | 7  | -4 | -3 | -2 | 4  | 5  | 0  |
| P | 0  | -1 | -1 | -1 | -3 | 0  | 0  | -2 | -1 | -3 | -2 | -1 | -2 | -4 | 8  | 0  | 0  | -5 | -3 | -2 |
| S | 1  | 0  | 1  | 0  | 0  | 0  | 0  | 0  | 0  | -2 | -2 | 0  | -1 | -3 | 0  | 2  | 2  | -3 | -2 | -1 |
| T | 1  | 0  | 0  | 0  | 0  | 0  | 0  | -1 | 0  | -1 | -1 | 0  | -1 | -2 | 0  | 2  | 2  | -4 | -2 | 0  |
| W | -4 | -2 | -4 | -5 | -1 | -3 | -4 | -4 | -1 | -2 | -1 | -4 | -1 | 4  | -5 | -3 | -4 | 14 | 4  | -3 |
| Y | -2 | -2 | -1 | -3 | 0  | -2 | -3 | -4 | 2  | -1 | 0  | -2 | 0  | 5  | -3 | -2 | -2 | 4  | 8  | -1 |
| V | 0  | -2 | -2 | -3 | 0  | -2 | -2 | -3 | -2 | 3  | 2  | -2 | 2  | 0  | -2 | -1 | 0  | -3 | -1 | 3  |

For purposes herein, a "moderately conservative" replacement is any change having a nonnegative value in the PAM250 log-likelihood matrix reproduced herein above.

As is also well known in the art, relatedness of nucleic acids can also be characterized using a functional test, the ability of the two nucleic acids to base-pair to one another at defined hybridization stringencies.

It is, therefore, another aspect of the invention to provide isolated nucleic acids not only identical in sequence to those described with particularity herein, but also to provide isolated nucleic acids ("cross-hybridizing nucleic acids") that hybridize under high stringency conditions (as defined herein) to all or to a portion of various of the isolated hGDMLP-1 nucleic acids of the present invention ("reference nucleic acids"), as well as cross-hybridizing nucleic acids that hybridize under moderate stringency conditions to all or to a portion of various of the isolated hGDMLP-1 nucleic acids of the present invention.

Such cross-hybridizing nucleic acids are useful, inter alia, as probes for, and to drive expression of, proteins related to the proteins of the present invention as alternative isoforms, homologues, paralogues, and orthologues. Particularly preferred orthologues are those from other primate species, such as chimpanzee, rhesus macaque, baboon, and gorilla, from rodents, such as rats, mice, guinea pigs, and from livestock, such as cow, pig, sheep, horse, goat.

The hybridizing portion of the reference nucleic acid is typically at least 15 nucleotides in length, often at least 17 nucleotides in length. Often, however, the hybridizing portion of the reference nucleic acid is at least 20 nucleotides in length, 25 nucleotides in length, and even 30 nucleotides, 35 nucleotides, 40 nucleotides, and 50 nucleotides in length. Of course, cross-hybridizing nucleic acids that hybridize to a larger portion of the reference nucleic acid—for example, to a portion of at least 50 nt, at least 100 nt, at least 150 nt, 200 nt, 250 nt, 300 nt, 350 nt, 400 nt, 450 nt, or 500 nt or more—or even to the entire length of the reference nucleic acid, are also useful.

The hybridizing portion of the cross-hybridizing nucleic acid is at least 75% identical in sequence to at least a portion of the reference nucleic acid. Typically, the hybridizing portion of the cross-hybridizing nucleic acid is at least 80%, often at least 85%, 86%, 87%, 88%, 89% or even at least 90% identical in sequence to at least a portion of the reference nucleic acid. Often, the hybridizing portion of the cross-hybridizing nucleic acid will be at least 91%, 92%, 93%, 94%, 95%, 96%, 97%, 98%, or 99% identical in sequence to at least a portion of the reference nucleic acid sequence. At times, the hybridizing portion of the cross-hybridizing nucleic acid will be at least 99.5% identical in sequence to at least a portion of the reference nucleic acid.

The invention also provides fragments of various of the isolated nucleic acids of the present invention.

By "fragments" of a reference nucleic acid is here intended isolated nucleic acids, however obtained, that have a nucleotide sequence identical to a portion of the reference nucleic acid sequence, which portion is at least 17 nucleotides and less than the entirety of the reference nucleic acid. As so defined, "fragments" need not be obtained by physical fragmentation of the reference nucleic acid, although such provenance is not thereby precluded.

In theory, an oligonucleotide of 17 nucleotides is of sufficient length as to occur at random less frequently than once in the three gigabase human genome, and thus to provide a nucleic acid probe that can uniquely identify the reference sequence in a nucleic acid mixture of genomic complexity. As is well known, further specificity can be obtained by probing nucleic acid samples of subgenomic complexity, and/or by using plural fragments as short as 17 nucleotides in length collectively to prime amplification of nucleic acids, as, e.g., by polymerase chain reaction (PCR).

As further described herein below, nucleic acid fragments that encode at least 6 contiguous amino acids (i.e., fragments of 18 nucleotides or more) are useful in directing the expression or the synthesis of peptides that have utility in mapping the epitopes of the protein encoded by the reference nucleic acid. See, e.g., Geysen et al., "Use of peptide synthesis to probe viral antigens for epitopes to a resolution of a single amino acid," *Proc. Natl. Acad. Sci. USA* 81:3998–4002 (1984); and U.S. Pat. Nos. 4,708,871 and 5,595,915, the disclosures of which are incorporated herein by reference in their entireties.

As further described herein below, fragments that encode at least 8 contiguous amino acids (i.e., fragments of 24 nucleotides or more) are useful in directing the expression or the synthesis of peptides that have utility as immunogens. See, e.g., Lerner, "Tapping the immunological repertoire to produce antibodies of predetermined specificity," Nature 299:592–596 (1982); Shinnick et al., "Synthetic peptide immunogens as vaccines," *Annu. Rev. Microbiol.* 37:425–46 (1983); Sutcliffe et al., "Antibodies that react with predetermined sites on proteins," Science 219:660–6 (1983), the disclosures of which are incorporated herein by reference in their entireties.

The nucleic acid fragment of the present invention is thus at least 17 nucleotides in length, typically at least 18 nucleotides in length, and often at least 24 nucleotides in length. Often, the nucleic acid of the present invention is at least 25 nucleotides in length, and even 30 nucleotides, 35 nucleotides, 40 nucleotides, or 45 nucleotides in length. Of course, larger fragments having at least 50 nt, at least 100 nt, at least 150 nt, 200 nt, 250 nt, 300 nt, 350 nt, 400 nt, 450 nt, or 500 nt or more are also useful, and at times preferred.

Having been based upon the mining of genomic sequence, rather than upon surveillance of expressed message, the present invention further provides isolated genome-derived nucleic acids that include portions of the hGDMLP-1 gene.

The invention particularly provides genome-derived single exon probes.

As further described in commonly owned and copending U.S. patent application Ser. No. 09/774,203, filed Jan. 29, 2001 and Ser. No. 09/632,366, filed Aug. 3, 2000, and provisional U.S. patent application No. 60/236,359, filed May 26, 2000 and No. 60/236,359, filed Sep. 27, 2000, the disclosures of which are incorporated herein by reference in their entireties, "a single exon probe" comprises at least part of an exon ("reference exon") and can hybridize detectably under high stringency conditions to transcript-derived nucleic acids that include the reference exon. The single exon probe will not, however, hybridize detectably under high stringency conditions to nucleic acids that lack the reference exon but include one or more exons that are found adjacent to the reference exon in the genome.

Genome-derived single exon probes typically further comprise, contiguous to a first end of the reference exon portion, a first intronic and/or intergenic sequence that is identically contiguous to the exon in the genome. Often, the genome-derived single exon probe further comprises, contiguous to a second end of the exonic portion, a second intronic and/or intergenic sequence that is identically contiguous to the exon in the genome.

The minimum length of genome-derived single exon probes is defined by the requirement that the exonic portion be of sufficient length to hybridize under high stringency conditions to transcript-derived nucleic acids. Accordingly, the exon portion is at least 17 nucleotides, typically at least 18 nucleotides, 20 nucleotides, 24 nucleotides, 25 nucleotides or even 30, 35, 40, 45, or 50 nucleotides in length, and can usefully include the entirety of the exon, up to 100 nt, 150 nt, 200 nt, 250 nt, 300 nt, 350 nt, 400 nt or even 500 nt or more in length.

The maximum length of genome-derived single exon probes is defined by the requirement that the probes contain portions of no more than one exon, that is, be unable to hybridize detectably under high stringency conditions to nucleic acids that lack the reference exon but include one or more exons that are found adjacent to the reference exon in the genome.

Given variable spacing of exons through eukaryotic genomes, the maximum length of the single exon probes of the present invention is typically no more than 25 kb, often no more than 20 kb, 15 kb, 10 kb or 7.5 kb, or even no more than 5 kb, 4 kb, 3 kb, or even no more than about 2.5 kb in length.

The genome-derived single exon probes of the present invention can usefully include at least a first terminal priming sequence not found in contiguity with the rest of the probe sequence in the genome, and often will contain a second terminal priming sequence not found in contiguity with the rest of the probe sequence in the genome.

The present invention also provides isolated genome-derived nucleic acids that include nucleic acid sequence elements that control transcription of the hGDMLP-1 gene.

With a complete draft of the human genome now available, genomic sequences that are within the vicinity of the hGDMLP-1 gene (and that are additional to those described with particularity herein) can readily be obtained by PCR amplification.

The isolated nucleic acids of the present invention can be composed of natural nucleotides in native 5'-3' phosphodiester internucleoside linkage—e.g., DNA or RNA—or can contain any or all of nonnatural nucleotide analogues, non-native internucleoside bonds, or post-synthesis modifications, either throughout the length of the nucleic acid or localized to one or more portions thereof. As is well known in the art, when the isolated nucleic acid is used as a hybridization probe, the range of such nonnatural analogues, nonnative internucleoside bonds, or post-synthesis modifications will be limited to those that permit sequence-discriminating basepairing of the resulting nucleic acid. When used to direct expression or RNA or protein in vitro or in vivo, the range of such nonnatural analogues, nonnative internucleoside bonds, or post-synthesis modifications will be limited to those that permit the nucleic acid to function properly as a polymerization substrate. When the isolated nucleic acid is used as a therapeutic agent, the range of such changes will be limited to those that do not confer toxicity upon the isolated nucleic acid.

For example, when desired to be used as probes, the isolated nucleic acids of the present invention can usefully include nucleotide analogues that incorporate labels that are directly detectable, such as radiolabels or fluorophores, or nucleotide analogues that incorporate labels that can be visualized in a subsequent reaction, such as biotin or various haptens.

Common radiolabeled analogues include those labeled with $^{33}$P, $^{32}$P, and $^{35}$S, such as $\alpha$-$^{32}$P-dATP, $\alpha$-$^{32}$P-dCTP, $\alpha$-$^{32}$P-dGTP, $\alpha$-$^{32}$P-dTTP, $\alpha$-$^{32}$P-3'dATP, $\alpha$-$^{32}$P-ATP, $\alpha$-$^{32}$P-CTP, $\alpha$-$^{32}$P-GTP, $\alpha$-$^{32}$P-UTP, $\alpha$-$^{35}$S-DATP, $\gamma$-$^{35}$S-GTP, $\gamma$-$^{33}$P-dATP, and the like.

Commercially available fluorescent nucleotide analogues readily incorporated into the nucleic acids of the present invention include Cy3-dCTP, Cy3-dUTP, Cy5-dCTP, Cy3-dUTP (Amersham Pharmacia Biotech, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY® TMR-14-dUTP, BODIPY® TR-14-dUTP, Rhodamine Green™-5-dUTP, Oregon Green® 488-5-dUTP, Texas Red®-12-dUTP, BODIPYO 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPYO TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA).

Protocols are available for custom synthesis of nucleotides having other fluorophores. Henegariu et al., "Custom Fluorescent-Nucleotide Synthesis as an Alternative Method for Nucleic Acid Labeling," *Nature Biotechnol.* 18:345-348 (2000), the disclosure of which is incorporated herein by reference in its entirety.

Haptens that are commonly conjugated to nucleotides for subsequent labeling include biotin (biotin-11-dUTP, Molecular Probes, Inc., Eugene, Oreg., USA; biotin-21-UTP, biotin-21-dUTP, Clontech Laboratories, Inc., Palo Alto, Calif., USA), digoxigenin (DIG-11-dUTP, alkali labile, DIG-11-UTP, Roche Diagnostics Corp., Indianapolis, Ind., USA), and dinitrophenyl (dinitrophenyl-11-dUTP, Molecular Probes, Inc., Eugene, Oreg., USA).

As another example, when desired to be used for antisense inhibition of transcription or translation, the isolated nucleic acids of the present invention can usefully include altered, often nuclease-resistant, internucleoside bonds. See Hartmann et al. (eds.), *Manual of Antisense Methodology* (Perspectives in Antisense Science), Kluwer Law International (1999) (ISBN:079238539X); Stein et al. (eds.), *Applied Antisense Oligonucleotide Technology*, Wiley-Liss (cover (1998) (ISBN: 0471172790); Chadwick et al. (eds.), *Oligonucleotides as Therapeutic Agents—Symposium No. 209*, John Wiley & Son Ltd (1997) (ISBN: 0471972797), the disclosures of which are incorporated herein by reference in their entireties. Such altered internucloside bonds are often desired also when the isolated nucleic acid of the present invention is to be used for targeted gene correction, Gamper et al., *Nucl. Acids Res.* 28(21):4332–9 (2000), the disclosure of which is incorporated herein by reference in its entirety.

Modified oligonucleotide backbones often preferred when the nucleic acid is to be used for antisense purposes are, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, the disclosures of which are incorporated herein by reference in their entireties.

Preferred modified oligonucleotide backbones for antisense use that do not include a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above backbones include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, the disclosures of which are incorporated herein by reference in their entireties.

In other preferred oligonucleotide mimetics, both the sugar and the internucleoside linkage are replaced with novel groups, such as peptide nucleic acids (PNA).

In PNA compounds, the phosphodiester backbone of the nucleic acid is replaced with an amide-containing backbone, in particular by repeating N-(2-aminoethyl) glycine units linked by amide bonds. Nucleobases are bound directly or indirectly to aza nitrogen atoms of the amide portion of the backbone, typically by methylene carbonyl linkages.

The uncharged nature of the PNA backbone provides PNA/DNA and PNA/RNA duplexes with a higher thermal stability than is found in DNA/DNA and DNA/RNA duplexes, resulting from the lack of charge repulsion between the PNA and DNA or RNA strand. In general, the Tm of a PNA/DNA or PNA/RNA duplex is 1° C. higher per base pair than the Tm of the corresponding DNA/DNA or DNA/RNA duplex (in 100 mM NaCl).

The neutral backbone also allows PNA to form stable DNA duplexes largely independent of salt concentration. At low ionic strength, PNA can be hybridized to a target sequence at temperatures that make DNA hybridization problematic or impossible. And unlike DNA/DNA duplex formation, PNA hybridization is possible in the absence of magnesium. Adjusting the ionic strength, therefore, is useful if competing DNA or RNA is present in the sample, or if the nucleic acid being probed contains a high level of secondary structure.

PNA also demonstrates greater specificity in binding to complementary DNA. A PNA/DNA mismatch is more destabilizing than DNA/DNA mismatch. A single mismatch in mixed a PNA/DNA 15-mer lowers the Tm by 8–20° C. (15° C. on average). In the corresponding DNA/DNA duplexes, a single mismatch lowers the Tm by 4–16° C. (11° C. on average). Because PNA probes can be significantly shorter than DNA probes, their specificity is greater.

Additionally, nucleases and proteases do not recognize the PNA polyamide backbone with nucleobase sidechains. As a result, PNA oligomers are resistant to degradation by enzymes, and the lifetime of these compounds is extended both in vivo and in vitro. In addition, PNA is stable over a wide pH range.

Because its backbone is formed from amide bonds, PNA can be synthesized using a modified peptide synthesis protocol. PNA oligomers can be synthesized by both Fmoc and tBoc methods. Representative U.S. patents that teach the preparation of PNA compounds include, but are not limited to, U.S. Pat. Nos. 5,539,082; 5,714,331; and 5,719,262, each of which is herein incorporated by reference; automated PNA synthesis is readily achievable on commercial synthesizers (see, e.g., "PNA User's Guide," Rev. 2, February 1998, Perseptive Biosystems Part No. 60138, Applied Biosystems, Inc., Foster City, Calif.).

PNA chemistry and applications are reviewed, inter alia, in Ray et al., *FASEB J.* 14(9):1041–60 (2000); Nielsen et al., *Pharmacol Toxicol.* 86(1):3–7 (2000); Larsen et al., *Biochim Biophys Acta.* 1489(1):159–66 (1999); Nielsen, *Curr. Opin. Struct. Biol.* 9(3):353–7 (1999), and Nielsen, *Curr. Opin. Biotechnol.* 10(1):71–5 (1999), the disclosures of which are incorporated herein by reference in their entireties.

Differences from nucleic acid compositions found in nature—e.g., nonnative bases, altered internucleoside linkages, post-synthesis modification—can be present throughout the length of the nucleic acid or can, instead, usefully be localized to discrete portions thereof. As an example of the latter, chimeric nucleic acids can be synthesized that have discrete DNA and RNA domains and demonstrated utility for targeted gene repair, as further described in U.S. Pat. Nos. 5,760,012 and 5,731,181, the disclosures of which are incorporated herein by reference in their entireties. As another example, chimeric nucleic acids comprising both DNA and PNA have been demonstrated to have utility in modified PCR reactions. See Misra et al., *Biochem.* 37: 1917–1925 (1998); see also Finn et al., *Nucl. Acids Res.* 24: 3357–3363 (1996), incorporated herein by reference.

Unless otherwise specified, nucleic acids of the present invention can include any topological conformation appropriate to the desired use; the term thus explicitly comprehends, among others, single-stranded, double-stranded, triplexed, quadruplexed, partially double-stranded, partially-triplexed, partially-quadruplexed, branched, hairpinned, circular, and padlocked conformations. Padlock conformations and their utilities are further described in Banèr et al., *Curr. Opin. Biotechnol.* 12:11–15 (2001); Escude et al., Proc. Natl. Acad. Sci. USA 14;96(19):10603–7 (1999); Nilsson et al., *Science* 265(5181):2085–8 (1994), the disclosures of which are incorporated herein by reference in their entireties. Triplex and quadruplex conformations, and their utilities, are reviewed in Praseuth et al., *Biochim. Biophys. Acta.* 1489(1):181–206 (1999); Fox, *Curr. Med. Chem.* 7(1):17–37 (2000); Kochetkova et al., *Methods Mol. Biol.* 130:189–201 (2000); Chan et al., *J. Mol. Med.* 75(4): 267–82 (1997), the disclosures of which are incorporated herein by reference in their entireties.

The nucleic acids of the present invention can be detectably labeled.

Commonly-used labels include radionuclides, such as $^{32}$P, $^{33}$P, $^{35}$S, $^{3}$H (and for NMR detection, $^{13}$C and $^{15}$N), haptens that can be detected by specific antibody or high affinity binding partner (such as avidin), and fluorophores.

As noted above, detectable labels can be incorporated by inclusion of labeled nucleotide analogues in the nucleic acid. Such analogues can be incorporated by enzymatic polymerization, such as by nick translation, random priming, polymerase chain reaction (PCR), terminal transferase tailing, and end-filling of overhangs, for DNA molecules, and in vitro transcription driven, e.g., from phage promoters, such as T7, T3, and SP6, for RNA molecules. Commercial kits are readily available for each such labeling approach.

Analogues can also be incorporated during automated solid phase chemical synthesis.

As is well known, labels can also be incorporated after nucleic acid synthesis, with the 5' phosphate and 3' hydroxyl providing convenient sites for post-synthetic covalent attachment of detectable labels.

Various other post-synthetic approaches permit internal labeling of nucleic acids.

For example, fluorophores can be attached using a cisplatin reagent that reacts with the N7 of guanine residues (and, to a lesser extent, adenine bases) in DNA, RNA, and PNA to provide a stable coordination complex between the nucleic acid and fluorophore label (Universal Linkage System) (available from Molecular Probes, Inc., Eugene, Oreg., USA and Amersham Pharmacia Biotech, Piscataway, N.J., USA); see Alers et al., *Genes, Chromosomes & Cancer*, Vol. 25, pp. 301–305 (1999); Jelsma et al., *J. NIH Res.* 5:82 (1994); Van Belkum et al., *BioTechniques* 16:148–153 (1994), incorporated herein by reference. As another example, nucleic acids can be labeled using a disulfide-containing linker (FastTag™ Reagent, Vector Laboratories, Inc., Burlingame, Calif., USA) that is photo- or thermally coupled to the target nucleic acid using aryl azide chemistry; after reduction, a free thiol is available for coupling to a hapten, fluorophore, sugar, affinity ligand, or other marker.

Multiple independent or interacting labels can be incorporated into the nucleic acids of the present invention.

For example, both a fluorophore and a moiety that in proximity thereto acts to quench fluorescence can be included to report specific hybridization through release of fluorescence quenching, Tyagi et al., *Nature Biotechnol.* 14: 303–308 (1996); Tyagi et al., *Nature Biotechnol.* 16, 49–53 (1998); Sokol et al., *Proc. Natl. Acad. Sci. USA* 95: 11538–11543 (1998); Kostrikis et al., *Science* 279:1228–1229 (1998); Marras et al., *Genet. Anal.* 14: 151–156 (1999); U.S. Pat. Nos. 5,846,726, 5,925,517, 5,925,517, or to report exonucleotidic excision, U.S. Pat. No. 5,538,848; Holland et al., *Proc. Natl. Acad. Sci. USA* 88:7276–7280 (1991); Heid et al., *Genome Res.* 6(10): 986–94 (1996); Kuimelis et al., *Nucleic Acids Symp* Ser. (37):255–6 (1997); U.S. Pat. No. 5,723,591, the disclosures of which are incorporated herein by reference in their entireties.

So labeled, the isolated nucleic acids of the present invention can be used as probes, as further described below.

Nucleic acids of the present invention can also usefully be bound to a substrate. The substrate can porous or solid, planar or non-planar, unitary or distributed; the bond can be covalent or noncovalent. Bound to a substrate, nucleic acids of the present invention can be used as probes in their unlabeled state.

For example, the nucleic acids of the present invention can usefully be bound to a porous substrate, commonly a membrane, typically comprising nitrocellulose, nylon, or positively-charged derivatized nylon; so attached, the nucleic acids of the present invention can be used to detect hGDMLP-1 nucleic acids present within a labeled nucleic acid sample, either a sample of genomic nucleic acids or a sample of transcript-derived nucleic acids, e.g. by reverse dot blot.

The nucleic acids of the present invention can also usefully be bound to a solid substrate, such as glass, although other solid materials, such as amorphous silicon, crystalline silicon, or plastics, can also be used. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof.

Typically, the solid substrate will be rectangular, although other shapes, particularly disks and even spheres, present certain advantages. Particularly advantageous alternatives to glass slides as support substrates for array of nucleic acids are optical discs, as described in Demers, "Spatially Addressable Combinatorial Chemical Arrays in CD-ROM Format," international patent publication WO 98/12559, incorporated herein by reference in its entirety.

The nucleic acids of the present invention can be attached covalently to a surface of the support substrate or applied to a derivatized surface in a chaotropic agent that facilitates denaturation and adherence by presumed noncovalent interactions, or some combination thereof.

The nucleic acids of the present invention can be bound to a substrate to which a plurality of other nucleic acids are concurrently bound, hybridization to each of the plurality of bound nucleic acids being separately detectable. At low density, e.g. on a porous membrane, these substrate-bound collections are typically denominated macroarrays; at higher density, typically on a solid support, such as glass, these substrate bound collections of plural nucleic acids are colloquially termed microarrays. As used herein, the term microarray includes arrays of all densities. It is, therefore, another aspect of the invention to provide microarrays that include the nucleic acids of the present invention.

The isolated nucleic acids of the present invention can be used as hybridization probes to detect, characterize, and quantify hGDMLP-1 nucleic acids in, and isolate hGDMLP-1 nucleic acids from, both genomic and transcript-derived nucleic acid samples. When free in solution, such probes are typically, but not invariably, detectably labeled; bound to a substrate, as in a microarray, such probes are typically, but not invariably, unlabeled.

For example, the isolated nucleic acids of the present invention can be used as probes to detect and characterize gross alterations in the hGDMLP-1 genomic locus, such as deletions, insertions, translocations, and duplications of the hGDMLP-1 genomic locus through fluorescence in situ hybridization (FISH) to chromosome spreads. See, e.g., Andreeff et al. (eds.), *Introduction to Fluorescence In Situ Hybridization: Principles and Clinical Applications*, John Wiley & Sons (1999) (ISBN: 0471013455), the disclosure of which is incorporated herein by reference in its entirety. The isolated nucleic acids of the present invention can be used as probes to assess smaller genomic alterations using, e.g., Southern blot detection of restriction fragment length polymorphisms. The isolated nucleic acids of the present invention can be used as probes to isolate genomic clones that include the nucleic acids of the present invention, which thereafter can be restriction mapped and sequenced to identify deletions, insertions, translocations, and substitutions (single nucleotide polymorphisms, SNPs) at the sequence level.

The isolated nucleic acids of the present invention can be also be used as probes to detect, characterize, and quantify hGDMLP-1 nucleic acids in, and isolate hGDMLP-1 nucleic acids from, transcript-derived nucleic acid samples.

For example, the isolated nucleic acids of the present invention can be used as hybridization probes to detect, characterize by length, and quantify hGDMLP-1 mRNA by northern blot of total or poly-A+−selected RNA samples. For example, the isolated nucleic acids of the present invention can be used as hybridization probes to detect, characterize by location, and quantify hGDMLP-1 message by in situ hybridization to tissue sections (see, e.g., Schwarchzacher et al., *In Situ Hybridization*, Springer-Verlag New York (2000) (ISBN: 0387915966), the disclosure of which is incorporated herein by reference in its entirety). For example, the isolated nucleic acids of the present invention can be used as hybridization probes to measure the representation of hGDMLP-1 clones in a cDNA library. For example, the isolated nucleic acids of the present invention can be used as hybridization probes to isolate hGDMLP-1 nucleic acids from cDNA libraries, permitting sequence level characterization of hGDMLP-1 messages, including identification of deletions, insertions, truncations—including deletions, insertions, and truncations of exons in alternatively spliced forms—and single nucleotide polymorphisms.

All of the aforementioned probe techniques are well within the skill in the art, and are described at greater length in standard texts such as Sambrook et al., *Molecular Cloning: A Laboratory Manual* (3rd ed.), Cold Spring Harbor Laboratory Press (2001) (ISBN: 0879695773); Ausubel et al. (eds.), *Short Protocols in Molecular Biology: A Compendium of Methods from Current Protocols in Molecular Biology* (4th ed.), John Wiley & Sons, 1999 (ISBN: 047132938X); and Walker et al. (eds.), *The Nucleic Acids Protocols Handbook*, Humana Press (2000) (ISBN: 0896034593), the disclosures of which are incorporated herein by reference in their entirety.

As described in the Examples herein below, the nucleic acids of the present invention can also be used to detect and quantify hGDMLP-1 nucleic acids in transcript-derived samples—that is, to measure expression of the hGDMLP-1 gene—when included in a microarray. Measurement of hGDMLP-1 expression has particular utility in diagnosis of genetic disorders of the hGDMLP-1 gene.

As would be readily apparent to one of skill in the art, each hGDMLP-1 nucleic acid probe—whether labeled, substrate-bound, or both—is thus currently available for use as a tool for measuring the level of hGDMLP-1 expression in each of the tissues in which expression has already been confirmed, notably in heart and skeletal muscle. The utility is specific to the probe: under high stringency conditions, the probe reports the level of expression of message specifically containing that portion of the hGDMLP-1 gene included within the probe.

Measuring tools are well known in many arts, not just in molecular biology, and are known to possess credible, specific, and substantial utility. For example, U.S. Pat. No. 6,016,191 describes and claims a tool for measuring characteristics of fluid flow in a hydrocarbon well; U.S. Pat. No. 6,042,549 describes and claims a device for measuring exercise intensity; U.S. Pat. No. 5,889,351 describes and claims a device for measuring viscosity and for measuring characteristics of a fluid; U.S. Pat. No. 5,570,694 describes and claims a device for measuring blood pressure; U.S. Pat. No. 5,930,143 describes and claims a device for measuring the dimensions of machine tools; U.S. Pat. No. 5,279,044 describes and claims a measuring device for determining an absolute position of a movable element; U.S. Pat. No. 5,186,042 describes and claims a device for measuring action force of a wheel; and U.S. Pat. No. 4,246,774 describes and claims a device for measuring the draft of smoking articles such as cigarettes.

As for tissues not yet demonstrated to express hGDMLP-1, the hGDMLP-1 nucleic acid probes of the present invention are currently available as tools for surveying such tissues to detect the presence of hGDMLP-1 nucleic acids.

Survey tools—i.e., tools for determining the presence and/or location of a desired object by search of an area—are well known in many arts, not just in molecular biology, and are known to possess credible, specific, and substantial utility. For example, U.S. Pat. No. 6,046,800 describes and claims a device for surveying an area for objects that move; U.S. Pat. No. 6,025,201 describes and claims an apparatus for locating and discriminating platelets from non-platelet particles or cells on a cell-by-cell basis in a whole blood sample; U.S. Pat. No. 5,990,689 describes and claims a device for detecting and locating anomalies in the electromagnetic protection of a system; U.S. Pat. No. 5,984,175 describes and claims a device for detecting and identifying wearable user identification units; U.S. Pat. No. 3,980,986 describes and claims a tool for finding the position of a drill bit working at the bottom of a borehole.

As noted above, the nucleic acid probes of the present invention are useful in constructing microarrays; the microarrays, in turn, are products of manufacture that are useful for measuring and for surveying gene expression.

When included on a microarray, each hGDMLP-1 nucleic acid probe makes the microarray specifically useful for detecting that portion of the hGDMLP-1 gene included within the probe, thus imparting upon the microarray device the ability to detect a signal where, absent such probe, it would have reported no signal. This utility makes each individual probe on such microarray akin to an antenna, circuit, firmware or software element included in an electronic apparatus, where the antenna, circuit, firmware or software element imparts upon the apparatus the ability newly and additionally to detect signal in a portion of the radio-frequency spectrum where previously it could not; such devices are known to have specific, substantial, and credible utility.

Changes in the level of expression need not be observed for the measurement of expression to have utility.

For example, where gene expression analysis is used to assess toxicity of chemical agents on cells, the failure of the agent to change a gene's expression level is evidence that the drug likely does not affect the pathway of which the gene's expressed protein is a part. Analogously, where gene expression analysis is used to assess side effects of pharmacologic agents—whether in lead compound discovery or in subsequent screening of lead compound derivatives—the inability of the agent to alter a gene's expression level is evidence that the drug does not affect the pathway of which the gene's expressed protein is a part. WO 99/58720, incorporated herein by reference in its entirety, provides methods for quantifying the relatedness of a first and second gene expression profile and for ordering the relatedness of a plurality of gene expression profiles, without regard to the identity or function of the genes whose expression is used in the calculation.

Gene expression analysis, including gene expression analysis by microarray hybridization, is, of course, principally a laboratory-based art. Devices and apparatus used principally in laboratories to facilitate laboratory research are well-established to possess specific, substantial, and credible utility. For example, U.S. Pat. No. 6,001,233 describes and claims a gel electrophoresis apparatus having a cam-activated clamp; for example, U.S. Pat. No. 6,051,831 describes and claims a high mass detector for use in time-of-flight mass spectrometers; for example, U.S. Pat. No. 5,824,269 describes and claims a flow cytometer—few gel electrophoresis apparatuses, TOF-MS devices, or flow cytometers are sold for home use.

Indeed, and in particular, nucleic acid microarrays, as devices intended for laboratory use in measuring gene expression, are well-established to have specific, substantial and credible utility. Thus, the microarrays of the present invention have at least the specific, substantial and credible utilities of the microarrays claimed as devices and articles of manufacture in the following U.S. patents, the disclosures of each of which is incorporated herein by reference: U.S. Pat. No. 5,445,934 ("Array of oligonucleotides on a solid substrate"); U.S. Pat. No. 5,744,305 ("Arrays of materials attached to a substrate"); and U.S. Pat. No. 6,004,752 ("Solid support with attached molecules").

Genome-derived single exon probes and genome-derived single exon probe microarrays have the additional utility, inter alia, of permitting high-throughput detection of splice variants of the nucleic acids of the present invention, as further described in copending and commonly owned U.S. patent application Ser. No. 09/632,366, filed Aug. 3, 2000, the disclosure of which is incorporated herein by reference in its entirety.

The isolated nucleic acids of the present invention can also be used to prime synthesis of nucleic acid, for purpose of either analysis or isolation, using mRNA, cDNA, or genomic DNA as template.

For use as primers, at least 17 contiguous nucleotides of the isolated nucleic acids of the present invention will be used. Often, at least 18, 19, or 20 contiguous nucleotides of the nucleic acids of the present invention will be used, and on occasion at least 20, 22, 24, or 25 contiguous nucleotides of the nucleic acids of the present invention will be used, and even 30 nucleotides or more of the nucleic acids of the present invention can be used to prime specific synthesis.

The nucleic acid primers of the present invention can be used, for example, to prime first strand cDNA synthesis on an mRNA template.

Such primer extension can be done directly to analyze the message. Alternatively, synthesis on an mRNA template can be done to produce first strand cDNA. The first strand cDNA can thereafter be used, inter alia, directly as a single-stranded probe, as above-described, as a template for sequencing—permitting identification of alterations, including deletions, insertions, and substitutions, both normal allelic variants and mutations associated with abnormal phenotypes- or as a template, either for second strand cDNA synthesis (e.g., as an antecedent to insertion into a cloning or expression vector), or for amplification.

The nucleic acid primers of the present invention can also be used, for example, to prime single base extension (SBE) for SNP detection (see, e.g., U.S. Pat. No. 6,004,744, the disclosure of which is incorporated herein by reference in its entirety).

As another example, the nucleic acid primers of the present invention can be used to prime amplification of hGDMLP-1 nucleic acids, using transcript-derived or genomic DNA as template.

Primer-directed amplification methods are now well-established in the art. Methods for performing the polymerase chain reaction (PCR) are compiled, inter alia, in McPherson, *PCR (Basics: From Background to Bench)*, Springer Verlag (2000) (ISBN: 0387916008); Innis et al. (eds.), *PCR Applications: Protocols for Functional Genomics*, Academic Press (1999) (ISBN: 0123721857); Gelfand et al. (eds.), *PCR Strategies*, Academic Press (1998) (ISBN: 0123721822); Newton et al., *PCR*, Springer-Verlag New York (1997) (ISBN: 0387915060); Burke (ed.), *PCR: Essential Techniques*, John Wiley & Son Ltd (1996) (ISBN: 047195697X); White (ed.), *PCR Cloning Protocols*: From Molecular Cloning to Genetic Engineering, Vol. 67, Humana Press (1996) (ISBN: 0896033430); McPherson et al. (eds.), *PCR 2: A Practical Approach*, Oxford University Press, Inc. (1995) (ISBN: 0199634254), the disclosures of which are incorporated herein by reference in their entireties. Methods for performing RT-PCR are collected, e.g., in Siebert et al. (eds.), *Gene Cloning and Analysis by RT-PCR*, Eaton Publishing Company/Bio Techniques Books Division, 1998 (ISBN: 1881299147); Siebert (ed.), *PCR Technique:RT-PCR*, Eaton Publishing Company/BioTechniques Books (1995) (ISBN:1881299139), the disclosure of which is incorporated herein by reference in its entirety.

Isothermal amplification approaches, such as rolling circle amplification, are also now well-described. See, e.g., Schweitzer et al., *Curr. Opin. Biotechnol.* 12(1):21–7 (2001); U.S. Pat. Nos. 5,854,033 and 5,714,320 and international patent publications WO 97/19193 and WO 00/15779, the disclosures of which are incorporated herein by reference in their entireties. Rolling circle amplification can be combined with other techniques to facilitate SNP detection. See, e.g., Lizardi et al., *Nature Genet.* 19(3):225–32 (1998).

As further described below, nucleic acids of the present invention, inserted into vectors that flank the nucleic acid insert with a phage promoter, such as T7, T3, or SP6 promoter, can be used to drive in vitro expression of RNA complementary to either strand of the nucleic acid of the present invention. The RNA can be used, inter alia, as a single-stranded probe, in cDNA-mRNA subtraction, or for in vitro translation.

As will be further discussed herein below, nucleic acids of the present invention that encode hGDMLP-1 protein or portions thereof can be used, inter alia, to express the hGDMLP-1 proteins or protein fragments, either alone, or as part of fusion proteins.

Expression can be from genomic nucleic acids of the present invention, or from transcript-derived nucleic acids of the present invention.

Where protein expression is effected from genomic DNA, expression will typically be effected in eukaryotic, typically mammalian, cells capable of splicing introns from the initial RNA transcript. Expression can be driven from episomal vectors, such as EBV-based vectors, or can be effected from genomic DNA integrated into a host cell chromosome. As will be more fully described below, where expression is from transcript-derived (or otherwise intron-less) nucleic acids of the present invention, expression can be effected in wide variety of prokaryotic or eukaryotic cells.

Expressed in vitro, the protein, protein fragment, or protein fusion can thereafter be isolated, to be used, inter alia, as a standard in immunoassays specific for the proteins, or protein isoforms, of the present invention; to be used as a therapeutic agent, e.g., to be administered as passive replacement therapy in individuals deficient in the proteins of the present invention, or to be administered as a vaccine; to be used for in vitro production of specific antibody, the antibody thereafter to be used, e.g., as an analytical reagent for detection and quantitation of the proteins of the present invention or to be used as an immunotherapeutic agent.

The isolated nucleic acids of the present invention can also be used to drive in vivo expression of the proteins of the present invention. In vivo expression can be driven from a vector—typically a viral vector, often a vector based upon a replication incompetent retrovirus, an adenovirus, or an adeno-associated virus (AAV)—for purpose of gene therapy. In vivo expression can also be driven from signals endogenous to the nucleic acid or from a vector, often a plasmid vector, such as pVAX1 (Invitrogen, Carlsbad, Calif., USA), for purpose of "naked" nucleic acid vaccination, as further described in U.S. Pat. Nos. 5,589,466; 5,679,647; 5,804, 566; 5,830,877; 5,843,913; 5,880,104; 5,958,891; 5,985, 847; 6,017,897; 6,110,898; 6,204,250, the disclosures of which are incorporated herein by reference in their entireties.

The nucleic acids of the present invention can also be used for antisense inhibition of transcription or translation. See Phillips (ed.), *Antisense Technology, Part B*, Methods in Enzymology Vol. 314, Academic Press, Inc. (1999) (ISBN: 012182215X); Phillips (ed.), *Antisense Technology, Part A*, Methods in Enzymology Vol. 313, Academic Press, Inc. (1999) (ISBN: 0121822141); Hartmann et al. (eds.), *Manual of Antisense Methodology* (Perspectives in Antisense Science), Kluwer Law International (1999) (ISBN:079238539X); Stein et al. (eds.), *Applied Antisense Oligonucleotide Technology*, Wiley-Liss (cover (1998) (ISBN: 0471172790); Agrawal et al. (eds.), *Antisense Research and Application*, Springer-Verlag New York, Inc. (1998) (ISBN: 3540638334); Lichtenstein et al. (eds.), *Antisense Technology: A Practical Approach*, Vol. 185, Oxford University Press, INC. (1998) (ISBN: 0199635838); Gibson (ed.), *Antisense and Ribozyme Methodology: Laboratory Companion*, Chapman & Hall (1997) (ISBN: 3826100794); Chadwick et al. (eds.), *Oligonucleotides as Therapeutic Agents—Symposium No. 209*, John Wiley & Son Ltd (1997) (ISBN: 0471972797), the disclosures of which are incorporated herein by reference in their entireties.

Nucleic acids of the present invention that encode full-length human hGDMLP-1 protein isoforms, particularly cDNAs encoding full-length isoforms, have additional, well-recognized, immediate, real world as commercial products of manufacture suitable for sale. For example, Invitrogen Corp. (Carlsbad, Calif., USA), through its Research Genetics subsidiary, sells full length human cDNAs (other than hGDMLP-1) cloned into one of a selection of expression vectors as GeneStorm® expression-ready clones; utility is specific for the gene, since each gene is capable of being ordered separately and has a distinct catalogue number, and utility is substantial, each clone selling for $650.00 US.

Nucleic acids of the present invention that include genomic regions encoding the human hGDMLP-1 protein, or portions thereof, have yet further utilities.

For example, genomic nucleic acids of the present invention can be used as amplification substrates, e.g. for preparation of genome-derived single exon probes of the present invention, described above, and further described in copending and commonly-owned U.S. patent application Ser. No. 09/774,203, filed Jan. 29, 2001, and Ser. No. 09/632,366, filed Aug. 3, 2000 and commonly-owned and copending U.S. provisional patent application No. 60/207,456, filed May 26, 2000, No. 60/234,687, filed Sep. 21, 2000, No. 60/236,359, filed Sep. 27, 2000, the disclosures of which are incorporated herein by reference in their entireties.

As another example, genomic nucleic acids of the present invention can be integrated non-homologously into the genome of somatic cells, with or without amplification of the insertional locus, in order, e.g., to create stable cell lines capable of producing the proteins of the present invention.

As another example, more fully described herein below, genomic nucleic acids of the present invention can be integrated nonhomologously into embryonic stem (ES) cells to create transgenic non-human animals capable of producing the proteins of the present invention.

Genomic nucleic acids of the present invention can also be used to target homologous recombination to the human hGDMLP-1 locus. See, e.g., U.S. Pat. Nos. 6,187,305; 6,204,061; 5,631,153; 5,627,059; 5,487,992; 5,464,764; 5,614,396; 5,527,695 and 6,063,630; and Kmiec et al. (eds.), *Gene Targeting Protocols*, Vol. 133, Humana Press (2000) (ISBN: 0896033600); Joyner (ed.), *Gene Targeting: A Practical Approach*, Oxford University Press, Inc. (2000) (ISBN: 0199637938); Sedivy et al., *Gene Targeting*, Oxford University Press (1998) (ISBN: 071677013X); Tymms et al. (eds.), *Gene Knockout Protocols*, Humana Press (2000) (ISBN: 0896035727); Mak et al. (eds.), *The Gene Knockout FactsBook*, Vol. 2, Academic Press, Inc. (1998) (ISBN: 0124660444); Torres et al., *Laboratory Protocols for Conditional Gene Targeting*, Oxford University Press (1997) (ISBN: 019963677X); Vega (ed.), *Gene Targeting*, CRC Press, LLC (1994) (ISBN: 084938950X), the disclosures of which are incorporated herein by reference in their entireties.

Where the genomic region includes transcription regulatory elements, homologous recombination can be used to alter the expression of hGDMLP-1, both for purpose of in vitro production of hGDMLP-1 protein from human cells, and for purpose of gene therapy. See, e.g., U.S. Pat. Nos. 5,981,214, 6,048,524; 5,272,071, incorporated herein by reference in their entireties.

Fragments of the nucleic acids of the present invention smaller than those typically used for homologous recombination can also be used for targeted gene correction or alteration, possibly by cellular mechanisms different from those engaged during homologous recombination.

For example, partially duplexed RNA/DNA chimeras have been shown to have utility in targeted gene correction, U.S. Pat. Nos. 5,945,339, 5,888,983, 5,871,984, 5,795,972, 5,780,296, 5,760,012, 5,756,325, 5,731,181, the disclosures of which are incorporated herein by reference in their entireties. So too have small oligonucleotides fused to triplexing domains have been shown to have utility in targeted gene correction, Culver et al., "Correction of chromosomal point mutations in human cells with bifunctional oligonucleotides," *Nature Biotechnol.* 17(10):989–93 (1999), as have oligonucleotides having modified terminal bases or modified terminal internucleoside bonds, Gamper et al., *Nucl. Acids Res.* 28(21):4332–9 (2000), the disclosures of which are incorporated herein by reference.

The isolated nucleic acids of the present invention can also be used to provide the initial substrate for recombinant engineering of hGDMLP-1 protein variants having desired phenotypic improvements. Such engineering includes, for example, site-directed mutagenesis, random mutagenesis with subsequent functional screening, and more elegant schemes for recombinant evolution of proteins, as are described, inter alia, in U.S. Pat. Nos. 6,180,406; 6,165,793; 6,117,679; and 6,096,548, the disclosures of which are incorporated herein by reference in their entireties.

Nucleic acids of the present invention can be obtained by using the labeled probes of the present invention to probe nucleic acid samples, such as genomic libraries, cDNA libraries, and mRNA samples, by standard techniques. Nucleic acids of the present invention can also be obtained by amplification, using the nucleic acid primers of the present invention, as further demonstrated in Example 1, herein below. Nucleic acids of the present invention of fewer than about 100 nt can also be synthesized chemically, typically by solid phase synthesis using commercially available automated synthesizers.

Vectors and Host Cells

In another aspect, the present invention provides vectors that comprise one or more of the isolated nucleic acids of the present invention, and host cells in which such vectors have been introduced.

The vectors can be used, inter alia, for propagating the nucleic acids of the present invention in host cells (cloning vectors), for shuttling the nucleic acids of the present invention between host cells derived from disparate organisms (shuttle vectors), for inserting the nucleic acids of the present invention into host cell chromosomes (insertion vectors), for expressing sense or antisense RNA transcripts of the nucleic acids of the present invention in vitro or within a host cell, and for expressing polypeptides encoded by the nucleic acids of the present invention, alone or as fusions to heterologous polypeptides. Vectors of the present invention will often be suitable for several such uses.

Vectors are by now well-known in the art, and are described, inter alia, in Jones et al. (eds.), *Vectors: Cloning Applications: Essential Techniques* (Essential Techniques Series), John Wiley & Son Ltd 1998 (ISBN: 047196266X); Jones et al. (eds.), *Vectors: Expression Systems: Essential Techniques* (Essential Techniques Series), John Wiley & Son Ltd, 1998 (ISBN:0471962678); Gacesa et al., *Vectors: Essential Data*, John Wiley & Sons, 1995 (ISBN: 0471948411); Cid-Arregui (eds.), *Viral Vectors: Basic Science and Gene Therapy*, Eaton Publishing Co., 2000 (ISBN: 188129935X); Sambrook et al., *Molecular Cloning: A Laboratory Manual* ($3^{rd}$ ed.), Cold Spring Harbor Laboratory Press, 2001 (ISBN: 0879695773); Ausubel et al. (eds.), *Short Protocols in Molecular Biology: A Compendium of Methods from Current Protocols in Molecular Biology* ($4^{th}$ ed.), John Wiley & Sons, 1999 (ISBN: 047132938X), the disclosures of which are incorporated herein by reference in their entireties. Furthermore, an enormous variety of vectors are available commercially. Use of existing vectors and modifications thereof being well within the skill in the art, only basic features need be described here.

Typically, vectors are derived from virus, plasmid, prokaryotic or eukaryotic chromosomal elements, or some combination thereof, and include at least one origin of replication, at least one site for insertion of heterologous nucleic acid, typically in the form of a polylinker with multiple, tightly clustered, single cutting restriction sites, and at least one selectable marker, although some integrative vectors will lack an origin that is functional in the host to be chromosomally modified, and some vectors will lack selectable markers. Vectors of the present invention will further include at least one nucleic acid of the present invention inserted into the vector in at least one location.

Where present, the origin of replication and selectable markers are chosen based upon the desired host cell or host cells; the host cells, in turn, are selected based upon the desired application.

For example, prokaryotic cells, typically *E. coli*, are typically chosen for cloning. In such case, vector replication is predicated on the replication strategies of coliform-infecting phage—such as phage lambda, M13, T7, T3 and P1—or on the replication origin of autonomously replicating episomes, notably the ColE1 plasmid and later derivatives, including pBR322 and the pUC series plasmids. Where *E. coli* is used as host, selectable markers are, analogously, chosen for selectivity in gram negative bacteria: e.g., typical markers confer resistance to antibiotics, such as ampicillin, tetracycline, chloramphenicol, kanamycin, streptomycin, zeocin; auxotrophic markers can also be used.

As another example, yeast cells, typically *S. cerevisiae*, are chosen, inter alia, for eukaryotic genetic studies, due to the ease of targeting genetic changes by homologous recombination and to the ready ability to complement genetic defects using recombinantly expressed proteins, for identification of interacting protein components, e.g. through use of a two-hybrid system, and for protein expression. Vectors of the present invention for use in yeast will typically, but not invariably, contain an origin of replication suitable for use in yeast and a selectable marker that is functional in yeast.

Integrative YIp vectors do not replicate autonomously, but integrate, typically in single copy, into the yeast genome at low frequencies and thus replicate as part of the host cell chromosome; these vectors lack an origin of replication that is functional in yeast, although they typically have at least one origin of replication suitable for propagation of the vector in bacterial cells. YEp vectors, in contrast, replicate episomally and autonomously due to presence of the yeast 2 micron plasmid origin (2 $\mu$m ori). The YCp yeast centromere plasmid vectors are autonomously replicating vectors containing centromere sequences, CEN, and autonomously replicating sequences, ARS; the ARS sequences are believed to correspond to the natural replication origins of yeast chromosomes.

Selectable markers in yeast vectors include a variety of auxotrophic markers, the most common of which are (in *Saccharomyces cerevisiae*) URA3, HIS3, LEU2, TRP1 and LYS2, which complement specific auxotrophic mutations, such as ura3-52, his3-D1, leu2-D1, trp1-D1 and lys2-201. The URA3 and LYS2 yeast genes further permit negative selection based on specific inhibitors, 5-fluoro-orotic acid (FOA) and $\alpha$-aminoadipic acid ($\alpha$AA), respectively, that prevent growth of the prototrophic strains but allows growth of the ura3 and lys2 mutants, respectively. Other selectable markers confer resistance to, e.g., zeocin.

As yet another example, insect cells are often chosen for high efficiency protein expression. Where the host cells are from *Spodoptera frugiperda*—e.g., Sf9 and Sf21 cell lines, and expresSF™ cells (Protein Sciences Corp., Meriden, Conn., USA)—the vector replicative strategy is typically based upon the baculovirus life cycle. Typically, baculovirus transfer vectors are used to replace the wild-type AcMNPV polyhedrin gene with a heterologous gene of interest. Sequences that flank the polyhedrin gene in the wild-type genome are positioned 5' and 3' of the expression cassette on the transfer vectors. Following cotransfection with AcMNPV DNA, a homologous recombination event occurs between these sequences resulting in a recombinant virus carrying the gene of interest and the polyhedrin or p10 promoter. Selection can be based upon visual screening for lacZ fusion activity.

As yet another example, mammalian cells are often chosen for expression of proteins intended as pharmaceutical agents, and are also chosen as host cells for screening of potential agonist and antagonists of a protein or a physiological pathway.

Where mammalian cells are chosen as host cells, vectors intended for autonomous extrachromosomal replication will typically include a viral origin, such as the SV40 origin (for replication in cell lines expressing the large T-antigen, such as COS1 and COS7 cells), the papillomavirus origin, or the EBV origin for long term episomal replication (for use, e.g., in 293-EBNA cells, which constitutively express the EBV EBNA-1 gene product and adenovirus E1A). Vectors intended for integration, and thus replication as part of the mammalian chromosome, can, but need not, include an origin of replication functional in mammalian cells, such as the SV40 origin. vectors based upon viruses, such as adenovirus, adeno-associated virus, vaccinia virus, and various mammalian retroviruses, will typically replicate according to the viral replicative strategy.

Selectable markers for use in mammalian cells include resistance to neomycin (G418), blasticidin, hygromycin and to zeocin, and selection based upon the purine salvage pathway using HAT medium.

Plant cells can also be used for expression, with the vector replicon typically derived from a plant virus (e.g., cauliflower mosaic virus, CaMV; tobacco mosaic virus, TMV) and selectable markers chosen for suitability in plants.

For propagation of nucleic acids of the present invention that are larger than can readily be accomodated in vectors derived from plasmids or virus, the invention further provides artificial chromosomes—BACs, YACs, and HACs—that comprise hGDMLP-1 nucleic acids, often genomic nucleic acids.

The BAC system is based on the well-characterized *E. coli* F-factor, a low copy plasmid that exists in a supercoiled circular form in host cells. The structural features of the F-factor allow stable maintenance of individual human DNA clones as well as easy manipulation of the cloned DNA. See Shizuya et al., *Keio J. Med.* 50(1):26–30 (2001); Shizuya et al., *Proc. Natl. Acad. Sci. USA* 89(18):8794–7 (1992).

YACs are based on yeast linear plasmids, denoted YLp, containing homologous or heterologous DNA sequences that function as telomeres (TEL) in vivo, as well as containing yeast ARS (origins of replication) and CEN (centromeres) segments.

HACs are human artifical chromosomes. Kuroiwa et al., *Nature Biotechnol.* 18(10):1086–90 (2000); Henning et al., *Proc. Natl. Acad. Sci. USA* 96(2):592–7 (1999); Harrington et al., *Nature Genet.* 15(4):345–55 (1997). In one version, long synthetic arrays of alpha satellite DNA are combined with telomeric DNA and genomic DNA to generate linear microchromosomes that are mitotically and cytogenetically stable in the absence of selection.

Vectors of the present invention will also often include elements that permit in vitro transcription of RNA from the inserted heterologous nucleic acid. Such vectors typically include a phage promoter, such as that from T7, T3, or SP6, flanking the nucleic acid insert. Often two different such promoters flank the inserted nucleic acid, permitting separate in vitro production of both sense and antisense strands.

Expression vectors of the present invention—that is, those vectors that will drive expression of polypeptides from the inserted heterologous nucleic acid—will often include a variety of other genetic elements operatively linked to the protein-encoding heterologous nucleic acid insert, typically genetic elements that drive transcription, such as promoters and enhancer elements, those that facilitate RNA processing, such as transcription termination and/or polyadenylation signals, and those that facilitate translation, such as ribosomal consensus sequences.

For example, vectors for expressing proteins of the present invention in prokaryotic cells, typically *E. coli*, will include a promoter, often a phage promoter, such as phage lambda pL promoter, the trc promoter, a hybrid derived from the trp and lac promoters, the bacteriophage T7 promoter (in *E. coli* cells engineered to express the T7 polymerase), or the araBAD operon. Often, such prokaryotic expression vectors will further include transcription terminators, such as the aspA terminator, and elements that facilitate translation, such as a consensus ribosome binding site and translation termination codon, Schomer et al., *Proc. Natl. Acad. Sci. USA* 83:8506–8510 (1986).

As another example, vectors for expressing proteins of the present invention in yeast cells, typically *S. cerevisiae*, will include a yeast promoter, such as the CYC1 promoter, the GAL1 promoter, ADH1 promoter, or the GPD promoter, and will typically have elements that facilitate transcription termination, such as the transcription termination signals from the CYC1 or ADH1 gene.

As another example, vectors for expressing proteins of the present invention in mammalian cells will include a promoter active in mammalian cells. Such promoters are often drawn from mammalian viruses—such as the enhancer-promoter sequences from the immediate early gene of the human cytomegalovirus (CMV), the enhancer-promoter sequences from the Rous sarcoma virus long terminal repeat (RSV LTR), and the enhancer-promoter from SV40. Often, expression is enhanced by incorporation of polyadenylation sites, such as the late SV40 polyadenylation site and the polyadenylation signal and transcription termination sequences from the bovine growth hormone (BGH) gene, and ribosome binding sites. Furthermore, vectors can include introns, such as intron II of rabbit β-globin gene and the SV40 splice elements.

Vector-drive protein expression can be constitutive or inducible.

Inducible vectors include either naturally inducible promoters, such as the trc promoter, which is regulated by the lac operon, and the pL promoter, which is regulated by tryptophan, the MMTV-LTR promoter, which is inducible by dexamethasone, or can contain synthetic promoters and/or additional elements that confer inducible control on adjacent promoters. Examples of inducible synthetic promoters are the hybrid Plac/ara-1 promoter and the PLtetO-1 promoter. The PltetO-1 promoter takes advantage of the high expression levels from the PL promoter of phage lambda, but replaces the lambda repressor sites with two copies of operator 2 of the Tn10 tetracycline resistance operon, causing this promoter to be tightly repressed by the Tet repressor protein and induced in response to tetracycline (Tc) and Tc derivatives such as anhydrotetracycline.

As another example of inducible elements, hormone response elements, such as the glucocorticoid response element (GRE) and the estrogen response element (ERE), can confer hormone inducibility where vectors are used for expression in cells having the respective hormone receptors. To reduce background levels of expression, elements responsive to ecdysone, an insect hormone, can be used instead, with coexpression of the ecdysone receptor.

Expression vectors can be designed to fuse the expressed polypeptide to small protein tags that facilitate purification and/or visualization.

For example, proteins of the present invention can be expressed with a polyhistidine tag that facilitates purification of the fusion protein by immobilized metal affinity chromatography, for example using NiNTA resin (Qiagen Inc., Valencia, Calif., USA) or TALON™ resin (cobalt immobilized affinity chromatography medium, Clontech Labs, Palo Alto, Calif., USA). As another example, the fusion protein can include a chitin-binding tag and self-excising intein, permitting chitin-based purification with self-removal of the fused tag (IMPACT™ system, New England Biolabs, Inc., Beverley, Mass., USA). Alternatively, the fusion protein can include a calmodulin-binding peptide tag, permitting purification by calmodulin affinity resin (Stratagene, La Jolla, Calif., USA), or a specifically excisable fragment of the biotin carboxylase carrier protein, permitting purification of in vivo biotinylated protein using an avidin resin and subsequent tag removal (Promega, Madison, Wis., USA). As another useful alternative, the proteins of the present invention can be expressed as a fusion to glutathione-S-transferase, the affinity and specificity of binding to glutathione permitting purification using glutathione affinity resins, such as Glutathione-Superflow Resin (Clontech Laboratories, Palo Alto, Calif., USA), with subsequent elution with free glutathione; proteins made in such systems can be designed to include heparin, thrombin, or factor Xa protease cleavage sites so that the cloned polypeptide of interest can be released from the GST moiety at will.

Other tags include, for example, the Xpress epitope, detectable by anti-Xpress antibody (Invitrogen, Carlsbad, Calif., USA), a myc tag, detectable by anti-myc tag antibody, the VS epitope, detectable by anti-VS antibody (Invitrogen, Carlsbad, Calif., USA), FLAG® epitope, detectable by anti-FLAG® antibody (Stratagene, La Jolla, Calif., USA), and the HA epitope.

For secretion of expressed proteins, vectors can include appropriate sequences that encode secretion signals, such as leader peptides. For example, the pSecTag2 vectors (Invitrogen, Carlsbad, Calif., USA) are 5.2 kb mammalian expression vectors that carry the secretion signal from the V-J2-C region of the mouse Ig kappa-chain for efficient secretion of recombinant proteins from a variety of mammalian cell lines.

Expression vectors can also be designed to fuse proteins encoded by the heterologous nucleic acid insert to polypeptides larger than purification and/or identification tags. Useful protein fusions include those that permit display of the encoded protein on the surface of a phage or cell, fusions to intrinsically fluorescent proteins, such as those having a green fluorescent protein (GFP)-like chromophore, fusions to the IgG Fc region, and fusions for use in two hybrid systems.

Vectors for phage display fuse the encoded polypeptide to, e.g., the gene III protein (pIII) or gene VIII protein (pVIII) for display on the surface of filamentous phage, such as M13. See Barbas et al., *Phage Display: A Laboratory Manual*, Cold Spring Harbor Laboratory Press (2001) (ISBN 0-87969-546-3); Kay et al. (eds.), *Phage Display of Peptides and Proteins: A Laboratory Manual*, San Diego: Academic Press, Inc., 1996; Abelson et al. (eds.), *Combinatorial Chemistry*, Methods in Enzymology vol. 267, Academic Press (May 1996).

Vectors for yeast display, e.g. the pYD1 yeast display vector (Invitrogen, Carlsbad, Calif., USA), use the a-agglutinin yeast adhesion receptor to display recombinant protein on the surface of *S. cerevisiae*. Vectors for mammalian display, e.g., the pDisplay™ vector (Invitrogen, Carlsbad, Calif., USA), target recombinant proteins using an N-terminal cell surface targeting signal and a C-terminal transmembrane anchoring domain of platelet derived growth factor receptor.

A wide variety of vectors now exist that fuse proteins encoded by heterologous nucleic acids to the chromophore of the substrate-independent, intrinsically fluorescent green fluorescent protein from *Aequorea victoria* ("GFP") and its variants. These proteins are intrinsically fluorescent: the GFP-like chromophore is entirely encoded by its amino acid sequence and can fluoresce without requirement for cofactor or substrate.

Structurally, the GFP-like chromophore comprises an 11-stranded β-barrel (β-can) with a central α-helix, the central α-helix having a conjugated n-resonance system that includes two aromatic ring systems and the bridge between them. The π-resonance system is created by autocatalytic cyclization among amino acids; cyclization proceeds through an imidazolinone intermediate, with subsequent dehydrogenation by molecular oxygen at the Cα-Cβ bond of a participating tyrosine.

The GFP-like chromophore can be selected from GFP-like chromophores found in naturally occurring proteins, such as *A. victoria* GFP (GenBank accession number AAA27721), *Renilla reniformis* GFP, FP583 (GenBank accession no. AF168419) (DsRed), FP593 (AF272711), FP483 (AF168420), FP484 (AF168424), FP595 (AF246709), FP486 (AF168421), FP538 (AF168423), and FP506 (AF168422), and need include only so much of the native protein as is needed to retain the chromophore's intrinsic fluorescence. Methods for determining the minimal domain required for fluorescence are known in the art. Li et al., "Deletions of the *Aequorea victoria* Green Fluorescent Protein Define the Minimal Domain Required for Fluorescence," *J. Biol. Chem.* 272:28545–28549 (1997).

Alternatively, the GFP-like chromophore can be selected from GFP-like chromophores modified from those found in nature. Typically, such modifications are made to improve recombinant production in heterologous expression systems (with or without change in protein sequence), to alter the excitation and/or emission spectra of the native protein, to facilitate purification, to facilitate or as a consequence of cloning, or are a fortuitous consequence of research investigation.

The methods for engineering such modified GFP-like chromophores and testing them for fluorescence activity, both alone and as part of protein fusions, are well-known in the art. Early results of these efforts are reviewed in Heim et al., *Curr. Biol.* 6:178–182 (1996), incorporated herein by reference in its entirety; a more recent review, with tabulation of useful mutations, is found in Palm et al., "Spectral Variants of Green Fluorescent Protein," in *Green Fluorescent Proteins*, Conn (ed.), *Methods Enzymol.* vol. 302, pp. 378–394 (1999), incorporated herein by reference in its entirety. A variety of such modified chromophores are now commercially available and can readily be used in the fusion proteins of the present invention.

For example, EGFP ("enhanced GFP"), Cormack et al., *Gene* 173:33–38 (1996); U.S. Pat. Nos. 6,090,919 and 5,804,387, is a red-shifted, human codon-optimized variant of GFP that has been engineered for brighter fluorescence, higher expression in mammalian cells, and for an excitation spectrum optimized for use in flow cytometers. EGFP can usefully contribute a GFP-like chromophore to the fusion proteins of the present invention. A variety of EGFP vectors, both plasmid and viral, are available commercially (Clontech Labs, Palo Alto, Calif., USA), including vectors for bacterial expression, vectors for N-terminal protein fusion expression, vectors for expression of C-terminal protein fusions, and for bicistronic expression.

Toward the other end of the emission spectrum, EBFP ("enhanced blue fluorescent protein") and BFP2 contain four amino acid substitutions that shift the emission from green to blue, enhance the brightness of fluorescence and improve solubility of the protein, Heim et al., *Curr. Biol.* 6:178–182 (1996); Cormack et al., *Gene* 173:33–38 (1996). EBFP is optimized for expression in mammalian cells whereas BFP2, which retains the original jellyfish codons, can be expressed in bacteria; as is further discussed below, the host cell of production does not affect the utility of the resulting fusion protein. The GFP-like chromophores from EBFP and BFP2 can usefully be included in the fusion proteins of the present invention, and vectors containing these blue-shifted variants are available from Clontech Labs (Palo Alto, Calif., USA).

Analogously, EYFP ("enhanced yellow fluorescent protein"), also available from Clontech Labs, contains four amino acid substitutions, different from EBFP, Ormö et al., *Science* 273:1392–1395 (1996), that shift the emission from green to yellowish-green. Citrine, an improved yellow fluorescent protein mutant, is described in Heikal et al., *Proc. Natl. Acad. Sci. USA* 97:11996–12001 (2000). ECFP ("enhanced cyan fluorescent protein") (Clontech Labs, Palo Alto, Calif., USA) contains six amino acid substitutions, one of which shifts the emission spectrum from green to cyan. Heim et al., *Curr. Biol.* 6:178–182 (1996); Miyawaki et al., *Nature* 388:882–887 (1997). The GFP-like chromophore of each of these GFP variants can usefully be included in the fusion proteins of the present invention.

The GFP-like chromophore can also be drawn from other modified GFPs, including those described in U.S. Pat. Nos. 6,124,128; 6,096,865; 6,090,919; 6,066,476; 6,054,321; 6,027,881; 5,968,750; 5,874,304; 5,804,387; 5,777,079; 5,741,668; and 5,625,048, the disclosures of which are incorporated herein by reference in their entireties. See also Conn (ed.), *Green Fluorescent Protein*, Methods in Enzymology, vol. 302, Academic Press, Inc. 1999 (ISBN: 0121822036).

Fusions to the IgG Fc region increase serum half life of protein pharmaceutical products through interaction with the FcRn receptor (also denominated the FcRp receptor and the Brambell receptor, FcRb), further described in international patent application nos. WO 97/43316, WO 97/34631, WO 96/32478, WO 96/18412, incorporated herein by reference in their entireties.

For long-term, high-yield recombinant production of the proteins, protein fusions, and protein fragments of the present invention, stable expression is preferred.

Stable expression is readily achieved by integration into the host cell genome of vectors having selectable markers, followed by selection for integrants.

For example, the pUB6/V5-His A, B, and C vectors (Invitrogen, Carlsbad, Calif., USA) are designed for high-level stable expression of heterologous proteins in a wide range of mammalian tissue types and cell lines. pUB6/V5-His uses the promoter/enhancer sequence from the human ubiquitin C gene to drive expression of recombinant proteins: expression levels in 293, CHO, and NIH3T3 cells are comparable to levels from the CMV and human EF-1α promoters. The bsd gene permits rapid selection of stably transfected mammalian cells with the potent antibiotic blasticidin.

Replication incompetent retroviral vectors, typically derived from Moloney murine leukemia virus, prove particularly useful for creating stable transfectants having integrated provirus. The highly efficient transduction machinery of retroviruses, coupled with the availability of a variety of packaging cell lines—such as RetroPack™PT 67, EcoPack2™-293, AmphoPack-293, GP2–293 cell lines (all available from Clontech Laboratories, Palo Alto, Calif., USA)—allow a wide host range to be infected with high efficiency; varying the multiplicity of infection readily adjusts the copy number of the integrated provirus. Retroviral vectors are available with a variety of selectable markers, such as resistance to neomycin, hygromycin, and puromycin, permitting ready selection of stable integrants.

The present invention further includes host cells comprising the vectors of the present invention, either present episomally within the cell or integrated, in whole or in part, into the host cell chromosome.

Among other considerations, some of which are described above, a host cell strain may be chosen for its ability to process the expressed protein in the desired fashion. Such post-translational modifications of the polypeptide include, but are not limited to, acetylation, carboxylation, glycosylation, phosphorylation, lipidation, and acylation, and it is an aspect of the present invention to provide hGDMLP-1 proteins with such post-translational modifications.

As noted earlier, host cells can be prokaryotic or eukaryotic.

Representative examples of appropriate host cells include, but are not limited to, bacterial cells, such as *E. coli, Caulobacter crescentus*, Streptomyces species, and *Salmonella typhimurium*; yeast cells, such as *Saccharomyces cerevisiae, Schizosaccharomyces pombe, Pichia pastoris, Pichia methanolica*; insect cell lines, such as those from *Spodoptera frugiperda*—e.g., Sf9 and Sf21 cell lines, and expresSF™ cells (Protein Sciences Corp., Meriden, Conn., USA)—Drosophila S2 cells, and Trichoplusia ni High Five® Cells (Invitrogen, Carlsbad, Calif., USA); and mammalian cells. Typical mammalian cells include COS1 and COS7 cells, chinese hamster ovary (CHO) cells, NIH 3T3 cells, 293 cells, HEPG2 cells, HeLa cells, L cells, HeLa, MDCK, HEK293, WI38, murine ES cell lines (e.g., from strains 129/SV, C57/BL6, DBA-1, 129/SVJ), K562, Jurkat cells, and BW5147. Other mammalian cell lines are well known and readily available from the American Type Culture Collection (ATCC) (Manassas, Va., USA) and the National Institute of General medical Sciences (NIGMS) Human Genetic Cell Repository at the Coriell Cell Repositories (Camden, N.J., USA).

Methods for introducing the vectors and nucleic acids of the present invention into the host cells are well known in the art; the choice of technique will depend primarily upon the specific vector to be introduced and the host cell chosen.

For example, phage lambda vectors will typically be packaged using a packaging extract (e.g., Gigapack® packaging extract, Stratagene, La Jolla, Calif., USA), and the packaged virus used to infect *E. coli*. Plasmid vectors will typically be introduced into chemically competent or electrocompetent bacterial cells.

*E. coli* cells can be rendered chemically competent by treatment, e.g., with $CaCl_2$, or a solution of $Mg^{2+}$, $Mn^{2+}$, $Ca^{2+}$, $Rb^+$ or $K^+$, dimethyl sulfoxide, dithiothreitol, and hexamine cobalt (III), Hanahan, *J. Mol. Biol.* 166(4):557–80 (1983), and vectors introduced by heat shock. A wide variety of chemically competent strains are also available commercially (e.g., Epicurian Coli® XL10-Gold® Ultracompetent Cells (Stratagene, La Jolla, Calif., USA); DH5α competent cells (Clontech Laboratories, Palo Alto, Calif., USA); TOP10 Chemically Competent *E. coli* Kit (Invitrogen, Carlsbad, Calif., USA)).

Bacterial cells can be rendered electrocompetent—that is, competent to take up exogenous DNA by electroporation—by various pre-pulse treatments; vectors are introduced by electroporation followed by subsequent outgrowth in selected media. An extensive series of protocols is provided online in *Electroprotocols Online: Collection of Protocols for Gene Transfer* (Bulletin #1029735, BioRad, Richmond, Calif., USA).

Vectors can be introduced into yeast cells by spheroplasting, treatment with lithium salts, electroporation, or protoplast fusion.

Spheroplasts are prepared by the action of hydrolytic enzymes—a snail-gut extract, usually denoted Glusulase, or Zymolyase, an enzyme from *Arthrobacter luteus*—to remove portions of the cell wall in the presence of osmotic stabilizers, typically 1 M sorbitol. DNA is added to the spheroplasts, and the mixture is co-precipitated with a solution of polyethylene glycol (PEG) and $Ca^{2+}$. Subsequently, the cells are resuspended in a solution of sorbitol, mixed with molten agar and then layered on the surface of a selective plate containing sorbitol. For lithium-mediated transformation, yeast cells are treated with lithium acetate, which apparently permeabilizes the cell wall, DNA is added and the cells are co-precipitated with PEG. The cells are exposed to a brief heat shock, washed free of PEG and lithium acetate, and subsequently spread on plates containing ordinary selective medium. Increased frequencies of transformation are obtained by using specially-prepared single-stranded carrier DNA and certain organic solvents. Schiestl et al., *Curr. Genet.* 16(5–6):339–46 (1989). For electroporation, freshly-grown yeast cultures are typically washed, suspended in an osmotic protectant, such as sorbitol, mixed with DNA, and the cell suspension pulsed in an electroporation device. Subsequently, the cells are spread on the surface of plates containing selective media. Becker et al., *Methods Enzymol.* 194:182–7 (1991). The efficiency of transformation by electroporation can be increased over 100-fold by using PEG, single-stranded carrier DNA and cells that are in late log-phase of growth. Larger constructs, such as YACs, can be introduced by protoplast fusion.

Mammalian and insect cells can be directly infected by packaged viral vectors, or transfected by chemical or electrical means.

For chemical transfection, DNA can be coprecipitated with $CaPO_4$ or introduced using liposomal and nonliposomal lipid-based agents. Commercial kits are available for $CaPO_4$ transfection (CalPhos™ Mammalian Transfection Kit, Clontech Laboratories, Palo Alto, Calif., USA), and lipid-mediated transfection can be practiced using commercial reagents, such as LIPOFECTAMINE™ 2000, LIPO-FECTAMINE™ Reagent, CELLFECTIN® Reagent, and LIPOFECTIN® Reagent (Invitrogen, Carlsbad, Calif., USA), DOTAP Liposomal Transfection Reagent, FuGENE 6, X-tremeGENE Q2, DOSPER, (Roche Molecular Biochemicals, Indianapolis, Ind. USA), Effectene™, PolyFect®, Superfect® (Qiagen, Inc., Valencia, Calif., USA). Protocols for electroporating mammalian cells can be found online in *Electroprotocols Online: Collection of Protocols for Gene Transfer* (Bulletin #1029735, BioRad, Richmond, Calif., USA). See also, Norton et al. (eds.), *Gene Transfer Methods: Introducing DNA into Living Cells and Organisms*, BioTechniques Books, Eaton Publishing Co. (2000) (ISBN 1-881299-34-1), incorporated herein by reference in its entirety.

Other transfection techniques include transfection by particle embardment. See, e.g., Cheng et al., *Proc. Natl. Acad. Sci. USA* 90(10):4455–9 (1993); Yang et al., *Proc. Natl. Acad. Sci. USA* 87(24):9568–72 (1990).

Proteins

In another aspect, the present invention provides hGDMLP-1 proteins, various fragments thereof suitable for use as antigens (e.g., for epitope mapping) and for use as immunogens (e.g., for raising antibodies or as vaccines), fusions of hGDMLP-1 polypeptides and fragments to heterologous polypeptides, and conjugates of the proteins, fragments, and fusions of the present invention to other moieties (e.g., to carrier proteins, to fluorophores).

FIG. 2 presents the predicted amino acid sequence encoded by the hGDMLP-1cDNA clone. The amino acid sequence is further presented, respectively, in the Sequence Listing.

Unless otherwise indicated, amino acid sequences of the proteins of the present invention were determined as a predicted translation from a nucleic acid sequence. Accordingly, any amino acid sequence presented herein may contain errors due to errors in the nucleic acid sequence, as described in detail above. Furthermore, single nucleotide polymorphisms (SNPs) occur frequently in eukaryotic genomes—more than 1.4 million SNPs have already been identified in the human genome, International Human Genome Sequencing Consortium, *Nature* 409:860–921 (2001)—and the sequence determined from one individual of a species may differ from other allelic forms present within the population. Small deletions and insertions can often be found that do not alter the function of the protein.

Accordingly, it is an aspect of the present invention to provide proteins not only identical in sequence to those described with particularity herein, but also to provide isolated proteins at least about 65% identical in sequence to those described with particularity herein, typically at least about 70%, 75%, 80%, 85%, or 90% identical in sequence to those described with particularity herein, usefully at least about 91%, 92%, 93%, 94%, or 95% identical in sequence to those described with particularity herein, usefully at least about 96%, 97%, 98%, or 99% identical in sequence to those described with particularity herein, and, most conservatively, at least about 99.5%, 99.6%, 99.7%, 99.8% and 99.9% identical in sequence to those described with particularity herein. These sequence variants can be naturally occurring or can result from human intervention by way of random or directed mutagenesis.

For purposes herein, percent identity of two amino acid sequences is determined using the procedure of Tatiana et al., "Blast 2 sequences—a new tool for comparing protein and nucleotide sequences", FEMS *Microbiol Lett.* 174:247–250 (1999), which procedure is effectuated by the computer program BLAST 2 SEQUENCES, available online at the National Center for Biotechnology Information (NCBI) website. To assess percent identity of amino acid sequences, the BLASTP module of BLAST 2 SEQUENCES is used with default values of (i) BLOSUM62 matrix, Henikoff et al., *Proc. Nati. Acad. Sd USA* 89(22):10915–9 (1992); (ii) open gap 11 and extension gap 1 penalties; and (iii) gap x_dropoff 50 expect 10 word size 3 filter, and both sequences are entered in their entireties.

As is well known, amino acid substitutions occur frequently among natural allelic variants, with conservative substitutions often occasioning only de minimis change in protein function.

Accordingly, it is an aspect of the present invention to provide proteins not only identical in sequence to those described with particularity herein, but also to provide isolated proteins having the sequence of hGDMLP-1 proteins, or portions thereof, with conservative amino acid substitutions. It is a further aspect to provide isolated proteins having the sequence of hGDMLP-1 proteins, and portions thereof, with moderately conservative amino acid substitutions. These conservatively-substituted or moderately conservatively-substituted variants can be naturally occurring or can result from human intervention.

Although there are a variety of metrics for calling conservative amino acid substitutions, based primarily on either observed changes among evolutionarily related proteins or on predicted chemical similarity, for purposes herein a conservative replacement is any change having a positive value in the PAM250 log-likelihood matrix reproduced herein below (see Gonnet et al., *Science* 256(5062):1443–5 (1992)):

such as chimpanzee, rhesus macaque monkey, baboon, orangutan, and gorilla; from rodents, such as rats, mice, guinea pigs; from lagomorphs, such as rabbits, and from domestic livestock, such as cow, pig, sheep, horse, goat.

Relatedness of proteins can also be characterized using a second functional test, the ability of a first protein competitively to inhibit the binding of a second protein to an antibody.

It is, therefore, another aspect of the present invention to provide isolated proteins not only identical in sequence to those described with particularity herein, but also to provide isolated proteins ("cross-reactive proteins") that competitively inhibit the binding of antibodies to all or to a portion of various of the isolated hGDMLP-1 proteins of the present invention ("reference proteins"). Such competitive inhibition can readily be determined using immunoassays well known in the art.

Among the proteins of the present invention that differ in amino acid sequence from those described with particularity

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 2 | -1 | 0 | 0 | 0 | 0 | 0 | 0 | -1 | -1 | -1 | 0 | -1 | -2 | 0 | 1 | 1 | -4 | -2 | 0 |
| R | -1 | 5 | 0 | 0 | -2 | 2 | 0 | -1 | 1 | -2 | -2 | 3 | -2 | -3 | -1 | 0 | 0 | -2 | -2 | -2 |
| N | 0 | 0 | 4 | 2 | -2 | 1 | 1 | 0 | 1 | -3 | -3 | 1 | -2 | -3 | -1 | 1 | 0 | -4 | -1 | -2 |
| D | 0 | 0 | 2 | 5 | -3 | 1 | 3 | 0 | 0 | -4 | -4 | 0 | -3 | -4 | -1 | 0 | 0 | -5 | -3 | -3 |
| C | 0 | -2 | -2 | -3 | 12 | -2 | -3 | -2 | -1 | -1 | -2 | -3 | -1 | -1 | -3 | 0 | 0 | -1 | 0 | 0 |
| Q | 0 | 2 | 1 | 1 | -2 | 3 | 2 | -1 | 1 | -2 | -2 | 2 | -1 | -3 | 0 | 0 | 0 | -3 | -2 | -2 |
| E | 0 | 0 | 1 | 3 | -3 | 2 | 4 | -1 | 0 | -3 | -3 | 1 | -2 | -4 | 0 | 0 | 0 | -4 | -3 | -2 |
| G | 0 | -1 | 0 | 0 | -2 | -1 | -1 | 7 | -1 | -4 | -4 | -1 | -4 | -5 | -2 | 0 | -1 | -4 | -4 | -3 |
| H | -1 | 1 | 1 | 0 | -1 | 1 | 0 | -1 | 6 | -2 | -2 | 1 | -1 | 0 | -1 | 0 | 0 | -1 | 2 | -2 |
| I | -1 | -2 | -3 | -4 | -1 | -2 | -3 | -4 | -2 | 4 | 3 | -2 | 2 | 1 | -3 | -2 | -1 | -2 | -1 | 3 |
| L | -1 | -2 | -3 | -4 | -2 | -2 | -3 | -4 | -2 | 3 | 4 | -2 | 3 | 2 | -2 | -2 | -1 | -1 | 0 | 2 |
| K | 0 | 3 | 1 | 0 | -3 | 2 | 1 | -1 | 1 | -2 | -2 | 3 | -1 | -3 | -1 | 0 | 0 | -4 | -2 | -2 |
| M | -1 | -2 | -2 | -3 | -1 | -1 | -2 | -4 | -1 | 2 | 3 | -1 | 4 | 2 | -2 | -1 | -1 | -1 | 0 | 2 |
| F | -2 | -3 | -3 | -4 | -1 | -3 | -4 | -5 | 0 | 1 | 2 | -3 | 2 | 7 | -4 | -3 | -2 | 4 | 5 | 0 |
| P | 0 | -1 | -1 | -1 | -3 | 0 | 0 | -2 | -1 | -3 | -2 | -1 | -2 | -4 | 8 | 0 | 0 | -5 | -3 | -2 |
| S | 1 | 0 | 1 | 0 | 0 | 0 | 0 | 0 | 0 | -2 | -2 | 0 | -1 | -3 | 0 | 2 | 2 | -3 | -2 | -1 |
| T | 1 | 0 | 0 | 0 | 0 | 0 | 0 | -1 | 0 | -1 | -1 | 0 | -1 | -2 | 0 | 2 | 2 | -4 | -2 | 0 |
| W | -4 | -2 | -3 | -5 | -1 | -3 | -4 | -4 | -1 | -2 | -1 | -4 | -1 | 4 | -5 | -3 | -4 | 14 | 4 | -3 |
| Y | -2 | -2 | -1 | -3 | 0 | -2 | -3 | -4 | 2 | -1 | 0 | -2 | 0 | 5 | -3 | -2 | -2 | 4 | 8 | -1 |
| V | 0 | -2 | -2 | -3 | 0 | -2 | -2 | -3 | -2 | 3 | 2 | -2 | 2 | 0 | -2 | -1 | 0 | -3 | -1 | 3 |

For purposes herein, a "moderately conservative" replacement is any change having a nonnegative value in the PAM250 log-likelihood matrix reproduced herein above.

As is also well known in the art, relatedness of proteins can also be characterized using a functional test, the ability of the encoding nucleic acids to base-pair to one another at defined hybridization stringencies.

It is, therefore, another aspect of the invention to provide isolated proteins not only identical in sequence to those described with particularity herein, but also to provide isolated proteins ("hybridization related proteins") that are encoded by nucleic acids that hybridize under high stringency conditions (as defined herein above) to all or to a portion of various of the isolated nucleic acids of the present invention ("reference nucleic acids"). It is a further aspect of the invention to provide isolated proteins ("hybridization related proteins") that are encoded by nucleic acids that hybridize under moderate stringency conditions (as defined herein above) to all or to a portion of various of the isolated nucleic acids of the present invention ("reference nucleic acids").

The hybridization related proteins can be alternative isoforms, homologues, paralogues, and orthologues of the hGDMLP-1 protein of the present invention. Particularly useful orthologues are those from other primate species, herein—including those that have deletions and insertions causing up to 10% non-identity, those having conservative or moderately conservative substitutions, hybridization related proteins, and cross-reactive proteins—those that are biologically active, i.e., that retain at least one structural, regulatory, or biological or biochemical activity of hGDMLP-1. As described above, and further described in Example 1, below, those activities include ATPase activity, actin-binding, calmodulin binding, possession of an IQ domain, and possession of a myosin heavy chain-like tail.

Residues that are tolerant of change while retaining function can be identified by altering the protein at known residues using methods known in the art, such as alanine scanning mutagenesis, Cunningham et al., *Science* 244 (4908):1081–5 (1989); transposon linker scanning mutagenesis, Chen et al., *Gene* 263(1–2):39–48 (2001); combinations of homolog- and alanine-scanning mutagenesis, Jin et al., *J. Mol. Biol.* 226(3):851–65 (1992); combinatorial alanine scanning, Weiss et al., *Proc. Natl. Acad. Sci USA* 97(16):8950–4 (2000), followed by functional assay. Transposon linker scanning kits are available commercially (New England Biolabs, Beverly, Mass., USA, catalog. no. E7–102S; EZ::TN™ In-Frame Linker Insertion Kit, catalogue no. EZI04KN, Epicentre Technologies Corporation, Madison, Wis., USA).

As further described below, the isolated proteins of the present invention can readily be used as specific immunogens to raise antibodies that specifically recognize hGDMLP-1 proteins, their isoforms, homologues, paralogues, and/or orthologues. The antibodies, in turn, can be used, inter alia, specifically to assay for the hGDMLP-1 proteins of the present invention—e.g. by ELISA for detection of protein fluid samples, such as serum, by immunohistochemistry or laser scanning cytometry, for detection of protein in tissue samples, or by flow cytometry, for detection of intracellular protein in cell suspensions—for specific antibody-mediated isolation and/or purification of hGDMLP-1 proteins, as for example by immunoprecipitation, and for use as specific agonists or antagonists of hGDMLP-1 action.

The isolated proteins of the present invention are also immediately available for use as specific standards in assays used to determine the concentration and/or amount specifically of the hGDMLP-1 proteins of the present invention. As is well known, ELISA kits for detection and quantitation of protein analytes typically include isolated and purified protein of known concentration for use as a measurement standard (e.g., the human interferon-γ OptEIA kit, catalog no. 555142, Pharmingen, San Diego, Calif., USA includes human recombinant gamma interferon, baculovirus produced).

The isolated proteins of the present invention are also immediately available for use as specific biomolecule capture probes for surface-enhanced laser desorption ionization (SELDI) detection of protein—protein interactions, WO 98/59362; WO 98/59360; WO 98/59361; and Merchant et al., *Electrophoresis* 21(6):1164–77 (2000), the disclosures of which are incorporated herein by reference in their entireties. Analogously, the isolated proteins of the present invention are also immediately available for use as specific biomolecule capture probes on BIACORE surface plasmon resonance probes. See Weinberger et al., *Pharmacogenomics* 1(4):395–416 (2000); Malmqvist, Biochem. Soc. Trans. 27(2):335–40 (1999).

The isolated proteins of the present invention are also useful as a therapeutic supplement in patients having a specific deficiency in hGDMLP-1 production.

In another aspect, the invention also provides fragments of various of the proteins of the present invention. The protein fragments are useful, inter alia, as antigenic and immunogenic fragments of hGDMLP-1.

By "fragments" of a protein is here intended isolated proteins (equally, polypeptides, peptides, oligopeptides), however obtained, that have an amino acid sequence identical to a portion of the reference amino acid sequence, which portion is at least 6 amino acids and less than the entirety of the reference nucleic acid. As so defined, "fragments" need not be obtained by physical fragmentation of the reference protein, although such provenance is not thereby precluded.

Fragments of at least 6 contiguous amino acids are useful in mapping B cell and T cell epitopes of the reference protein. See, e.g., Geysen et al., "Use of peptide synthesis to probe viral antigens for epitopes to a resolution of a single amino acid," *Proc. Natl. Acad. Sci. USA* 81:3998–4002 (1984) and U.S. Pat. Nos. 4,708,871 and 5,595,915, the disclosures of which are incorporated herein by reference in their entireties. Because the fragment need not itself be immunogenic, part of an immunodominant epitope, nor even recognized by native antibody, to be useful in such epitope mapping, all fragments of at least 6 amino acids of the proteins of the present invention have utility in such a study.

Fragments of at least 8 contiguous amino acids, often at least 15 contiguous amino acids, have utility as immunogens for raising antibodies that recognize the proteins of the present invention. See, e.g., Lerner, "Tapping the immunological repertoire to produce antibodies of predetermined specificity," Nature 299:592–596 (1982); Shinnick et al., "Synthetic peptide immunogens as vaccines," *Annu. Rev. Microbiol.* 37:425–46 (1983); Sutcliffe et al., "Antibodies that react with predetermined sites on proteins," *Science* 219:660–6 (1983), the disclosures of which are incorporated herein by reference in their entireties. As further described in the above-cited references, virtually all 8-mers, conjugated to a carrier, such as a protein, prove immunogenic—that is, prove capable of eliciting antibody for the conjugated peptide; accordingly, all fragments of at least 8 amino acids of the proteins of the present invention have utility as immunogens.

Fragments of at least 8, 9, 10 or 12 contiguous amino acids are also useful as competitive inhibitors of binding of the entire protein, or a portion thereof, to antibodies (as in epitope mapping), and to natural binding partners, such as subunits in a multimeric complex or to receptors or ligands of the subject protein; this competitive inhibition permits identification and separation of molecules that bind specifically to the protein of interest, U.S. Pat. Nos. 5,539,084 and 5,783,674, incorporated herein by reference in their entireties.

The protein, or protein fragment, of the present invention is thus at least 6 amino acids in length, typically at least 8, 9, 10 or 12 amino acids in length, and often at least 15 amino acids in length. Often, the protein or the present invention, or fragment thereof, is at least 20 amino acids in length, even 25 amino acids, 30 amino acids, 35 amino acids, or 50 amino acids or more in length. Of course, larger fragments having at least 75 amino acids, 100 amino acids, or even 150 amino acids are also useful, and at times preferred.

The present invention further provides fusions of each of the proteins and protein fragments of the present invention to heterologous polypeptides.

By fusion is here intended that the protein or protein fragment of the present invention is linearly contiguous to the heterologous polypeptide in a peptide-bonded polymer of amino acids or amino acid analogues; by "heterologous polypeptide" is here intended a polypeptide that does not naturally occur in contiguity with the protein or protein fragment of the present invention. As so defined, the fusion can consist entirely of a plurality of fragments of the hGDMLP-1 protein in altered arrangement; in such case, any of the hGDMLP-1 fragments can be considered heterologous to the other hGDMLP-1 fragments in the fusion protein. More typically, however, the heterologous polypeptide is not drawn from the hGDMLP-1 protein itself.

The fusion proteins of the present invention will include at least one fragment of the protein of the present invention, which fragment is at least 6, typically at least 8, often at least 15, and usefully at least 16, 17, 18, 19, or 20 amino acids long. The fragment of the protein of the present to be included in the fusion can usefully be at least 25 amino acids long, at least 50 amino acids long, and can be at least 75, 100, or even 150 amino acids long. Fusions that include the entirety of the proteins of the present invention have particular utility.

The heterologous polypeptide included within the fusion protein of the present invention is at least 6 amino acids in length, often at least 8 amino acids in length, and usefully at least 15, 20, and 25 amino acids in length. Fusions that include larger polypeptides, such as the IgG Fc region, and even entire proteins (such as GFP chromophore-containing proteins), have particular utility.

As described above in the description of vectors and expression vectors of the present invention, which discussion is incorporated here by reference in its entirety, heterologous polypeptides to be included in the fusion proteins of the present invention can usefully include those designed to facilitate purification and/or visualization of recombinantly-expressed proteins. Although purification tags can also be incorporated into fusions that are chemically synthesized, chemical synthesis typically provides sufficient purity that further purification by HPLC suffices; however, visualization tags as above described retain their utility even when the protein is produced by chemical synthesis, and when so included render the fusion proteins of the present invention useful as directly detectable markers of hGDMLP-1 presence.

As also discussed above, heterologous polypeptides to be included in the fusion proteins of the present invention can usefully include those that facilitate secretion of recombinantly expressed proteins—into the periplasmic space or extracellular milieu for prokaryotic hosts, into the culture medium for eukaryotic cells—through incorporation of secretion signals and/or leader sequences.

Other useful protein fusions of the present invention include those that permit use of the protein of the present invention as bait in a yeast two-hybrid system. See Bartel et al. (eds.), *The Yeast Two-Hybrid System*, Oxford University Press (1997) (ISBN: 0195109384); Zhu et al., *Yeast Hybrid Technologies*, Eaton Publishing, (2000) (ISBN 1-881299-15-5); Fields et al., *Trends Genet.* 10(8):286–92 (1994); Mendelsohn et al., *Curr. Opin. Biotechnol.* S(5):482–6 (1994); Luban et al., *Curr. Opin. Biotechnol.* 6(1):59–64 (1995); Allen et al., Trends Biochem. Sci. 20(12):511–6 (1995); Drees, *Curr. Opin. Chem. Biol.* 3(1):64–70 (1999); Topcu et al., *Pharm. Res.* 17(9):1049–55 (2000); Fashena et al., Gene 250(1–2):1–14 (2000), the disclosures of which are incorporated herein by reference in their entireties. Typically, such fusion is to either *E. coli* LexA or yeast GAL4 DNA binding domains. Related bait plasmids are available that express the bait fused to a nuclear localization signal.

Other useful protein fusions include those that permit display of the encoded protein on the surface of a phage or cell, fusions to intrinsically fluorescent proteins, such as green fluorescent protein (GFP), and fusions to the IgG Fc region, as described above, which discussion is incorporated here by reference in its entirety.

The proteins and protein fragments of the present invention can also usefully be fused to protein toxins, such as Pseudomonas exotoxin A, diphtheria toxin, shiga toxin A, anthrax toxin lethal factor, ricin, in order to effect ablation of cells that bind or take up the proteins of the present invention.

The isolated proteins, protein fragments, and protein fusions of the present invention can be composed of natural amino acids linked by native peptide bonds, or can contain any or all of nonnatural amino acid analogues, nonnative bonds, and post-synthetic (post translational) modifications, either throughout the length of the protein or localized to one or more portions thereof.

As is well known in the art, when the isolated protein is used, e.g., for epitope mapping, the range of such nonnatural analogues, nonnative inter-residue bonds, or post-synthesis modifications will be limited to those that permit binding of the peptide to antibodies. When used as an immunogen for the preparation of antibodies in a non-human host, such as a mouse, the range of such nonnatural analogues, nonnative inter-residue bonds, or post-synthesis modifications will be limited to those that do not interfere with the immunogenicity of the protein. When the isolated protein is used as a therapeutic agent, such as a vaccine or for replacement therapy, the range of such changes will be limited to those that do not confer toxicity upon the isolated protein.

Non-natural amino acids can be incorporated during solid phase chemical synthesis or by recombinant techniques, although the former is typically more common.

Solid phase chemical synthesis of peptides is well established in the art. Procedures are described, inter alia, in Chan et al. (eds.), *Fmoc Solid Phase Peptide Synthesis: A Practical Approach* (Practical Approach Series), Oxford Univ. Press (March 2000) (ISBN: 0199637245); Jones, *Amino Acid and Peptide Synthesis* (Oxford Chemistry Primers, No 7), Oxford Univ. Press (August 1992) (ISBN: 0198556683); and Bodanszky, *Principles of Peptide Synthesis* (Springer Laboratory), Springer Verlag (December 1993) (ISBN: 0387564314), the disclosures of which are incorporated herein by reference in their entireties.

Non-natural amino acids can be incorporated during solid phase chemical synthesis.

For example, D-enantiomers of natural amino acids can readily be incorporated during chemical peptide synthesis: peptides assembled from D-amino acids are more resistant to proteolytic attack; incorporation of D-enantiomers can also be used to confer specific three dimensional conformations on the peptide. Other amino acid analogues commonly added during chemical synthesis include ornithine, norleucine, phosphorylated amino acids (typically phosphoserine, phosphothreonine, phosphotyrosine), L-malonyltyrosine, a non-hydrolyzable analog of phosphotyrosine (Kole et al., *Biochem. Biophys. Res. Com.* 209:817–821 (1995)), and various halogenated phenylalanine derivatives.

Amino acid analogues having detectable labels are also usefully incorporated during synthesis to provide a labeled polypeptide.

Biotin, for example can be added using biotinoyl—(9-fluorenylmethoxycarbonyl)-L-lysine (FMOC biocytin) (Molecular Probes, Eugene, Oreg., USA). (Biotin can also be added enzymatically by incorporation into a fusion protein of a *E. coli* BirA substrate peptide.)

The FMOC and tBOC derivatives of dabcyl-L-lysine (Molecular Probes, Inc., Eugene, Oreg., USA) can be used to incorporate the dabcyl chromophore at selected sites in the peptide sequence during synthesis. The aminonaphthalene derivative EDANS, the most common fluorophore for pairing with the dabcyl quencher in fluorescence resonance energy transfer (FRET) systems, can be introduced during automated synthesis of peptides by using EDANS—FMOC-L-glutamic acid or the corresponding tBOC derivative (both from Molecular Probes, Inc., Eugene, Oreg., USA). Tetramethylrhodamine fluorophores can be incorporated during automated FMOC synthesis of peptides using (FMOC)—TMR-L-lysine (Molecular Probes, Inc. Eugene, Oreg., USA).

Other useful amino acid analogues that can be incorporated during chemical synthesis include aspartic acid, glutamic acid, lysine, and tyrosine analogues having allyl side-chain protection (Applied Biosystems, Inc., Foster City, Calif., USA); the allyl side chain permits synthesis of cyclic, branched-chain, sulfonated, glycosylated, and phosphorylated peptides.

A large number of other FMOC-protected non-natural amino acid analogues capable of incorporation during chemical synthesis are available commercially, including, e.g., Fmoc-2-aminobicyclo[2.2.1]heptane-2-carboxylic acid, Fmoc-3-endo-aminobicyclo[2.2.1]heptane-2-endo-carboxylic acid, Fmoc-3-exo-aminobicyclo[2.2.1]heptane-2-exo-carboxylic acid, Fmoc-3-endo-amino-bicyclo[2.2.1] hept-5-ene-2-endo-carboxylic acid, Fmoc-3-exo-amino-bicyclo[2.2.1]hept-5-ene-2-exo-carboxylic acid, Fmoc-cis-2-amino-1-cyclohexanecarboxylic acid, Fmoc-trans-2-amino-1-cyclohexanecarboxylic acid, Fmoc-1-amino-1-cyclopentanecarboxylic acid, Fmoc-cis-2-amino-1-cyclopentanecarboxylic acid, Fmoc-1-amino-1-cyclopropanecarboxylic acid, Fmoc-D-2-amino-4-(ethylthio)butyric acid, Fmoc-L-2-amino-4-(ethylthio) butyric acid, Fmoc-L-buthionine, Fmoc-S-methyl-L-Cysteine, Fmoc-2-aminobenzoic acid (anthranillic acid), Fmoc-3-aminobenzoic acid, Fmoc-4-aminobenzoic acid, Fmoc-2-aminobenzophenone-2'-carboxylic acid, Fmoc-N-(4-aminobenzoyl)-b-alanine, Fmoc-2-amino-4,5-dimethoxybenzoic acid, Fmoc-4-aminohippuric acid, Fmoc-2-amino-3-hydroxybenzoic acid, Fmoc-2-amino-5-hydroxybenzoic acid, Fmoc-3-amino-4-hydroxybenzoic acid, Fmoc-4-amino-3-hydroxybenzoic acid, Fmoc-4-amino-2-hydroxybenzoic acid, Fmoc-5-amino-2-hydroxybenzoic acid, Fmoc-2-amino-3-methoxybenzoic acid, Fmoc-4-amino-3-methoxybenzoic acid, Fmoc-2-amino-3-methylbenzoic acid, Fmoc-2-amino-5-methylbenzoic acid, Fmoc-2-amino-6-methylbenzoic acid, Fmoc-3-amino-2-methylbenzoic acid, Fmoc-3-amino-4-methylbenzoic acid, Fmoc-4-amino-3-methylbenzoic acid, Fmoc-3-amino-2-naphtoic acid, Fmoc-D,L-3-amino-3-phenylpropionic acid, Fmoc-L-Methyldopa, Fmoc-2-amino-4,6-dimethyl-3-pyridinecarboxylic acid, Fmoc-D,L-?-amino-2-thiophenacetic acid, Fmoc-4-(carboxymethyl) piperazine, Fmoc-4-carboxypiperazine, Fmoc-4-(carboxymethyl)homopiperazine, Fmoc-4-phenyl-4-piperidinecarboxylic acid, Fmoc-L-1,2,3,4-tetrahydronorharman-3-carboxylic acid, Fmoc-L-thiazolidine-4-carboxylic acid, all available from The Peptide Laboratory (Richmond, Calif., USA).

Non-natural residues can also be added biosynthetically by engineering a suppressor tRNA, typically one that recognizes the UAG stop codon, by chemical aminoacylation with the desired unnatural amino acid and. Conventional site-directed mutagenesis is used to introduce the chosen stop codon UAG at the site of interest in the protein gene. When the acylated suppressor tRNA and the mutant gene are combined in an in vitro transcription/translation system, the unnatural amino acid is incorporated in response to the UAG codon to give a protein containing that amino acid at the specified position. Liu et al., *Proc. Natl Acad. Sci. USA* 96(9):4780–5 (1999); Wang et al., *Science* 292(5516):498–500 (2001).

The isolated proteins, protein fragments and fusion proteins of the present invention can also include nonnative inter-residue bonds, including bonds that lead to circular and branched forms.

The isolated proteins and protein fragments of the present invention can also include post-translational and post-synthetic modifications, either throughout the length of the protein or localized to one or more portions thereof.

For example, when produced by recombinant expression in eukaryotic cells, the isolated proteins, fragments, and fusion proteins of the present invention will typically include N-linked and/or 0-linked glycosylation, the pattern of which will reflect both the availability of glycosylation sites on the protein sequence and the identity of the host cell. Further modification of glycosylation pattern can be performed enzymatically.

As another example, recombinant polypeptides of the invention can also include an initial modified methionine residue, in some cases resulting from host-mediated processes.

When the proteins, protein fragments, and protein fusions of the present invention are produced by chemical synthesis, post-synthetic modification can be performed before deprotection and cleavage from the resin or after deprotection and cleavage. Modification before deprotection and cleavage of the synthesized protein often allows greater control, e.g. by allowing targeting of the modifying moiety to the N-terminus of a resin-bound synthetic peptide.

Useful post-synthetic (and post-translational) modifications include conjugation to detectable labels, such as fluorophores.

A wide variety of amine-reactive and thiol-reactive fluorophore derivatives have been synthesized that react under nondenaturing conditions with N-terminal amino groups and epsilon amino groups of lysine residues, on the one hand, and with free thiol groups of cysteine residues, on the other.

Kits are available commercially that permit conjugation of proteins to a variety of amine-reactive or thiol-reactive fluorophores: Molecular Probes, Inc. (Eugene, Oreg., USA), e.g., offers kits for conjugating proteins to Alexa Fluor 350, Alexa Fluor 430, Fluorescein-EX, Alexa Fluor 488, Oregon Green 488, Alexa Fluor 532, Alexa Fluor 546, Alexa Fluor 546, Alexa Fluor 568, Alexa Fluor 594, and Texas Red-X.

A wide variety of other amine-reactive and thiol-reactive fluorophores are available commercially (Molecular Probes, Inc., Eugene, Oreg., USA), including Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA).

The polypeptides of the present invention can also be conjugated to fluorophores, other proteins, and other macromolecules, using bifunctional linking reagents.

Common homobifunctional reagents include, e.g., APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS (all available from Pierce, Rockford, Ill., USA); common heterobifunctional cross-linkers include ABH, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, M2C2H, MPBH, MSA, NHS-ASA, PDPH, PMPI, SADP, SAED, SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS, Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS (all available Pierce, Rockford, Ill., USA).

The proteins, protein fragments, and protein fusions of the present invention can be conjugated, using such cross-linking reagents, to fluorophores that are not amine- or thiol-reactive.

Other labels that usefully can be conjugated to the proteins, protein fragments, and fusion proteins of the present invention include radioactive labels, echosonographic contrast reagents, and MRI contrast agents.

The proteins, protein fragments, and protein fusions of the present invention can also usefully be conjugated using cross-linking agents to carrier proteins, such as KLH, bovine thyroglobulin, and even bovine serum albumin (BSA), to increase immunogenicity for raising anti-hGDMLP-lantibodies.

The proteins, protein fragments, and protein fusions of the present invention can also usefully be conjugated to polyethylene glycol (PEG); PEGylation increases the serum half life of proteins administered intravenously for replacement therapy. Delgado et al., *Crit. Rev. Ther. Drug Carrier Syst.* 9(3–4):249–304 (1992); Scott et al., *Curr. Pharm. Des.* 4(6):423–38 (1998); DeSantis et al., *Curr. Opin. Biotechnol.* 10(4):324–30 (1999), incorporated herein by reference in their entireties. PEG monomers can be attached to the protein directly or through a linker, with PEGylation using PEG monomers activated with tresyl chloride (2,2,2-trifluoroethanesulphonyl chloride) permitting direct attachment under mild conditions.

The isolated proteins of the present invention, including fusions thereof, can be produced by recombinant expression, typically using the expression vectors of the present invention as above-described or, if fewer than about 100 amino acids, by chemical synthesis (typically, solid phase synthesis), and, on occasion, by in vitro translation.

Production of the isolated proteins of the present invention can optionally be followed by purification.

Purification of recombinantly expressed proteins is now well within the skill in the art. See, e.g., Thorner et al. (eds.), *Applications of Chimeric Genes and Hybrid Proteins, Part A: Gene Expression and Protein Purification* (Methods in Enzymology, Volume 326), Academic Press (2000), (ISBN: 0121822273); Harbin (ed.), *Cloning, Gene Expression and Protein Purification: Experimental Procedures and Process Rationale*, Oxford Univ. Press (2001) (ISBN: 0195132947); Marshak et al., *Strategies for Protein Purification and Characterization: A Laboratory Course Manual*, Cold Spring Harbor Laboratory Press (1996) (ISBN: 0-87969-385-1); and Roe (ed.), *Protein Purification Applications*, Oxford University Press (2001), the disclosures of which are incorporated herein by reference in their entireties, and thus need not be detailed here.

Briefly, however, if purification tags have been fused through use of an expression vector that appends such tag, purification can be effected, at least in part, by means appropriate to the tag, such as use of immobilized metal affinity chromatography for polyhistidine tags. Other techniques common in the art include ammonium sulfate fractionation, immunoprecipitation, fast protein liquid chromatography (FPLC), high performance liquid chromatography (HPLC), and preparative gel electrophoresis.

Purification of chemically-synthesized peptides can readily be effected, e.g., by HPLC.

Accordingly, it is an aspect of the present invention to provide the isolated proteins of the present invention in pure or substantially pure form.

A purified protein of the present invention is an isolated protein, as above described, that is present at a concentration of at least 95%, as measured on a mass basis (w/w) with respect to total protein in a composition. Such purities can often be obtained during chemical synthesis without further purification, as, e.g., by HPLC. Purified proteins of the present invention can be present at a concentration (measured on a mass basis with respect to total protein in a composition) of 96%, 97%, 98%, and even 99%. The proteins of the present invention can even be present at levels of 99.5%, 99.6%, and even 99.7%, 99.8%, or even 99.9% following purification, as by HPLC.

Although high levels of purity are preferred when the isolated proteins of the present invention are used as therapeutic agents—such as vaccines, or for replacement therapy—the isolated proteins of the present invention are also useful at lower purity. For example, partially purified proteins of the present invention can be used as immunogens to raise antibodies in laboratory animals.

Thus, in another aspect, the present invention provides the isolated proteins of the present invention in substantially purified form. A "substantially purified protein" of the present invention is an isolated protein, as above described, present at a concentration of at least 70%, measured on a mass basis with respect to total protein in a composition. Usefully, the substantially purified protein is present at a concentration, measured on a mass basis with respect to total protein in a composition, of at least 75%, 80%, or even at least 85%, 90%, 91%, 92%, 93%, 94%, 94.5% or even at least 94.9%.

In preferred embodiments, the purified and substantially purified proteins of the present invention are in compositions that lack detectable ampholytes, acrylamide monomers, bis-acrylamide monomers, and polyacrylamide.

The proteins, fragments, and fusions of the present invention can usefully be attached to a substrate. The substrate can porous or solid, planar or non-planar; the bond can be covalent or noncovalent.

For example, the proteins, fragments, and fusions of the present invention can usefully be bound to a porous substrate, commonly a membrane, typically comprising nitrocellulose, polyvinylidene fluoride (PVDF), or cationically derivatized, hydrophilic PVDF; so bound, the proteins, fragments, and fusions of the present invention can be used to detect and quantify antibodies, e.g. in serum, that bind specifically to the immobilized protein of the present invention.

As another example, the proteins, fragments, and fusions of the present invention can usefully be bound to a substantially nonporous substrate, such as plastic, to detect and quantify antibodies, e.g. in serum, that bind specifically to the immobilized protein of the present invention. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof; when the assay is performed in standard microtiter dish, the plastic is typically polystyrene.

The proteins, fragments, and fusions of the present invention can also be attached to a substrate suitable for use as a surface enhanced laser desorption ionization source; so attached, the protein, fragment, or fusion of the present invention is useful for binding and then detecting secondary proteins that bind with sufficient affinity or avidity to the surface-bound protein to indicate biologic interaction therebetween. The proteins, fragments, and fusions of the present invention can also be attached to a substrate suitable for use in surface plasmon resonance detection; so attached, the protein, fragment, or fusion of the present invention is useful for binding and then detecting secondary proteins that bind with sufficient affinity or avidity to the surface-bound protein to indicate biological interaction therebetween.

Antibodies and Antibody-producing Cells

In another aspect, the invention provides antibodies, including fragments and derivatives thereof, that bind specifically to hGDMLP-1 proteins and protein fragments of the present invention, or that bind to one or more of the proteins and protein fragments encoded by the isolated hGDMLP-1 nucleic acids of the present invention. The antibodies of the present invention can be specific for linear epitopes, discontinuous epitopes, or conformational epitopes of such proteins or protein fragments, either as present on the protein in its native conformation or, in some cases, as present on the proteins as denatured, as, e.g., by solubilization in SDS.

In other embodiments, the invention provides antibodies, including fragments and derivatives thereof, the binding of which can be competitively inhibited by one or more of the hGDMLP-1 proteins and protein fragments of the present invention, or by one or more of the proteins and protein fragments encoded by the isolated hGDMLP-1 nucleic acids of the present invention.

As used herein, the term "antibody" refers to a polypeptide, at least a portion of which is encoded by at least one immunoglobulin gene, which can bind specifically to a first molecular species, and to fragments or derivatives thereof that remain capable of such specific binding.

By "bind specifically" and "specific binding" is here intended the ability of the antibody to bind to a first molecular species in preference to binding to other molecular species with which the antibody and first molecular species are admixed. An antibody is said specifically to "recognize" a first molecular species when it can bind specifically to that first molecular species.

As is well known in the art, the degree to which an antibody can discriminate as among molecular species in a mixture will depend, in part, upon the conformational relatedness of the species in the mixture; typically, the antibodies of the present invention will discriminate over adventitious binding to non-hGDMLP-1 proteins by at least two-fold, more typically by at least 5-fold, typically by more than 10-fold, 25-fold, 50-fold, 75-fold, and often by more than 100-fold, and on occasion by more than 500-fold or 1000-fold. When used to detect the proteins or protein fragments of the present invention, the antibody of the present invention is sufficiently specific when it can be used to determine the presence of the protein of the present invention in samples derived from human heart or skeletal muscle.

Typically, the affinity or avidity of an antibody (or antibody multimer, as in the case of an IgM pentamer) of the present invention for a protein or protein fragment of the present invention will be at least about $1\times10^{-6}$ molar (M), typically at least about $5\times10^{-7}$ M, usefully at least about $1\times10^{-7}$ M, with affinities and avidities of at least $1\times10^{-8}$ M, $5\times10^{-9}$ M, and $1\times10^{-10}$ M proving especially useful.

The antibodies of the present invention can be naturally-occurring forms, such as IgG, IgM, IgD, IgE, and IgA, from any mammalian species.

Human antibodies can, but will infrequently, be drawn directly from human donors or human cells. In such case, antibodies to the proteins of the present invention will typically have resulted from fortuitous immunization, such as autoimmune immunization, with the protein or protein fragments of the present invention. Such antibodies will typically, but will not invariably, be polyclonal.

Human antibodies are more frequently obtained using transgenic animals that express human immunoglobulin genes, which transgenic animals can be affirmatively immunized with the protein immunogen of the present invention. Human Ig-transgenic mice capable of producing human antibodies and methods of producing human antibodies therefrom upon specific immunization are described, inter alia, in U.S. Pat. Nos. 6,162,963; 6,150,584; 6,114,598; 6,075,181; 5,939,598; 5,877,397; 5,874,299; 5,814,318; 5,789,650; 5,770,429; 5,661,016; 5,633,425; 5,625,126; 5,569,825; 5,545,807; 5,545,806, and 5,591,669, the disclosures of which are incorporated herein by reference in their entireties. Such antibodies are typically monoclonal, and are typically produced using techniques developed for production of murine antibodies.

Human antibodies are particularly useful, and often preferred, when the antibodies of the present invention are to be administered to human beings as in vivo diagnostic or therapeutic agents, since recipient immune response to the administered antibody will often be substantially less than that occasioned by administration of an antibody derived from another species, such as mouse.

IgG, IgM, IgD, IgE and IgA antibodies of the present invention are also usefully obtained from other mammalian species, including rodents typically mouse, but also rat, guinea pig, and hamster—lagomorphs, typically rabbits, and also larger mammals, such as sheep, goats, cows, and horses. In such cases, as with the transgenic human-antibody-producing non-human mammals, fortuitous immunization is not required, and the non-human mammal is typically affirmatively immunized, according to standard immunization protocols, with the protein or protein fragment of the present invention.

As discussed above, virtually all fragments of 8 or more contiguous amino acids of the proteins of the present invention can be used effectively as immunogens when conjugated to a carrier, typically a protein such as bovine thyroglobulin, keyhole limpet hemocyanin, or bovine serum albumin, conveniently using a bifunctional linker such as those described elsewhere above, which discussion is incorporated by reference here.

Immunogenicity can also be conferred by fusion of the proteins and protein fragments of the present invention to other moieties.

For example, peptides of the present invention can be produced by solid phase synthesis on a branched polylysine core matrix; these multiple antigenic peptides (MAPs) provide high purity, increased avidity, accurate chemical definition and improved safety in vaccine development. Tam et al., Proc. Natl. Acad. Sci. USA 85:5409–5413 (1988); Posnett et al., *J. Biol. Chem.* 263, 1719–1725 (1988).

Protocols for immunizing non-human mammals are well-established in the art, Harlow et al. (eds.), *Antibodies: A Laboratory Manual*, Cold Spring Harbor Laboratory (1998) (ISBN: 0879693142); Coligan et al. (eds.), *Current Protocols in Immunology*, John Wiley & Sons, Inc. (2001) (ISBN: 0-471-52276-7); Zola, *Monoclonal Antibodies: Preparation and Use of Monoclonal Antibodies and Engineered Antibody Derivatives (Basics: From Background to Bench)*, Springer Verlag (2000) (ISBN: 0387915907), the disclosures of which are incorporated herein by reference, and often include multiple immunizations, either with or without adjuvants such as Freund's complete adjuvant and Freund's incomplete adjuvant.

Antibodies from nonhuman mammals can be polyclonal or monoclonal, with polyclonal antibodies having certain advantages in immunohistochemical detection of the proteins of the present invention and monoclonal antibodies having advantages in identifying and distinguishing particular epitopes of the proteins of the present invention.

Following immunization, the antibodies of the present invention can be produced using any art-accepted technique.

Such techniques are well known in the art, Coligan et al. (eds.), *Current Protocols in Immunology*, John Wiley & Sons, Inc. (2001) (ISBN: 0-471-52276-7); Zola, *Monoclonal Antibodies: Preparation and Use of Monoclonal Antibodies and Engineered Antibody Derivatives* (*Basics: From Background to Bench*), Springer Verlag (2000) (ISBN: 0387915907); Howard et al. (eds.), *Basic Methods in Antibody Production and Characterization*, CRC Press (2000) (ISBN: 0849394457); Harlow et al. (eds.), *Antibodies: A Laboratory Manual*, Cold Spring Harbor Laboratory (1998) (ISBN: 0879693142); Davis (ed.), *Monoclonal Antibody Protocols*, Vol. 45, Humana Press (1995) (ISBN: 0896033082); Delves (ed.), *Antibody Production: Essential Techniques*, John Wiley & Son Ltd (1997) (ISBN: 0471970107); Kenney, *Antibody Solution: An Antibody Methods Manual*, Chapman & Hall (1997) (ISBN: 0412141914), incorporated herein by reference in their entireties, and thus need not be detailed here.

Briefly, however, such techniques include, inter alia, production of monoclonal antibodies by hybridomas and expression of antibodies or fragments or derivatives thereof from host cells engineered to express immunoglobulin genes or fragments thereof. These two methods of production are not mutually exclusive: genes encoding antibodies specific for the proteins or protein fragments of the present invention can be cloned from hybridomas and thereafter expressed in other host cells. Nor need the two necessarily be performed together: e.g., genes encoding antibodies specific for the proteins and protein fragments of the present invention can be cloned directly from B cells known to be specific for the desired protein, as further described in U.S. Pat. No. 5,627,052, the disclosure of which is incorporated herein by reference in its entirety, or from antibody-displaying phage.

Recombinant expression in host cells is particularly useful when fragments or derivatives of the antibodies of the present invention are desired.

Host cells for recombinant antibody production—either whole antibodies, antibody fragments, or antibody derivatives—can be prokaryotic or eukaryotic.

Prokaryotic hosts are particularly useful for producing phage displayed antibodies of the present invention.

The technology of phage-displayed antibodies, in which antibody variable region fragments are fused, for example, to the gene III protein (pIII) or gene VIII protein (PVIII) for display on the surface of filamentous phage, such as M13, is by now well-established, Sidhu, *Curr. Opin. Biotechnol.* 11(6):610–6 (2000); Griffiths et al., *Curr. Opin. Biotechnol.* 9(1):102–8 (1998); Hoogenboom et al., *Immunotechnology*, 4(1):1–20 (1998); Rader et al., *Current Opinion in Biotechnology* 8:503–508 (1997); Aujame et al., *Human Antibodies* 8:155–168 (1997); Hoogenboom, *Trends in Biotechnol.* 15:62–70 (1997); de Kruif et al., 17:453–455 (1996); Barbas et al., *Trends in Biotechnol.* 14:230–234 (1996); Winter et al., *Ann. Rev. Immunol.* 433–455 (1994), and techniques and protocols required to generate, propagate, screen (pan), and use the antibody fragments from such libraries have recently been compiled, Barbas et al., *Phage Display: A Laboratory Manual*, Cold Spring Harbor Laboratory Press (2001) (ISBN 0-87969-546-3); Kay et al. (eds.), *Phage Display of Peptides and Proteins: A Laboratory Manual*, Academic Press, Inc. (1996); Abelson et al. (eds.), *Combinatorial Chemistry*, Methods in Enzymology vol. 267, Academic Press (May 1996), the disclosures of which are incorporated herein by reference in their entireties.

Typically, phage-displayed antibody fragments are scFv fragments or Fab fragments; when desired, full length antibodies can be produced by cloning the variable regions from the displaying phage into a complete antibody and expressing the full length antibody in a further prokaryotic or a eukaryotic host cell.

Eukaryotic cells are also useful for expression of the antibodies, antibody fragments, and antibody derivatives of the present invention.

For example, antibody fragments of the present invention can be produced in Pichia pastoris, Takahashi et al., *Biosci. Biotechnol. Biochem.* 64(10):2138–44 (2000); Freyre et al., *J. Biotechnol.* 76(2–3):157–63 (2000); Fischer et al., *Biotechnol. Appl. Biochem.* 30 (Pt 2):117–20 (1999); Pennell et al., *Res. Immunol.* 149(6):599–603 (1998); Eldin et al., *J. Immunol. Methods.* 201(1):67–75 (1997); and in *Saccharomyces cerevisiae*, Frenken et al., *Res. Immunol.* 149(6): 589–99 (1998); Shusta et al., *Nature Biotechnol.* 16(8): 773–7 (1998), the disclosures of which are incorporated herein by reference in their entireties.

Antibodies, including antibody fragments and derivatives, of the present invention can also be produced in insect cells, Li et al., *Protein Expr. Purif.* 21(1):121–8 (2001); Ailor et al., *Biotechnol. Bioeng.* 58(2–3):196–203 (1998); Hsu et al., *Biotechnol. Prog.* 13(1):96–104 (1997); Edelman et al., *Immunology* 91(1):13–9 (1997); and Nesbit et al., *J. Immunol. Methods.* 151(1–2):201–8 (1992), the disclosures of which are incorporated herein by reference in their entireties.

Antibodies and fragments and derivatives thereof of the present invention can also be produced in plant cells, Giddings et al., *Nature Biotechnol.* 18(11):1151–5 (2000); Gavilondo et al., *Biotechniques* 29(1):128–38 (2000); Fischer et al., *J. Biol. Regul. Homeost. Agents* 14(2):83–92 (2000); Fischer et al., *Biotechnol. Appl. Biochem.* 30 (Pt 2):113–6 (1999); Fischer et al., *Biol. Chem.* 380(7–8): 825–39 (1999); Russell, *Curr. Top. Microbiol. Immunol.* 240:119–38 (1999); and Ma et al., *Plant Physiol.* 109(2): 341–6 (1995), the disclosures of which are incorporated herein by reference in their entireties.

Mammalian cells useful for recombinant expression of antibodies, antibody fragments, and antibody derivatives of the present invention include CHO cells, COS cells, 293 cells, and myeloma cells.

Verma et al., *J. Immunol. Methods* 216(1–2):165–81 (1998), review and compare bacterial, yeast, insect and mammalian expression systems for expression of antibodies.

Antibodies of the present invention can also be prepared by cell free translation, as further described in Merk et al., *J. Biochem. (Tokyo).* 125(2):328–33 (1999) and Ryabova et al., *Nature Biotechnol.* 15(1):79–84 (1997), and in the milk of transgenic animals, as further described in Pollock et al., *J. Immunol. Methods* 231(1–2):147–57 (1999), the disclosures of which are incorporated herein by reference in their entireties.

The invention further provides antibody fragments that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful fragments are Fab, Fab', Fv, F(ab)'$_2$, and single chain Fv (scFv) fragments. Other useful fragments are described in Hudson, *Curr. Opin. Biotechnol.* 9(4):395–402 (1998).

It is also an aspect of the present invention to provide antibody derivatives that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful derivatives are chimeric, primatized, and humanized antibodies; such derivatives are less immunogenic in human beings, and thus more suitable for in vivo administration, than are unmodified antibodies from non-human mammalian species.

Chimeric antibodies typically include heavy and/or light chain variable regions (including both CDR and framework residues) of immunoglobulins of one species, typically mouse, fused to constant regions of another species, typically human. See, e.g., U.S. Pat. No. 5,807,715; Morrison et al., *Proc. Natl. Acad. Sci USA.* 81(21):6851–5 (1984); Sharon et al., *Nature* 309(5966):364–7 (1984); Takeda et al., *Nature* 314(6010):452–4 (1985), the disclosures of which are incorporated herein by reference in their entireties. Primatized and humanized antibodies typically include heavy and/or light chain CDRs from a murine antibody grafted into a non-human primate or human antibody V region framework, usually further comprising a human constant region, Riechmann et al., *Nature* 332(6162):323–7 (1988); Co et al., *Nature* 351(6326):501–2 (1991); U.S. Pat. Nos. 6,054,297; 5,821,337; 5,770,196; 5,766,886; 5,821,123; 5,869,619; 6,180,377; 6,013,256; 5,693,761; and 6,180,370, the disclosures of which are incorporated herein by reference in their entireties.

Other useful antibody derivatives of the invention include heteromeric antibody complexes and antibody fusions, such as diabodies (bispecific antibodies), single-chain diabodies, and intrabodies.

The antibodies of the present invention, including fragments and derivatives thereof, can usefully be labeled. It is, therefore, another aspect of the present invention to provide labeled antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

The choice of label depends, in part, upon the desired use.

For example, when the antibodies of the present invention are used for immunohistochemical staining of tissue samples, the label can usefully be an enzyme that catalyzes production and local deposition of a detectable product.

Enzymes typically conjugated to antibodies to permit their immunohistochemical visualization are well known, and include alkaline phosphatase, β-galactosidase, glucose oxidase, horseradish peroxidase (HRP), and urease. Typical substrates for production and deposition of visually detectable products include o-nitrophenyl-beta-D-galactopyranoside (ONPG); o-phenylenediamine dihydrochloride (OPD); p-nitrophenyl phosphate (PNPP); p-nitrophenyl-beta-D-galactopryanoside (PNPG); 3',3'-diaminobenzidine (DAB); 3-amino-9-ethylcarbazole (AEC); 4-chloro-1-naphthol (CN); 5-bromo-4-chloro-3-indolyl-phosphate (BCIP); ABTS®; BluoGal; iodonitrotetrazolium (INT); nitroblue tetrazolium chloride (NBT); phenazine methosulfate (PMS); phenolphthalein monophosphate (PMP); tetramethyl benzidine (TMB); tetranitroblue tetrazolium (TNBT); X-Gal; X-Gluc; and X-Glucoside.

Other substrates can be used to produce products for local deposition that are luminescent. For example, in the presence of hydrogen peroxide ($H_2O_2$), horseradish peroxidase (HRP) can catalyze the oxidation of cyclic diacylhydrazides, such as luminol. Immediately following the oxidation, the luminol is in an excited state (intermediate reaction product), which decays to the ground state by emitting light. Strong enhancement of the light emission is produced by enhancers, such as phenolic compounds. Advantages include high sensitivity, high resolution, and rapid detection without radioactivity and requiring only small amounts of antibody. See, e.g., Thorpe et al., *Methods Enzymol.* 133:331–53 (1986); Kricka et al., *J. Immunoassay* 17(1): 67–83 (1996); and Lundqvist et al., *J. Biolumin. Chemilumin.* 10(6):353–9 (1995), the disclosures of which are incorporated herein by reference in their entireties. Kits for such enhanced chemiluminescent detection (ECL) are available commercially.

The antibodies can also be labeled using colloidal gold.

As another example, when the antibodies of the present invention are used, e.g., for flow cytometric detection, for scanning laser cytometric detection, or for fluorescent immunoassay, they can usefully be labeled with fluorophores.

There are a wide variety of fluorophore labels that can usefully be attached to the antibodies of the present invention.

For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCP-Cy5.5, PE-Cy5, PE-Cy5.5, PE-Cy7, PE-Texas Red, and APC-Cy7.

Other fluorophores include, inter alia, Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7, all of which are also useful for fluorescently labeling the antibodies of the present invention.

For secondary detection using labeled avidin, streptavidin, captavidin or neutravidin, the antibodies of the present invention can usefully be labeled with biotin.

When the antibodies of the present invention are used, e.g., for western blotting applications, they can usefully be labeled with radioisotopes, such as $^{33}P$, $^{32}P$, $^{35}S$, $^{3}H$, and $^{125}I$.

As another example, when the antibodies of the present invention are used for radioimmunotherapy, the label can usefully be $^{228}Th$, $^{227}Ac$, $^{225}Ac$, $^{223}Ra$, $^{213}Bi$, $^{212}Pb$, $^{212}Bi$, $^{211}At$, $^{203}Pb$, $^{194}Os$, $^{188}Re$, $^{186}Re$, $^{153}Sm$, $^{149}Tb$, $^{131}I$, $^{125}I$, $^{111}In$, $^{105}Rh$, $^{99m}Tc$, $^{97}Ru$, $^{90}Y$, $^{90}Sr$, $^{88}Y$, $^{72}Se$, $^{67}Cu$, or $^{47}Sc$.

As another example, when the antibodies of the present invention are to be used for in vivo diagnostic use, they can be rendered detectable by conjugation to MRI contrast agents, such as gadolinium diethylenetriaminepentaacetic acid (DTPA), Lauffer et al., *Radiology* 207(2):529–38 (1998), or by radioisotopic labeling.

As would be understood, use of the labels described above is not restricted to the application as for which they were mentioned.

The antibodies of the present invention, including fragments and derivatives thereof, can also be conjugated to toxins, in order to target the toxin's ablative action to cells that display and/or express the proteins of the present invention. Commonly, the antibody in such immunotoxins is conjugated to Pseudomonas exotoxin A, diphtheria toxin, shiga toxin A, anthrax toxin lethal factor, or ricin. See Hall (ed.), *Immunotoxin Methods and Protocols* (Methods in Molecular Biology, Vol 166), Humana Press (2000) (ISBN:0896037754); and Frankel et al. (eds.), *Clinical Applications of Immunotoxins*, Springer-Verlag New York, Incorporated (1998) (ISBN:3540640975), the disclosures of which are incorporated herein by reference in their entireties, for review.

The antibodies of the present invention can usefully be attached to a substrate, and it is, therefore, another aspect of the invention to provide antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention, attached to a substrate.

Substrates can be porous or nonporous, planar or nonplanar.

For example, the antibodies of the present invention can usefully be conjugated to filtration media, such as NHS-activated Sepharose or CNBr-activated Sepharose for purposes of immunoaffinity chromatography.

For example, the antibodies of the present invention can usefully be attached to paramagnetic microspheres, typically by biotin-streptavidin interaction, which microsphere can then be used for isolation of cells that express or display the proteins of the present invention. As another example, the antibodies of the present invention can usefully be attached to the surface of a microtiter plate for ELISA.

As noted above, the antibodies of the present invention can be produced in prokaryotic and eukaryotic cells. It is, therefore, another aspect of the present invention to provide cells that express the antibodies of the present invention, including hybridoma cells, B cells, plasma cells, and host cells recombinantly modified to express the antibodies of the present invention.

In yet a further aspect, the present invention provides aptamers evolved to bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Pharmaceutical Compositions hGDMLP-1 is important to the proper functioning of skeletal and cardiac muscle cells; defects in hGDMLP-1 expression, activity, expression, activity, distribution, localization, and/or solubility are a cause of human disease, which disease can manifest as a disorder of heart and/or skeletal muscle function.

Accordingly, pharmaceutical compositions comprising nucleic acids, proteins, and antibodies of the present invention, as well as mimetics, agonists, antagonists, or inhibitors of hGDMLP-1 activity, can be administered as therapeutics for treatment of hGDMLP-1 defects.

Thus, in another aspect, the invention provides pharmaceutical compositions comprising the nucleic acids, nucleic acid fragments, proteins, protein fusions, protein fragments, antibodies, antibody derivatives, antibody fragments, mimetics, agonists, antagonists, and inhibitors of the present invention.

Such a composition typically contains from about 0.1 to 90% by weight of a therapeutic agent of the invention formulated in and/or with a pharmaceutically acceptable carrier or excipient.

Pharmaceutical formulation is a well-established art, and is further described in Gennaro (ed.), *Remington: The Science and Practice of Pharmacy*, $20^{th}$ ed., Lippincott, Williams & Wilkins (2000) (ISBN: 0683306472); Ansel et al., *Pharmaceutical Dosage Forms and Drug Delivery Systems*, $7^{th}$ ed., Lippincott Williams & Wilkins Publishers (1999) (ISBN: 0683305727); and Kibbe (ed.), *Handbook of Pharmaceutical Excipients* American Pharmaceutical Association, $3^{rd}$ ed. (2000) (ISBN: 091733096X), the disclosures of which are incorporated herein by reference in their entireties, and thus need not be described in detail herein.

Briefly, however, formulation of the pharmaceutical compositions of the present invention will depend upon the route chosen for administration. The pharmaceutical compositions utilized in this invention can be administered by various routes including both enteral and parenteral routes, including oral, intravenous, intramuscular, subcutaneous, inhalation, topical, sublingual, rectal, intra-arterial, intramedullary, intrathecal, intraventricular, transmucosal, transdermal, intranasal, intraperitoneal, intrapulmonary, and intrauterine.

Oral dosage forms can be formulated as tablets, pills, dragees, capsules, liquids, gels, syrups, slurries, suspensions, and the like, for ingestion by the patient.

Solid formulations of the compositions for oral administration can contain suitable carriers or excipients, such as carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, sodium carboxymethylcellulose, or microcrystalline cellulose; gums including arabic and tragacanth; proteins such as gelatin and collagen; inorganics, such as kaolin, calcium carbonate, dicalcium phosphate, sodium chloride; and other agents such as acacia and alginic acid.

Agents that facilitate disintegration and/or solubilization can be added, such as the cross-linked polyvinyl pyrrolidone, agar, alginic acid, or a salt thereof, such as sodium alginate, microcrystalline cellulose, corn starch, sodium starch glycolate, and alginic acid.

Tablet binders that can be used include acacia, methylcellulose, sodium carboxymethylcellulose, polyvinylpyrrolidone (Povidone™), hydroxypropyl methylcellulose, sucrose, starch and ethylcellulose.

Lubricants that can be used include magnesium stearates, stearic acid, silicone fluid, talc, waxes, oils, and colloidal silica.

Fillers, agents that facilitate disintegration and/or solubilization, tablet binders and lubricants, including the aforementioned, can be used singly or in combination.

Solid oral dosage forms need not be uniform throughout.

For example, dragee cores can be used in conjunction with suitable coatings, such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures.

Oral dosage forms of the present invention include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Additionally, dyestuffs or pigments can be added to the tablets or dragee coatings for product identification or to characterize the quantity of active compound, i.e., dosage.

Liquid formulations of the pharmaceutical compositions for oral (enteral) administration are prepared in water or other aqueous vehicles and can contain various suspending agents such as methylcellulose, alginates, tragacanth, pectin, kelgin, carrageenan, acacia, polyvinylpyrrolidone, and polyvinyl alcohol. The liquid formulations can also include solutions, emulsions, syrups and elixirs containing, together with the active compound(s), wetting agents, sweeteners, and coloring and flavoring agents.

The pharmaceutical compositions of the present invention can also be formulated for parenteral administration.

For intravenous injection, water soluble versions of the compounds of the present invention are formulated in, or if provided as a lyophilate, mixed with, a physiologically acceptable fluid vehicle, such as 5% dextrose ("D5"), physiologically buffered saline, 0.9% saline, Hanks' solution, or Ringer's solution.

Intramuscular preparations, e.g. a sterile formulation of a suitable soluble salt form of the compounds of the present invention, can be dissolved and administered in a pharmaceutical excipient such as Water-for-Injection, 0.9% saline, or 5% glucose solution. Alternatively, a suitable insoluble form of the compound can be prepared and administered as a suspension in an aqueous base or a pharmaceutically acceptable oil base, such as an ester of a long chain fatty acid (e.g., ethyl oleate), fatty oils such as sesame oil, triglycerides, or liposomes.

Parenteral formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like).

Aqueous injection suspensions can also contain substances that increase the viscosity of the suspension, such as sodium carboxymethyl cellulose, sorbitol, or dextran. Non-lipid polycationic amino polymers can also be used for delivery. Optionally, the suspension can also contain suitable stabilizers or agents that increase the solubility of the compounds to allow for the preparation of highly concentrated solutions.

Pharmaceutical compositions of the present invention can also be formulated to permit injectable, long-term, deposition.

The pharmaceutical compositions of the present invention can be administered topically.

A topical semi-solid ointment formulation typically contains a concentration of the active ingredient from about 1 to 20%, e.g., 5 to 10%, in a carrier such as a pharmaceutical cream base. Various formulations for topical use include drops, tinctures, lotions, creams, solutions, and ointments containing the active ingredient and various supports and vehicles. In other transdermal formulations, typically in patch-delivered formulations, the pharmaceutically active compound is formulated with one or more skin penetrants, such as 2-N-methyl-pyrrolidone (NMP) or Azone.

Inhalation formulations can also readily be formulated. For inhalation, various powder and liquid formulations can be prepared.

The pharmaceutically active compound in the pharmaceutical compositions of the present inention can be provided as the salt of a variety of acids, including but not limited to hydrochloric, sulfuric, acetic, lactic, tartaric, malic, and succinic acid. Salts tend to be more soluble in aqueous or other protonic solvents than are the corresponding free base forms.

After pharmaceutical compositions have been prepared, they are packaged in an appropriate container and labeled for treatment of an indicated condition.

The active compound will be present in an amount effective to achieve the intended purpose. The determination of an effective dose is well within the capability of those skilled in the art.

A "therapeutically effective dose" refers to that amount of active ingredient—for example hGDMLP-1 protein, fusion protein, or fragments thereof, antibodies specific for hGDMLP-1, agonists, antagonists or inhibitors of hGDMLP-1—which ameliorates the signs or symptoms of the disease or prevents progression thereof; as would be understood in the medical arts, cure, although desired, is not required.

The therapeutically effective dose of the pharmaceutical agents of the present invention can be estimated initially by in vitro tests, such as cell culture assays, followed by assay in model animals, usually mice, rats, rabbits, dogs, or pigs. The animal model can also be used to determine an initial preferred concentration range and route of administration.

For example, the ED50 (the dose therapeutically effective in 50% of the population) and LD50 (the dose lethal to 50% of the population) can be determined in one or more cell culture of animal model systems. The dose ratio of toxic to therapeutic effects is the therapeutic index, which can be expressed as LD50/ED50. Pharmaceutical compositions that exhibit large therapeutic indices are preferred.

The data obtained from cell culture assays and animal studies is used in formulating an initial dosage range for human use, and preferably provides a range of circulating concentrations that includes the ED50 with little or no toxicity. After administration, or between successive administrations, the circulating concentration of active agent varies within this range depending upon pharmacokinetic factors well known in the art, such as the dosage form employed, sensitivity of the patient, and the route of administration.

The exact dosage will be determined by the practitioner, in light of factors specific to the subject requiring treatment. Factors that can be taken into account by the practitioner include the severity of the disease state, general health of the subject, age, weight, gender of the subject, diet, time and frequency of administration, drug combination(s), reaction sensitivities, and tolerance/response to therapy. Long-acting pharmaceutical compositions can be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Where the therapeutic agent is a protein or antibody of the present invention, the therapeutic protein or antibody agent typically is administered at a daily dosage of 0.01 mg to 30 mg/kg of body weight of the patient (e.g., 1 mg/kg to 5 mg/kg). The pharmaceutical formulation can be administered in multiple doses per day, if desired, to achieve the total desired daily dose.

Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Conventional methods, known to those of ordinary skill in the art of medicine, can be used to administer the pharmaceutical formulation(s) of the present invention to the patient. The pharmaceutical compositions of the present invention can be administered alone, or in combination with other therapeutic agents or interventions.

Therapeutic Methods

The present invention further provides methods of treating subjects having defects in hGDMLP-1—e.g., in expression, activity, distribution, localization, and/or solubility of hGDMLP-1—which can manifest as a disorder of heart and/or skeletal muscle function. As used herein, "treating" includes all medically-acceptable types of therapeutic intervention, including palliation and prophylaxis (prevention) of disease.

In one embodiment of the therapeutic methods of the present invention, a therapeutically effective amount of a pharmaceutical composition comprising hGDMLP-1 protein, fusion, fragment or derivative thereof is administered to a subject with a clinically-significant hGDMLP-1 defect.

Protein compositions are administered, for example, to complement a deficiency in native hGDMLP-1. In other embodiments, protein compositions are administered as a vaccine to elicit a humoral and/or cellular immune response to hGDMLP-1. The immune response can be used to modulate activity of hGDMLP-1 or, depending on the immunogen, to immunize against aberrant or aberrantly expressed forms, such as mutant or inappropriately expressed isoforms. In yet other embodiments, protein fusions having a toxi moiety are administered to ablate cells that aberrantly accumulate hGDMLP-1.

In another embodiment of the therapeutic methods of the present invention, a therapeutically effective amount of a pharmaceutical composition comprising nucleic acid of the present invention is administered. The nucleic acid can be delivered in a vector that drives expression of hGDMLP-1 protein, fusion, or fragment thereof, or without such vector.

Nucleic acid compositions that can drive expression of hGDMLP-1 are administered, for example, to complement a deficiency in native hGDMLP-1, or as DNA vaccines. Expression vectors derived from virus, replication deficient retroviruses, adenovirus, adeno-associated (AAV) virus, herpes virus, or vaccinia virus can be used—see, e.g., Cid-Arregui (ed.), *Viral Vectors: Basic Science and Gene Therapy*, Eaton Publishing Co., 2000 (ISBN: 188129935X)— as can plasmids.

Antisense nucleic acid compositions, or vectors that drive expression of hGDMLP-1 antisense nucleic acids, are administered to downregulate transcription and/or translation of hGDMLP-1 in circumstances in which excessive production, or production of aberrant protein, is the pathophysiologic basis of disease.

Antisense compositions useful in therapy can have sequence that is complementary to coding or to noncoding regions of the hGDMLP-1 gene. For example, oligonucleotides derived from the transcription initiation site, e.g., between positions −10 and +10 from the start site, are preferred.

Catalytic antisense compositions, such as ribozymes, that are capable of sequence-specific hybridization to hGDMLP-1 transcripts, are also useful in therapy. See, e.g., Phylactou, *Adv. Drug Deliv. Rev.* 44(2–3):97–108 (2000); Phylactou et al., *Hum. Mol. Genet.* 7(10):1649–53 (1998); Rossi, *Ciba Found. Symp.* 209:195–204 (1997); and Sigurdsson et al., *Trends Biotechnol.* 13(8):286–9 (1995), the disclosures of which are incorporated herein by reference in their entireties.

Other nucleic acids useful in the therapeutic methods of the present invention are those that are capable of triplex helix formation in or near the hGDMLP-1 genomic locus. Such triplexing oligonucleotides are able to inhibit transcription, Intody et al., *Nucleic Acids Res.* 28(21): 4283–90 (2000); McGuffie et al., *Cancer Res.* 60(14): 3790–9 (2000), the disclosures of which are incorporated herein by reference, and pharmaceutical compositions comprising such triplex forming oligos (TFOS) are administered in circumstances in which excessive production, or production of aberrant protein, is a pathophysiologic basis of disease.

In another embodiment of the therapeutic methods of the present invention, a therapeutically effective amount of a pharmaceutical composition comprising an antibody (including fragment or derivative thereof) of the present invention is administered. As is well known, antibody compositions are administered, for example, to antagonize activity of hGDMLP-1, or to target therapeutic agents to sites of hGDMLP-1 presence and/or accumulation.

In another embodiment of the therapeutic methods of the present invention, a pharmaceutical composition comprising a non-antibody antagonist of hGDMLP-1 is administered. Antagonists of hGDMLP-1 can be produced using methods generally known in the art. In particular, purified hGDMLP-1 can be used to screen libraries of pharmaceutical agents, often combinatorial libraries of small molecules, to identify those that specifically bind and antagonize at least one activity of hGDMLP-1.

In other embodiments a pharmaceutical composition comprising an agonist of hGDMLP-1 is administered. Agonists can be identified using methods analogous to those used to identify antagonists.

In still other therapeutic methods of the present invention, pharmaceutical compositions comprising host cells that express hGDMLP-1, fusions, or fragments thereof can be administered. In such cases, the cells are typically autologous, so as to circumvent xenogeneic or allotypic rejection, and are administered to complement defects in hGDMLP-1 production or activity.

In other embodiments, pharmaceutical compositions comprising the hGDMLP-1 proteins, nucleic acids, antibodies, antagonists, and agonists of the present invention can be administered in combination with other appropriate therapeutic agents. Selection of the appropriate agents for use in combination therapy can be made by one of ordinary skill in the art according to conventional pharmaceutical principles. The combination of therapeutic agents or approaches can act additively or synergistically to effect the treatment or prevention of the various disorders described above, providing greater therapeutic efficacy and/or permitting use of the pharmaceutical compositions of the present invention using lower dosages, reducing the potential for adverse side effects.

Transgenic Animals and Cells

In another aspect, the invention provides transgenic cells and non-human organisms comprising hGDMLP-1 nucleic acids, and transgenic cells and non-human organisms with targeted disruption of the endogenous orthologue of the human hGDMLP-1 gene.

The cells can be embryonic stem cells or somatic cells. The transgenic non-human organisms can be chimeric, nonchimeric heterozygotes, and nonchimeric homozygotes.

Diagnostic Methods

In order to diagnose, monitor, or assess predisposition to diseases caused by changes in the hGDMLP-1 gene, the nucleic acids of the present invention can be used as hybridization probes to assess the sequence and, at a grosser level, genomic structure of the hGDMLP-1 gene in samples of genomic DNA. The nucleic acids can also be used as hybridization probes to assess the levels of hGDMLP-1 mRNA in a sample derived from heart or muscle. Antibodies of the present invention can be used to assess the expression levels of hGMDLP-1 proteins in heart or muscle.

In another aspect, antibodies which specifically bind hGDMLP-1 may be used for the diagnosis of conditions or diseases characterized by expression of hGDMLP-1, or in assays to monitor patients being treated with hGDMLP-1, agonists, antagonists or inhibitors. The antibodies useful for diagnostic purposes can be prepared in the same manner as those described above for therapeutics. Diagnostic assays for hGDMLP-1 include methods which utilize the antibody and a label to detect hGDMLP-1 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and fluorescence-activated cell sorting (FACS) for measuring hGDMLP-1 are known in the art and provide a basis for diagnosing altered or abnormal levels of hGDMLP-1 expression. Normal or standard values for hGDMLP-1 expression are established by combining body fluids or cell extracts taken from normal mammalian subjects, preferably human, with antibody to hGDMLP-1 under conditions suitable for complex formation. The amount of standard complex formation may be quantified by various methods, but preferably by photometric means. Quantities of hGDMLP-1 expressed in subject, control, and disease samples from biopsied tissues are compared with the standard values. Deviation between standard and subject values establishes the parameters for diagnosing disease.

In another embodiment of the invention, the polynucleotides encoding hGDMLP-1 can be used for diagnostic purposes. The polynucleotides which can be used include oligonucleotide sequences, complementary RNA and DNA molecules, and PNAs. The polynucleotides may be used to detect and quantitate gene expression in biopsied tissues in which expression of hGDMLP-1 may be correlated with disease. The diagnostic assay may be used to distinguish between absence, presence, and excess expression of hGDMLP-1, and to monitor regulation of hGDMLP-1 levels during therapeutic intervention.

In one aspect, hybridization with PCR probes which are capable of detecting polynucleotide sequences, including genomic sequences, encoding hGDMLP-1 or closely related molecules, may be used to identify nucleic acid sequences which encode hGDMLP-1. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding hGDMLP-1, alleles, or related sequences.

Probes may also be used for the detection of related sequences, and should preferably contain at least 50% of the nucleotides from any of the hGDMLP-1 encoding sequences. The hybridization probes of the subject invention may be DNA or RNA and derived from the nucleotide sequence of SEQ ID NO:1, or from genomic sequence including promoter, enhancer elements, and introns of the naturally occurring hGDMLP-1 (SEQ ID NO:3).

Means for producing specific hybridization probes for DNAs encoding hGDMLP-1 include the cloning of nucleic acid sequences encoding hGDMLP-1 or hGDMLP-1 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding hGDMLP-1 may be used for the diagnosis of a disorder associated with expression of hGDMLP-1, in particular heart and skeletal muscle disorders.

The polynucleotide sequences encoding hGDMLP-1 may be used in Southern or northern analysis, dot blot, or other membrane-based technologies; in PCR technologies; or in dipstick, pin, ELISA assays or microarrays utilizing fluids or tissues from patient biopsies to detect altered hGDMLP-1 expression. Such qualitative or quantitative methods are well known in the art.

The nucleotide sequences encoding hGDMLP-1 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding hGDMLP-1 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of hGDMLP-1, a normal or standard profile for expression is established. This may be accomplished by combining body fluids or cell extracts taken from normal subjects, either animal or human, with a sequence, or a fragment thereof, which encodes hGDMLP-1, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding hGDMLP-1 may involve the use of PCR. Such oligomers may be chemically synthesized, generated enzymatically, or produced in vitro. Oligomers will preferably consist of two nucleotide sequences, one with sense orientation and another with antisense, employed under optimized conditions for identification of a specific gene or condition. The same two oligomers, nested sets of oligomers, or even a degenerate pool of oligomers may be employed under less stringent conditions for detection and/ or quantitation of closely related DNA or RNA sequences.

Methods which may also be used to quantitate the expression of hGDMLP-1 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5' or 3' sequence, sequential oligonucleotides which cover the full length sequence, or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5', or more preferably, at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode hGDMLP-1 may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) Human Chromosomes: A Manual of Basic Techniques, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding hGDMLP-1 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, hGDMLP-1, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between hGDMLP-1 and the agent being tested, may be measured.

Another technique for drug screening which may be used provides for high throughput screening of compounds having suitable binding affinity to the protein of interest as described in published PCT application WO84/03564. In this method, as applied to hGDMLP-1 large numbers of different small test compounds are synthesized on a solid substrate, such as plastic pins or some other surface. The test compounds are reacted with hGDMLP-1, or fragments thereof, and washed. Bound hGDMLP-1 is then detected by methods well known in the art. Purified hGDMLP-1 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding hGDMLP-1 specifically compete with a test compound for binding hGDMLP-1. In this manner, the antibodies can be used to detect the presence of any peptide which shares one or more antigenic determinants with hGDMLP-1.

In additional embodiments, the nucleotide sequences which encode hGDMLP-1 may be used in any molecular biology techniques that have yet to be developed, provided the new techniques rely on properties of nucleotide sequences that are currently known, including, but not limited to, such properties as the triplet genetic code and specific base pair interactions.

The following examples are provided by way of illustration and not by way of limitation.

EXAMPLE 1

Identification and Characterization of a cDNA Encoding a Novel Human Genome-derived Myosin-like Gene In order to identify novel human genes that predispose or contribute to diseases caused by perturbations of the cellular contractile apparatus, we undertook to mine human genomic DNA for exons particularly expressed in human cardiac and/or skeletal muscle, looking in particular for those that are part of genes that have proven refractory to prior identification efforts based upon cloning and/or sequencing of expressed transcripts.

Briefly, bioinformatic algorithms were applied to human genomic sequence data to identify putative exons. Each of the predicted exons was amplified from genomic DNA, typically centering the putative coding sequence within a larger amplicon that included flanking noncoding sequence. These genome-derived single exon probes were arrayed on a solid support and expression of the bioinformatically predicted exons assessed through a series of simultaneous two-color hybridizations to the genome-derived single exon microarrays. The approach and procedures are further described in detail in Penn et al., "Mining the Human Genome using Microarrays of Open Reading Frames," Nature Genetics 26:315–318 (2000); commonly owned and copending U.S. patent application Ser. No. 09/774,203, filed Jan. 29, 2001; and commonly owned and copending U.S. provisional patent application No. 60/207,456, filed May 26, 2000, No. 60/234,687, filed Sep. 21, 2000, and No. 60/236,359, filed Sep. 27, 2000, the disclosures of which are incorporated herein by reference in their entireties.

Using a graphical display particularly designed to facilitate computerized query of the resulting exon-specific expression data, as further described in commonly owned and copending U.S. patent application Ser. No. 09/774,203, filed Jan. 29, 2001, an exon was identified that is expressed at high levels in human heart but in none of nine other tested tissues or cell types.

FIG. 1 is a screen shot of the graphical display in which the heart-specific exon is, for purpose of exemplification, centered in the view pane. A black line, demarcated at regular intervals in megabases ("Mb"), represents a continuous stretch of human chromosome 22 ("genome sequence line"). Below the line, in a horizontal field labeled "amp", are rectangles (blue in the original display) that identify regions of chromosome 22 that were, in one or another experiment, amplified from genomic DNA. The rectangles are aligned with the genome sequence line to show the starting and ending nucleotides of the amplicons.

Moving downward in the view pane, horizontal fields are presented that show expression measured for various of the amplicons in human heart ("HEA"), brain ("BRA"), adult liver ("ADU"), HeLa cells ("HEL"), lung ("LUN"), fetal liver ("FET"), HBL100 cells ("HBL"), bone marrow ("BON"), BT4 cells ("BT4"), and placenta ("PLA"). As further described in commonly owned and copending U.S. patent application Ser. No. 09/774,203, the expression relative to control (here a pool of message from 10 tissues) is shown in the original display in shades of red and green, with green indicating expression greater than control.

As can be seen in FIG. 1, the exon centered at about 11.1052 Mb is expressed at levels above control solely (among the tested tissues and cell types) in human heart, meeting our inclusion criteria for further study.

Standard RACE (rapid amplification of cDNA ends) and RT-PCR (reverse transcription polymerase chain reaction) techniques were used to obtain overlapping cDNA clones that collectively span 8,166 nucleotides and appear to contain the entire coding region of the gene. RT-PCR and RACE techniques are described, inter alia, in Siebert et al. (eds.), *Gene Cloning and Analysis by RT-PCR*, Eaton Publishing Company/Bio Techniques Books Division, 1998 (ISBN: 1881299147); Schaefer, *Anal. Biochem.* 20:227(2):255–73 (1995); Ausubel et al. (eds.), *Short Protocols in Molecular Biology: A Compendium of Methods from Current Protocols in Molecular Biology*, 4$^{th}$ edition (April 1999), John Wiley & Sons (ISBN: 047132938X) and Sambrook et al. (eds.), *Molecular Cloning: A Laboratory Manual* (3$^{rd}$ ed.), Cold Spring Harbor Laboratory Press (2000) (ISBN: 0879695773), the disclosures of which are incorporated herein by reference in their entireties. The cDNA was sequenced on both strands using a MegaBace™ sequencer (Molecular Dynamics, Inc., Sunnyvale, Calif., USA).

FIGS. 2A–2L collectively present the sequence of the cDNA (SEQ ID NO:1) and its translation (SEQ ID NO:3). For reasons set forth below, we have denominated the novel gene hGDMLP-1.

The hGDMLP-1 cDNA spans 8166 nucleotides and contains an open reading frame from nucleotide 170 through and including nt 7876, predicting a protein of 2568 amino acids (285.3 kD absent post-translational modification). The clone appears full length, with the reading frame opening with a methionine and terminating with a stop codon before a 3' poly-A tail.

Structurally, the N-terminal 600 amino acids, as well as the C-terminal 1100 amino acids (1400–2568) are quite hydrophilic, with fully one third of the amino acids of the first 480 residues strongly acidic or basic.

Motif searches using Pfam (Washington University, St. Louis, web site), SMART (European Molecular Biology Laboratory, Heidelberg, web site), and PROSITE pattern and profile databases (Expert Protein Analysis System (ExPASy) web site), identified several known domains. A myosin head (also denominated myosin motor, large ATPase) domain is encoded by amino acid residues 566–1335; a myosin tail domain is located at residues 1422–1919. Given the presence of a myosin head and a myosin tail, we have denominated the gene "human genome-derived myosin-like protein-1" ("hGDMLP-1").

In addition to myosin head and myosin tail domains, SMART and Pfam both additionally identified an IQ domain at residues 1336–1358. The IQ domain is a short calmodulin-binding motif containing conserved Ile and Gln residues, suggesting interaction of hGDMLP-1 with calmodulin, which is known to serve as the light chain for myosins I and V.

The sequence of the hGDMLP-1 cDNA was used a BLAST query into the GenBank nr and dbEst databases. The nr database includes all non-redundant GenBank coding sequence translations, sequences derived from the 3-dimensional structures in the Brookhaven Protein Data Bank (PDB), sequences from SwissProt, sequences from the protein information resource (PIR), and sequences from protein research foundation (PRF). The dbEst (database of expressed sequence tags) includes ESTs, short, single pass read cDNA (mRNA) sequences, and cDNA sequences from differential display experiments and RACE experiments.

A number of ESTs showing strong sequence similarity to short regions of the hGDMLP-1 coding sequence were identified, as was an EST identical to exons 15 and 16 of hGDMLP-1 (EST accession no. AA993492: "ot64g05.s1 Soares_testis_NHT Homo sapiens cDNA clone IMAGE:1621592 3' similar to TR:Q92614 Q92614 MYELOBLAST KIAA0216. ;, mRNA") (spanning nt 2954–3174 according to numbering in SEQ ID NO:1).

Nonetheless, hGDMLP-1 has not previously been identified as a full length clone. Two full length genes prior-accessioned into GenBank do, however, appear to be closely related.

The first is a murine myosin gene containing a PDZ domain (mysPDZ) (GenBank accession no. BAA93660), further described by Furusawa et al., "Isolation of a novel PDZ-containing myosin from hematopoietic supportive bone marrow stromal cell lines," *Biochem. Biophys. Res. Commun.* 270(1):67–75 (2000), the disclosure of which is incorporated herein by reference in its entirety. In the region of greatest similarity—residues 477–2270 of hGDMLP-1—hGDMLP-1 and BAA93660 show 40% identity and 60% similarity at the amino acid level, with similarity scored according to the NCBI BLAST standard BLOSUM matrix (Henikoff et al., *Proc. Natl. Acad. Sci. USA* 89:10915–10919 (1992); Henikoff et al., *Proteins* 17:49–61 (1993)). This region includes both the hGDMLP myosin head domain and myosin tail domain.

hGDMLP-1 is also highly similar across the same region (residues 477–2270 of hGDMLP-1) to the human orthologue of the murine PDZ-containing myosin in mouse (accession no. BAA13206), showing 40% identity and 61% similarity to hGDMLP-1 at the amino acid level.

FIGS. 3A–3C collectively show a multiple sequence alignment of hGDMLP-1 (amino acid residues 505–2249) with BAA93660 (murine PDZ-containing myosin-like gene, residues 341–2035) and BAA13206 (human myosin heavy chain-like gene containing P-loop, residues 1–1581). Gaps are shown within a sequence as one or more dashes (-). In the consensus line underlying the three aligned sequences, "*" indicates residues that are identical or conserved in all sequences in the alignment, ":" indicates conserved substitutions, and "."=indicates semi-conserved substitutions.

Further directed comparison of hGDMLP-1 with 10 other proteins previously identified to be myosin or myosin-like confirms that hGDMLP-1 is most similar in sequence to mysPDZ. Significant similarity was also detected to human (but not murine) myocilin (myoC). FIG. 4 shows pairwise alignment of hGDMLP-1 to human myocilin (myoC). As shown, in the region of maximal similarity in amino acid sequence, 28% of residues are identical; 54% of residues are similar, with similarity scored according to the BLOSUM 62 matrix.

Both mysPDZ and myoC are cytoskeleton-associated proteins. MyoC is associated with glaucoma, has a secreted form, and is found in association with cilia in photoreceptor cells. Based upon these sequence similarities, hGDMLP-1 is a myosin-like protein that is cytoskeleton-associated.

Separately querying GenBank with sequence drawn from the hydrophilic N-terminus and C-terminus of hGDMLP-1, the N-terminal region (112–515) is seen to have some sequence similarity to collagen alpha and other hydrophilic proteins (such as cylicin and neurofilament triplet H protein), whereas the C-terminal end of the protein is unique.

EXAMPLE 2

Identification and Characterization of a Genomic Region Encoding hGDMLP-1

Figure 5:
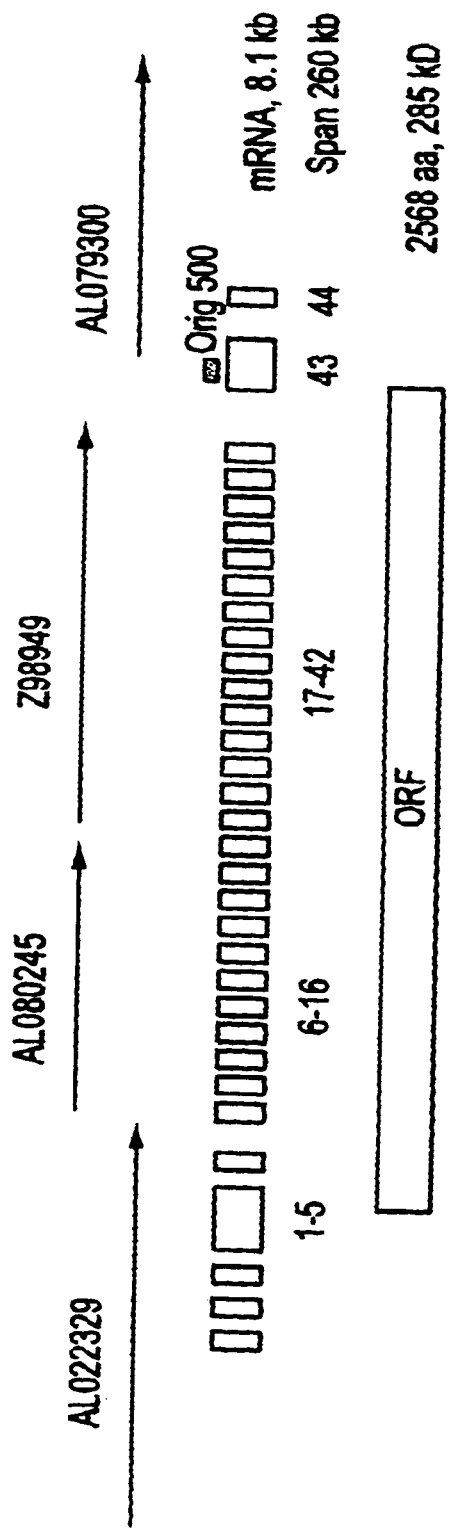
FIG. 5 schematizes the genomic organization of the hGDMLP-1 gene, showing the relative location and size of the 44 exons of the protein and their relationship to the genomic clones (BACs) and cDNA open reading frame.

BLAST query of genomic sequence identified four BACs that constitute the minimum set of clones encompassing the cDNA sequence (FIG. 5).

Based upon the known origin of the four BACs (AL022329, AL080245, Z98949 and AL079300) that encompass hGDMLP-1, the gene can be mapped to human chromosome 22q11.2, about 1 Mb distal to the 22q11 low copy repeat region.

Comparison of the cDNA and genomic sequences identified 44 exons, occupying a 288 kb region on chromosome 22q11.2. Exon organization is listed in Table 1.

TABLE I hGDMLP-1 Exon Structure

| Exon no. | cDNA range | genomic range | BAC accession |
|---|---|---|---|
| 1 | 1–60 | 192976–193035 | AL022329.9 |
| 2 | 61–208 | 211726–211873 | |
| 3 | 209–367 | 213973–214131 | |
| 4 | 368–1681 | 218857–220170 | |
| 5 | 1682–1748 | 220852–220918 | |
| 6 | 1749–1861 | 206–318 | AL080245.14 |
| 7 | 1862–2038 | 1668–1844 | |
| 8 | 2039–2237 | 6917–7115 | |
| 9 | 2238–2380 | 9390–9532 | |
| 10 | 2381–2481 | 11068–11168 | |
| 11 | 2482–2545 | 14762–14825 | |
| 12 | 2546–2690 | 27287–27431 | |
| 13 | 2691–2864 | 52839–53012 | |
| 14 | 2865–2955 | 55743–55833 | |
| 15 | 2956–3148 | 58110–58302 | |
| 16 | 3149–3229 | 62251–62331 | |
| 17 | 3230–3380 | 560–710 | Z98949.1 |
| 18 | 3381–3540 | 9002–9161 | |
| 19 | 3541–3724 | 11367–11550 | |
| 20 | 3725–3947 | 12697–12919 | |
| 21 | 3948–4057 | 16737–16846 | |
| 22 | 4058–4123 | 33587–33652 | |
| 23 | 4124–4252 | 39553–39681 | |
| 24 | 4253–4396 | 41456–41599 | |
| 25 | 4397–4486 | 43226–43315 | |
| 26 | 4487–4606 | 56023–56142 | |
| 27 | 4607–4715 | 56571–56679 | |
| 28 | 4716–4840 | 60423–60547 | |
| 29 | 4841–4995 | 63574–63728 | |
| 30 | 4996–5119 | 67880–68003 | |
| 31 | 5120–5320 | 68898–69098 | |
| 32 | 5321–5431 | 73589–73699 | |
| 33 | 5432–5536 | 76213–76317 | |
| 34 | 5537–5689 | 86524–86676 | |
| 35 | 5690–5803 | 111403–111516 | |
| 36 | 5804–5920 | 112978–113094 | |
| 37 | 5921–6004 | 115633–115716 | |
| 38 | 6005–6142 | 117552–117689 | |
| 39 | 6143–6328 | 120445–120630 | |
| 40 | 6329–6459 | 157629–157759 | |
| 41 | 6460–6504 | 168531–168575 | |
| 42 | 6505–6642 | 169984–170121 | |
| 43 | 6643–7888 | 18298–19543 | AL079300.11 |
| 44 | 7889–8090 | 22296–22497 | |

EXAMPLE 3

Expression and Transcription Control of hGDMLP-1

Exons 1, 3, 4, 7, 8, 9, 15, 20, 24, 31, 39, 43, and 44 of hGDMLP-1 were separately amplified and the genome-derived single-exon probes arrayed for expression analysis essentially as described in Penn et al., "Mining the Human Genome using Microarrays of Open Reading Frames," *Nature Genetics* 26:315–318 (2000) and commonly owned and copending U.S. patent application Ser. No. 09/774,203, filed Jan. 29, 2001, the disclosures of which are incorporated herein by reference in their entireties.

Table 2 reports the results of hybridization experiments. "Amplicon" is a unique designation. "Signal" indicates normalized signal intensity. "Ratio" is the ratio of expression relative to control. "ND" indicates "not determined".

TABLE 2

| | $Amp_{13}$ 2534, exon 1 | | $Amp_{13}$ 2541, exon 3 | | $Amp_{13}$ 2540, exon 3 | | $Amp_{13}$ 38, exon 4 | | $Amp_{13}$ 10400, exon 4 | | $Amp_{13}$ 11966, exon 4 | |
|---|---|---|---|---|---|---|---|---|---|---|---|---|
| | SIGNAL | RATIO | SIGNAL | RATIO | SIGNAL | RATIO | SIGNAL | RATIO | SIGNAL | RATIO | SIGNAL | RATIO |
| ADRENAL | 0.71 | 1.43 | 0.94 | | 0.7 | 1.15 | 4.12 | | ND | ND | ND | ND |
| ADULT LIVER | 0.52 | 1.13 | 0.46 | | 0.59 | 1.11 | 6.54 | −1.28 | 1.56 | | 2.41 | |
| BONE MARROW | 0.71 | | 0.77 | | 0.95 | | | −1.29 | 1.77 | −1.15 | 2.35 | 1.08 |
| BRAIN | 0.52 | −1.06 | | | 0.83 | −1.37 | | −1.58 | 1.8 | −1.15 | 1.75 | −1.23 |
| FETAL LIVER | 0.49 | | 0.47 | 1.29 | 0.72 | 1.06 | | −1.3 | 1.49 | | 2.47 | −1.28 |
| HEART | 1.86 | 3.33 | 2.01 | 3.13 | 2.52 | 2.77 | 6.23 | −1.05 | 2.9 | 1.36 | 3.16 | −1.02 |
| HELA | 0.71 | | 0.72 | −1.02 | 0.82 | 1.03 | 6.08 | −1.11 | 1.91 | 1.11 | 2.07 | −1.01 |
| KIDNEY | 0.61 | −1.11 | 0.66 | 1.01 | 0.81 | | 6.71 | −1.09 | ND | ND | ND | ND |
| LUNG | 0.66 | −1.2 | 0.73 | −1.06 | 0.83 | −1.02 | 7.15 | −1.02 | 0.99 | −1.38 | 1.95 | −1.05 |
| PLACENTA | 0.46 | | 0.55 | 2.59 | 0.57 | | | | 2.09 | 1.02 | 2.2 | −1.12 |
| PROSTATE | 0.26 | | 0.58 | −1.11 | 0.58 | 1.15 | | −1.16 | ND | ND | ND | ND |
| SKELKTAL MUSCLE | 9.61 | 6.61 | 3.38 | 5.14 | 4.04 | | 8.12 | 1.04 | ND | ND | ND | ND |

TABLE 2-continued

| | Amp₁₃ 33835, exon 7 | | Amp₁₃ 9715, exon 7 | | Amp₁₃ 73301, exon 8 | | Amp₁₃ 73302, exon 9 | | Amp₁₃ 33836, exon 15 | | Amp₁₃ 10252, exon 15 | |
|---|---|---|---|---|---|---|---|---|---|---|---|---|
| | SIGNAL | RATIO | SIGNAL | RATIO | SIGNAL | RATIO | SIGNAL | RATIO | SIGNAL | RATIO | SIGNAL | RATIO |
| ADRENAL | 2.72 | −1.72 | ND | ND | 0.87 | −1.02 | 3.43 | 1.22 | 0.84 | 1.3 | ND | ND |
| ADULT LIVER | 3.32 | −1.76 | 2.88 | | 1.14 | −1.27 | 3.88 | 1.21 | | 1.22 | 1.28 | |
| BONE MARROW | 2.53 | −1.85 | 2.99 | −1.22 | 0.79 | | 3.68 | 1.06 | 0.64 | 1.34 | 1.68 | −1.1 |
| BRAIN | 2.46 | −1.61 | 3.92 | 1.09 | 0.66 | −1.29 | 4.28 | 1.57 | 0.67 | 1.32 | 1.86 | −1.08 |
| FETAL LIVER | 2.39 | −1.77 | 3.14 | −1.2 | 0.89 | 1.08 | 4.28 | 1.33 | 0.78 | 1.5 | 1.31 | −1.27 |
| HEART | 2.13 | −2.04 | 3.05 | −1.18 | 1.38 | | 3.19 | −1.09 | | 1.75 | 1.9 | 1.26 |
| HELA | 2.71 | −1.65 | 3.05 | −1.17 | 0.89 | −1.12 | 3.45 | 1.03 | 0.64 | | 1.36 | −1.09 |
| KIDNEY | 2.79 | −1.85 | ND | ND | 1.22 | 1.11 | 3.99 | 1.03 | 0.71 | −1.09 | ND | ND |
| LUNG | 2.97 | −1.82 | 2.59 | −1.15 | 0.9 | −1.13 | 3.83 | 1.33 | 0.71 | | 1.03 | −1.33 |
| PLACENTA | 2.98 | −1.69 | 3.19 | −1.05 | 1.14 | | 4.1 | 1.29 | 0.84 | 1.09 | 1.37 | −1.23 |
| PROSTATE | 2.89 | −1.39 | ND | ND | 0.97 | 1.05 | 3.89 | 1.38 | 0.75 | | ND | ND |
| SKELETAL MUSCLE | 2.14 | −1.97 | ND | ND | 2.49 | 2.04 | 3.08 | −1.04 | | | ND | ND |

| | Amp₁₃ 92329, exon 20 | | Amp₁₃ 92328, exon 24 | | Amp₁₃ 92327, exon 31 | | Amp₁₃ 92326, exon 39 | | Amp₁₃ 40, exon 43 | | Amp₁₃ 5271, exon 43 | |
|---|---|---|---|---|---|---|---|---|---|---|---|---|
| | SIGNAL | RATIO | SIGNAL | RATIO | SIGNAL | RATIO | SIGNAL | RATIO | SIGNAL | RATIO | SIGNAL | RATIO |
| ADRENAL | 0.59 | 1.34 | 3.96 | 1.3 | 0.46 | | 2.14 | 1.01 | | | ND | ND |
| ADULT LIVER | 0.63 | 1.56 | 6.05 | 1.54 | 0.44 | 2.83 | 2.67 | 1.06 | 0.82 | | 0.56 | −1.22 |
| BONE MARROW | 0.5 | | | 1.34 | | | 2.05 | −1.15 | | | 0.42 | −3.09 |
| BRAIN | | | | | 0.46 | | 2.1 | 1.15 | 0.99 | 1.28 | 0.44 | 1.13 |
| FETAL LIVER | 0.69 | 2.01 | 4.47 | 1.35 | 0.33 | | 2.01 | −1.08 | 0.72 | 1.07 | 0.48 | |
| HEART | 0.67 | 1.49 | 4.32 | 1.17 | | | 2.95 | 1.37 | | | | |
| HELA | 0.61 | 1.57 | 4.55 | 1.37 | 0.42 | | 2 | −1.05 | 0.9 | 1.08 | 0.39 | |
| KIDNEY | 0.65 | | 5.68 | 1.28 | 0.5 | | 3.55 | 1.15 | 0.99 | 1.34 | ND | ND |
| LUNG | 0.65 | 2.85 | 4.1 | 1.42 | 0.42 | | 2.09 | 1.09 | | 1.75 | 0.47 | −1.32 |
| PLACENTA | | | 3.59 | 1.4 | 0.48 | | 2.44 | −1.02 | 0.71 | 1.85 | 0.42 | −1.23 |
| PROSTATE | 0.67 | 1.41 | 3.07 | 1.43 | 0.49 | | 2.23 | 1.09 | 0.73 | | ND | ND |
| SKELETAL MUSCLE | 0.66 | | 3.95 | 1.26 | 0.69 | | 3.1 | 1.59 | 15.04 | | ND | ND |

| | Amp₁₃ 5272, exon 43 | | Amp₁₃ 5273, exon 43 | | Amp₁₃ 2920, exon 44 | |
|---|---|---|---|---|---|---|
| | SIGNAL | RATIO | SIGNAL | RATIO | SIGNAL | RATIO |
| ADRENAL | ND | ND | ND | ND | | 1.07 |
| ADULT LIVER | 0.55 | −1.48 | 0.57 | −2.46 | 1.3 | −1.34 |
| BONE MARROW | 0.54 | | 0.51 | −1.93 | 1.32 | −1.14 |
| BRAIN | 0.49 | | 0.48 | −4.19 | | −1.3 |
| FETAL LIVER | 0.53 | −1.64 | 0.78 | −3.56 | 1.2 | −1.5 |
| HEART | | 5.74 | | 6.44 | | |
| HELA | 0.52 | | 0.45 | | 1.13 | 1 |
| KIDNEY | ND | ND | ND | ND | 1.08 | −1.01 |
| LUNG | 0.67 | −1.04 | 0.65 | | | −1.14 |
| PLACENTA | 0.48 | 1.87 | | | | −1.36 |
| PROSTATE | ND | ND | ND | ND | | 1.44 |
| SKELETAL MUSCLE | ND | ND | ND | ND | 3.6 | |

ND = NOT DETERMINED

As can be seen in table 2, skeletal muscle and heart are the primary locations of hGDMLP-1 expression.

Heart and skeletal muscle-specific expression was further confirmed by northern blot analysis using amplicon 40 (exon 43) as probe. As shown in FIG. 6, of the 12 tissues assayed—blood, leukocytes, lung, placenta, small intestine, liver, kidney, spleen, thymus, colon, skeletal muscle, heart and brain—only skeletal muscle and heart demonstrate expression, with both having an 8 kb transcript.

Possession of the genomic sequence permitted search for promoter and other control sequences for the hGDMLP-1 gene.

A putative transcriptional control region, inclusive of promoter and downstream elements, was defined as 2 kb around the transcription start site, itself defined as the first nucleotide of the cDNA clone. The region, drawn from sequence of BAC AL022329, has the following sequence, where nucleotide number 1001 is the transcription start site:

(SEQ ID NO:15,752)
tgattttttttttttttttgagatggagtctctctctgtcaccc aggctggagtgcagtggcgcgatctcggcttactgcaagctccgc ctgtagctgggactacaggcgcccaccaccacgcccggctaattt tgtttttgtattttagtagagacggggtttcactgtgttagcca ggatggtctcaatctcctgacctcgtgatatgcccacctcggctt cccaaagtgccgggattacagacgtgagccaccgtgccaggccca aagcacttttttatagcccctagtttgctgttgtgtctgtttcct -continued

```
ctacggcccgcacagcctgggtttgaattctggctctccatggcc
ttgggcaagttggttaacttttttgtgtctcaatttccccacttgt
aaagtggggctggggaaaaaccctacctcatagggaacattaagt
gagttcatgaaagccctcggtgtgtggcatgcgataaccactacc
taagcataaggtatgtttacatgcactggttgtttaccacgacgc
accagcattcattcaagttattttcttccagagtctgcctggaat
gtagaaccggccagctctcctcotcaaacagttcctgcaacctct
ggttatctgtgtgggcagaggcgggagtgtgggtgtgtggccctg
ccctgggacagggatgacgagagagcatgtgcttgtgtccagagc
tgtccccttccctgctcagggggccaccaaatatgtccatggtctc
tgctgcctggtcaacggccacccccgggctgccgtctcctggccag
acctggagctcacaagctaattttagaaatgactggtcgactcag
ctgctgctatcacattggcccagaaggagggtgggggggaggacgg
gtcggggaggggcagtaagggggaagggatgtgtgtcggtgtgtgt
ggagagGGTGCTCCTTCGCTCCTGCTTTCCCGGCTCGGTGGGGTC
CCTTCGCGGCcacccggggagacgtcttagacagtcgtggttcct
gtgatctgtgtcctctttgcagaaggtactattgggctgggtttt
agacgggcaccttgcgagcggatcggcgagttttaattttccgga
atgogctgctgggggctgcggtggcaggcctccggtcttttggtc
tattttaggcctttctggtgttgagagcttccgaggcctgattcc
tttgcctgttgcccgtgctgctcactttgaaaacaagagtgtttc
ggtggaaggatttgagaacaaaatgctggggcaaatggacattcg
taagaatcactctcctcaggccccagctgttcgctaataatttt
aaaaatgtgtttagaatcatgagttaatctccactgtgaatcttt
gcccgcagacgtcagggtttatatttttcctcaactaccagtaat
ttctgcttcactggtgttcagttatggtcggggaagagccaggct
tcccctttcgtgttaacaacgctgttgagtcgaaatgttaatttt
aatgttcttttttaaactgcaaattaagcatgtatgagtgttggg
ggaagggcaatggaagttcatggctgaaggtttcaatttcatgcc
accttccttgagctctgtctgagggaaggtgtcttatctggcacc
ccggatagcaggcatttctctgaatgaagaagattcacaggtccc
agtggcccatagtggggcagaaggggggctatgctttgacatgga
gctctctcccaggagaggagaagacctcaccagctacaggcctct
gggctgctgccttcctgcagcttttccatggaggaggccaggagt
ggggaggcccggaatggggagcccagtcggctcccagtcggctcc
aagctgtccagtctggcctcaacccgcaagtgtgggggatctgggc
ttctatcctgtagggcctggaatacgacgaggctgttactttcac
tttgtggctgtccaaaaaga
```

Using PROSCAN, available at the National Institutes of Health web site, no significant promoter was identified in the putative promoter region. However, transcription factor binding sites were identified using MOTIF, available at the GenomeNet web site (Bioinformatics Center, Institute for Chemical Research, Kyoto University), including a SRY (sex-determining region Y gene product) binding sites (134. .140 bp, with numbering according to SEQ ID NO:15,752), and a couple of MZF1 (myeloid zinc finger 1, a negative regulator of CD34 and c-myb, and responsive to retinoic acid) binding sites (1843. .1850 bp and 403–395 bp).

EXAMPLE 4 hGDMLP-1 Disease Associations

Defects in hGDMLP-1 function and/or expression contribute to human disease. Predisposition to such diseases, presence of disease (diagnosis), and monitoring of the course of the disease can therefore be effected using the hGDMLP-1-specific diagnostic compositions and methods provided herein. Accordingly, treatment of such diseases can be effected using the hGDMLP-1-specific therapeutic compositions and methods provided herein.

Diseases that map to the hGDMLP-1 chromosomal region are shown in Table 3.

TABLE 3

Co-mapping Diseases

| OMIM No. | name | map location |
|----------|------|--------------|
| 115470 | cat eye syndrome | 22q11 |
| 217095 | conotruncal cardiac anomalies | 22q11 |
| 192430 | DiGeorge syndrome (2); Velocardiofacial syndrome | 22q11 |
| 604364 | Epilepsy, partial, with variable foci | 22q11–q12 |
| 600850 | Schizophrenia susceptibility locus, chromosome 22-related | 22q11–q13 |
| 155100 | May-Hegglin anomaly | 22q11.2 |
| 153640 | Fechtner syndrome | 22q11.2 |
| 605249 | Sebastian syndrome | 22q11.2 |
| 603622 | Deafness, autosomal dominant 17 | 22q11.2 |
| 145410 | Opitz G syndrome, type II | 22q11.2 |
| 601547 | Cataract, cerulean, type 2 | 22q11.2–q12.2 |

A number of these diseases have physiologic characteristics consistent with alteration of a myosin-like gene, especially a myosin-like gene particularly expressed in human heart.

Thus, the iris alterations that give cat eye syndrome (CES) its name are frequently associated with heart malformations. A small supernumerary chromosome (smaller than chromosome 21) is present, frequently has 2 centromeres, is bisatellited, and represents an inv dup(22)(q11). No gene candidates have been identified as yet.

Individuals with 22q11 deletion syndrome (del 22q11) have a range of findings, including congenital heart disease (74% of patients), particularly conotruncal malformations (tetralogy of Fallot, interrupted aortic arch, and truncus arteriosus); palatal abnormalities (69%), particularly velopharyngeal incompetence (VPI), submucosal cleft palate, and cleft palate; characteristic facial features (present in the majority of individuals); and learning difficulties (70–90%).

DiGeorge syndrome (DGS), most cases of which result from a deletion of chromosome 22q11.2, is characterized by hypocalcemia arising from parathyroid hypoplasia, thymic hypoplasia, and outflow tract defects of the heart. This syndrome has previously been considered to be a contiguous gene deletion, but one or a few genes in the identified locus may play a major role in the pathogenesis of the syndrome's characteristic phenotypic features. Several genes are lost in the characteristic deletion, but definitive identification of the causative genes is lacking.

Several disorders have been tentatively linked to another myosin-like gene that maps to 22q11, MYH9, although some of these associations are inferential and may be due instead to mutations in hGDMLP-1.

For example, the autosomal dominant giant-platelet disorders May-Hegglin anomaly, Fechtner syndrome, and Sebastian syndrome share the triad of thrombocytopenia, large platelets, and characteristic leukocyte inclusions. All three disorders may be allelic since May-Hegglin anomaly and Fechtner syndrome map to an overlapping region of 480 kb on chromosome 22. MYH9 was recently identified as a possible candidate gene, since MYH9 is expressed in platelets and is upregulated during granulocyte differentiation, but association of the disease with MYH9 is inferential. Kelley et al., *Nature Genetics* 26:106–108 (2000).

Other disorders that map to 22q11 may result from defects of hGDMLP-1, although primary disease manifestions are not in cardiac or skeletal muscle.

For example, Xiong et al., *Am. J. Hum. Genet.* 65:1698–1710 (1999), mapped the disease locus for a familial partial epilepsy syndrome with variable foci to an interval on 22q11-q12. The syndrome is characterized by mostly nocturnal seizures arising from frontal, temporal, and occasionally occipital epileptic foci. The syndrome is inherited as an autosomal dominant trait with incomplete penetrance.

Several studies have suggested that there may be a susceptibility locus for schizophrenia located on chromosome 22. Gill et al., *Am. J. Med. Genet.* 67:40–5 (1996). Additionally, Pulver et al. (1994) reported a higher incidence of schizophrenia among patients with velocardiofacial syndrome, which is localized to 22q11. Candidate genes have not yet been identified.

Opitz G syndrome, Opitz et al., *Birth Defects Orig. Art. Ser.* 2: 95–101 (1969), is characterized by hypertelorism or telecanthus; laryngotracheoesophageal cleft; clefts of lip, palate, and uvula; swallowing difficulty and hoarse cry; genitourinary defects, especially hypospadias in males and splayed labia majora in females; mental retardation; and congenital heart defects. Opitz Syndrome may also be characterized by additional abnormalities, including partial or complete closure of the anal opening (imperforate anus); hypoplasia or agenesis of the corpus callosum; renal abnormalities; heart defects; or mental retardation. Although Opitz G syndrome has been mapped to 22q11.2, no specific genes have been associated with the disease. See, e.g., Robin et al., *Am. J. Med. Genet.* 62: 305–317 (1996).

Congenital cataracts are responsible for between 10 and 30% of all cases of blindness in children. One of these congenital forms is cerulean cataract which has been mapped to 22q11.2-22q12.2. The beta-crystallin genes have been identified as possible candidate genes, but no definitive association has been shown.

In addition, diseases not yet shown to map to the hGDMLP-1 chromosomal locus will be shown to be attributable to hGDMLP-1 defects.

Diseases of the heart and vascular system are a significant cause of human morbidity and mortality. Increasingly, genetic factors are being found that contribute to predisposition, onset, and/or aggressiveness of most, if not all, of these diseases. Although mutations in single genes have on occasion been identified as causative, these disorders are for the most part believed to have polygenic etiologies.

For example, cardiovascular disease (CVD), which includes coronary heart disease, stroke, and peripheral arterial vascular disease, is the leading cause of death in the United States and other developed countries. In developing regions, coronary heart disease and stroke are ranked second and third, respectively, as causes of mortality. In the United States alone, about 1 million deaths (about 42% of total deaths per year) result from CVD each year. CVD is also a significant cause of morbidity, with about 1.5 million people suffering myocardial infarction, and about 500,000 suffering strokes in the United States each year. With risk for CVD increasing with age, and an increasingly aging population, CVD will continue to be a major health problem into the future.

CVD is caused by arterial lesions that begin as fatty streaks, which consist of lipid-laden foam cells, and develop into fibrous plaques. The atherosclerotic plaque may grow slowly, and over several decades may produce a severe stenosis or result in arterial occlusion. Some plaques are stable, but other, more unstable, ones may rupture and induce thrombosis. The thrombi may embolize, rapidly occluding the lumen and leading to myocardial infarction or acute ischemic syndrome.

Risk factors for CVD include age and gender. In addition, a family history of CVD significantly increases risk, indicating a genetic basis for development of this disease complex. Obesity, especially truncal obesity, the cause of which is suspected to be genetic, is yet another risk factor for CVD. Familial disorders such as hyperlipidemia, hypoalphalipoproteinemia, hypertriglyceridemia, hypercholesterolemia, hyperinsulinemia, homocystinuria, and dysbetalipoproteinemia, all of which lead to lipid or lipoprotein abnormalities, can predispose one to the development of CVD. Both insulin-dependent and non-insulin-dependent diabetes mellitus, both of which have genetic components, have been also linked to the development of atherosclerosis.

The literature is replete with evidence for genetic causes of cardiovascular diseases. For example, studies by Allayee et al., *Am. J. Hum. Genet.* 63:577–585(1998), indicated a genetic association between familial combined hyperlipidemia (FCHL) and small dense LDL particles. The studies also concluded that the genetic determinants for LDL particle size are shared, at least in part, among FCHL families and the more general population at risk for CVD. Juo et al., *Am. J. Hum. Genet.* 63: 586–594 (1998) demonstrated that small, dense LDL particles and elevated apolipoprotein B levels, both of which are commonly found in members of FCHL families, share a common major gene plus individual polygenic components. The common major gene was estimated to explain 37% of the variants of adjusted LDL particle size and 23% of the variants of adjusted apoB levels.

The atherogenic lipoprotein phenotype (ALP) is a common heritable trait, symptoms of which include a prevalence of small, dense LDL particles, increased levels of triglyceride-rich lipoproteins, reduced levels of high density lipoprotein, and increased risk of CVD, particularly myocardial infarction. Both Nishina et al., *Proc. Nat. Acad. Sci.* 89: 708–712 (1992) and Rotter et al., *Am. J. Hum. Genet.* 58: 585–594(1996) demonstrated linkage between ALP and the LDLR locus. Rotter et al., supra, also reported linkage to the CETP locus on chromosome 16 and to the SOD1 locus on chromosome 6, and possibly also to the APOA1/APOC3/APOA4 cluster on chromosome 11.

Mutations in genes identified as components of lipid metabolism, e.g., apolipoprotein E (apoE) and LDL receptor (LDLR), have been shown to be associated with predisposition to the development of CVD. For example, several apoE variants had been found to be associated with familial dysbetalipoproteinemia, characterized by elevated plasma cholesterol and triglyceride levels and an increased risk for atherosclerosis (de Knijff et al., *Mutat* 4: 178–194 (1994)). Mutations in the LDLR gene have been associated with the familial hypercholesterolemia, an autosomal dominant disorder characterized by elevation of serum cholesterol bound to low density lipoprotein (LDL), that can lead to increased susceptibility to CVD.

To date, mutations in numerous genes have been shown to be associated with increased CVD susceptibility. However, the identified genetic associations are believed not to account for all genetic contributions to CVD.

As yet another example, hypertension is a major health problem because of its high prevalence and its association with increased risk of CVD. Approximately 25% of all adults and over 60% of persons older than 60 years in the United States have high blood pressure.

Arterial or systemic hypertension is diagnosed when the average of two or more diastolic BP measurements on at least two subsequent visits is 90 mm Hg or more, or when the average of multiple systolic BP readings on two or more subsequent visits is consistently greater than 140 mm Hg. Pulmonary hypertension is defined as pressure within the pulmonary arterial system elevated above the normal range; pulmonary hypertension may lead to right ventricle (RV) failure.

Hypertension, together with other cardiovascular risk factors, leads to atherosclerosis and other forms of CVD, primarily by damaging the vascular endothelium. In more than 40% of the U.S. population, hypertension is accompanied by hyperlipidemia and leads to the development of atherosclerotic plaques. In the absence of hyperlipidemia, intimal thickening occurs. Non-atherosclerotic hypertension-induced vascular damage can lead to stroke or heart failure.

Familial diseases associated with secondary hypertension include familial renal disease, polycystic kidney disease, medullary thyroid cancer, pheochromocytoma, and hyperparathyroidism. Hypertension is also twice as common in patients with diabetes mellitus.

More than 95% of all hypertension cases are essential hypertension, that is, lack identifiable antecedent clinical cause. Essential hypertension shows clustering in families and can result from a variety of genetic diseases. In most cases, high blood pressure results from a complex interaction of factors with both genetic and environmental components. The recent search for genes that contribute to the development of essential hypertension has shown that the disorder is polygenic in origin. However, with several exceptions (such as angiotensinogen, angiotensin receptor-1, beta-3 subunit of guanine nucleotide-binding protein, tumor necrosis factor receptor-2, and α-adducin), the particular genes involved are still being sought.

Susceptibility loci for essential hypertension have been mapped to chromosomes 17 and 15q. Hasstedt et al., *Am. J. Hum. Genet.* 43: 14–22 (1988) measured red cell sodium in 1,800 normotensive members of 16 Utah pedigrees ascertained through hypertensive or normotensive probands, siblings with early stroke death, or brothers with early coronary disease, and suggested that red blood cell sodium was determined by 4 alleles at a single locus. This major locus was thought to explain 29% of the variance in red cell sodium, and polygenic inheritance explained another 54.6%.

A higher frequency of the high red blood cell sodium genotype in pedigrees in which the proband was hypertensive rather than normotensive provided evidence that this major locus increases susceptibility to hypertension.

From a study of systolic blood pressure in 278 pedigrees, Perusse et al., *Am. J. Hum. Genet.* 49: 94–105 (1991) reported that variability in systolic blood pressure is likely influenced by allelic variation of a single gene, with gender and age dependence. They also suggested that a single gene may be associated with a steeper increase of blood pressure with age among males and females.

There is strong evidence, however, for additional as yet uncharacterized, hypertension-associated loci on other chromosomes.

For example, Xu et al., *Am. J. Hum. Genet.* 64: 1694–1701 (1999) carried out a systematic search for chromosomal regions containing genes that regulate blood pressure by scanning the entire autosomal genome using 367 polymorphic markers. Because of the sampling design, the number of sib pairs, and the availability of genotyped parents, this study represented one of the most powerful of its kind. Although no regions achieved a 5% genomewide significance level, maximum lod scores were greater than 2.0 for regions of chromosomes 3, 11, 15, 16, and 17.

As another example, cardiac arrhythmias account for several thousand deaths each year. Arrhythmias such as ventricular fibrillation, which causes more than 300,000 sudden deaths annually in the United States alone, encompass a multitude of disorders. Another type of arrhythmia, idiopathic dilated cardiomyopathy, of which familial dilated cardiomyopathy accounts for 20–25%, is responsible for more than 10,000 deaths in the United States annually and is the predominant indication for cardiac transplantation.

Cardiac arrhythmias can be divided into bradyarrhythmias (slowed rhythms) or tachyarrhythmias (speeded rhythms). Bradyarrhythmias result from abnormalities of intrinsic automatic behavior or conduction, primarily within the atrioventricular node and the His-Purkinje's network. Tachyarrhythmias are caused by altered automaticity, reentry, or triggered automaticity.

Bradyarrhythmias arising from suspected polygenic disorders include Long QT syndrome 4, atrioventricular block, familial sinus node disease, progressive cardiac conduction defect, and familial cardiomyopathy. Tachyarrhythmias with possible underlying polygenic causes include familial ventricular tachycardia, Wolff-Parkinson-White syndrome, familial arrhythmogenic right ventricular dysplasia, heart-hand syndrome V, Mal de Meleda, familial ventricular fibrillation, and familial noncompaction of left ventricular myocardium.

For some of the arrhythmias, one or more of the causative genes have been identified.

For example, atrioventricular block has been associated with mutations in the SCN5A gene, as well as mutations in a locus mapped to 19q13. Studies have shown linkage of familial sinus node disease to a marker on 10q22-q24. Familial ventricular tachycardia has been linked to mutations in genes encoding the G protein subunit alpha-i2 (GNAI1), and/or related genes. Examination of families with Wolff-Parkinson-White syndrome suggest an autosomal dominant pattern of inheritance and evidence of linkage of the disorder to DNA markers on band 7q3. Linkage analysis shows strong evidence for localization of a gene for Mal de Meleda disease on 8qter. Familial ventricular fibrillation can be caused by mutations in the cardiac sodium channel gene SCN5A. Familial noncompaction of left ventricular myocardium has been linked to mutations in the gene encoding tafazzin (TAZ), or in the FK506-binding protein 1A gene (FKBP1A).

Familial dilated cardiomyopathy is characterized by an autosomal dominant pattern of inheritance with age-related penetrance. The linkage of familial dilated cardiomyopathy to several loci indicate that it is polygenic. These loci include CMD1A on 1p11-q11, CMD1B on 9q13, CMD1C on 10q21, CMD1D on 1q32, CMD1E on 3p, CMD1F on 6q, CMD1G on 2q31, CMD1H on 2q14-q22, and CMDLI, which results from mutation in the DES gene on 2q35. In addition, cardiomyopathy can also be caused by mutations in the ACTC gene, the cardiac beta-myosin heavy chain gene (MYH7), or the cardiac troponin T gene.

Familial arrhythmogenic right ventricular dysplasia is inherited as an autosomal dominant with reduced penetrance and is one of the major genetic causes of juvenile sudden death. It is estimated that the prevalence of familial arrhythmogenic right ventricular dysplasia ranges from 6 per 10,000 in the general population to 4.4 per 1,000 in some areas. Several loci for familial arrhythmogenic right ventricular dysplasia have been mapped indicating that this disease is also polygenic in nature. These loci include ARVD1 on 14q23-q24, ARVD2 on 1q42-q43, ARVD3 on 14q12-q22, ARVD4 on 2q32.1-q32.3, ARVD5 on 3p23, and ARVD6 on 10p14-p12.

Progressive cardiac conduction defect (PCCD), also called Lenegre-Lev disease, is one of the most common cardiac conduction diseases. It is characterized by progressive alteration of cardiac conduction through the His-Purkinje system with right or left bundle branch block and widening of QRS complexes, leading to complete atrioventricular block and ultimately causing syncope and sudden death. It represents the major cause of pacemaker implantation in the world (0.15 implantations per 1,000 inhabitants per year in developed countries). The cause of PCCD is unknown but familial cases with right bundle branch block have been reported suggesting that at least some cases are of genetic origin. Reports have linked PCCD to HB1 on 19q13.3, and to mutations in the SCN5A gene (Schott et al., Nature Genet. 23: 20–21 (1999)).

As yet a further example, congenital heart disease occurs at a rate of 8 per 1000 live births, which corresponds to approximately 32,000 infants with newly diagnosed congenital heart disease each year in the United States. Twenty percent of infants with congenital heart disease die within the first year of life. Approximately 80% of the first-year survivors live to reach adulthood. Congenital heart disease also has economic impact due to the estimated 20,000 surgical procedures performed to correct circulatory defects in these patients. The estimated number of adults with congenital heart disease in the United States is currently about 900,000.

In 90% of patients, congenital heart disease is attributable to multifactorial inheritance. Only 5–10% of malformations are due to primary genetic factors, which are either chromosomal or a result of a single mutant gene.

The most common congenital heart disease found in adults is bicuspid aortic valve. This defect occurs in 2% of the general population and accounts for approximately 50% of operated cases of aortic stenosis in adults. Atrial septal defect is responsible for 30–40% of congenital heart disease seen in adults. The most common congenital cardiac defect observed in the pediatric population is ventricular septal defect, which accounts for 15–20% of all congenital lesions. Tetralogy of Fallot is the most common cyanotic congenital anomaly observed in adults. Other congenital heart diseases include Eisenmenger's syndrome, patent ductus arteriosus, pulmonary stenosis, coarctation of the aorta, transposition of the great arteries, tricuspid atresia, univentricular heart, Ebstein's anomaly, and double-outlet right ventricle.

A number of studies have identified putative genetic loci associated with one or more congenital heart diseases.

Congenital heart disease affects more than 40% of all Down syndrome patients. The candidate chromosomal region containing the putative gene or genes for congenital heart disease associated with Down syndrome is 21q22.2-q22.3, between ETS2 and MX1.

DiGeorge syndrome (DGS) is characterized by several symptoms including outflow tract defects of the heart such as teratology of Fallot. Most cases result from a deletion of chromosome 22q11.2 (the DiGeorge syndrome chromosome region, or DGCR). The 22q11 deletion is the second most common cause of congenital heart disease after Down syndrome. Several genes are lost in this deletion including the putative transcription factor TUPLE1. This deletion is associated with a variety of phenotypes, e.g., Shprintzen syndrome; conotruncal anomaly face (or Takao syndrome); and isolated outflow tract defects of the heart including Tetralogy of Fallot, truncus arteriosus, and interrupted aortic arch.

Whereas 90% of cases of DGS may now be attributed to a 22q11 deletion, other associated chromosome defects have been identified. For example, Greenberg et al., Am. J. Hum. Genet. 43:605–611 (1988), reported 1 case of DGS with del10p13 and one with a 18q21.33 deletion. Fukushima et al., Am. J. Hum. Genet. 51 (suppl.):A80 (1992) reported linkage with a deletion of 4q21.3-q25. Gottlieb et al., Am. J. Hum. Genet. 62: 495–498 (1998) concluded that the deletion of more than 1 region on 10p could be associated with the DGS phenotype. The association of the DiGeorge syndrome with at least 2 and possibly more chromosomal locations suggests strongly the involvement of several genes in this disease.

Digilio et al., J. Med. Genet. 34: 188–190 (1997), calculated empiric risk figures for recurrence of isolated Tetralogy of Fallot in families after exclusion of del(22q11), and concluded that gene(s) different from those located on 22q11 must be involved in causing familial aggregation of non-syndromic Tetralogy of Fallot. Johnson et al., Am. J. Med. Genet. (1997) conducted a cytogenetic evaluation of 159 cases of Tetralogy of Fallot. They reported that a del(22q11) was identified in 14% who underwent fluorescence in situ hybridization (FISH) testing with the N25 cosmid probe.

Other congenital heart disease are also suspected to be of polygenic origin. For example, Holmes et al., Birth Defects Orig. Art. Ser. X(4): 228–230 (1974) described familial clustering of hypoplastic left heart syndrome in siblings consistent with multifactorial causation.

Other significant diseases of the heart and vascular system are also believed to have a genetic, typically polygenic, etiological component. These diseases include, for example, hypoplastic left heart syndrome, cardiac valvular dysplasia, Pfeiffer cardiocranial syndrome, oculofaciocardiodental syndrome, Kapur-Toriello syndrome, Sonoda syndrome, Ohdo Blepharophimosis syndrome, heart-hand syndrome, Pierre-Robin syndrome, Hirschsprung disease, Kousseff syndrome, Grange occlusive arterial syndrome, Kearns-Sayre syndrome, Kartagener syndrome, Alagille syndrome, Ritscher-Schinzel syndrome, Ivemark syndrome, Young-Simpson syndrome, hemochromatosis, Holzgreve syndrome, Barth syndrome, Smith-Lemli-Opitz syndrome, glycogen storage disease, Gaucher-like disease, Fabry disease, Lowry-Maclean syndrome, Rett syndrome, Opitz syndrome, Marfan syndrome, Miller-Dieker lissencephaly syndrome, mucopolysaccharidosis, Bruada syndrome, humerospinal dysostosis, Phaver syndrome, McDonough syndrome, Marfanoid hypermobility syndrome, atransferrinemia, Cornelia de Lange syndrome, Leopard syndrome, Diamond-Blackfan anemia, Steinfeld syndrome, progeria, and Williams-Beuren syndrome.

hGDMLP-1 defects will be found to contribute to at least some of the aforementioned disorders.

All patents, patent publications, and other published references mentioned herein are hereby incorporated by reference in their entireties as if each had been individually and specifically incorporated by reference herein. By their citation of various references in this document, applicants do not admit that any particular reference is "prior art" to their invention.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6686188B2). An electronic copy of the "Sequence Listing" will also be available from the USPTO upon request and payment of the fee set forth in 37 CFR 1.19(b)(3).

What is claimed is:

1. An isolated nucleic acid comprising:
a polynucleotide having a sequence selected from the group consisting of (i) the nucleotide sequence of SEQ ID NO:1, (ii) the nucleotide sequence of SEQ ID NO:2, (iii) a nucleotide sequence that is a degenerate variant of the nucleotide sequence of SEQ ID NO:2, (iv) a nucleotide sequence at least 90% identical in sequence to SEQ ID NO:2, (v) a nucleotide sequence that encodes a polypeptide with the amino acid sequence of SEQ ID NO:3, (vi) a nucleotide sequence that encodes a polypeptide at least 90% identical in sequence to SEQ ID NO:3, and (vii) a nucleotide sequence that is the complete complement of the nucleotide sequence of any one of (i)–(vi), wherein said nucleic acid encodes a polypeptide having ATPase activity or a polypeptide capable of binding calmodulin.

2. An isolated nucleic acid comprising:
a polynucleotide having a sequence selected from the group consisting of (i) the nucleotide sequence of SEQ ID NO:1, (ii) the nucleotide sequence of SEQ ID NO:2, (iii) a nucleotide sequence that is a degenerate variant of the nucleotide sequence of SEQ ID NO:2, (iv) a nucleotide sequence at least 95% identical in sequence to SEQ ID NO:2, (v) a nucleotide sequence that encodes a polypeptide with the amino acid sequence of SEQ ID NO:3, (vi) a nucleotide sequence that encodes a polypeptide at least 95% identical in sequence to SEQ ID NO:3, and (vii) a nucleotide sequence that is the complete complement of the nucleotide sequence of any one of (i)–(vi), wherein said nucleic acid encodes a polypeptide having ATPase activity or a polypeptide capable of binding calmodulin.

3. An isolated nucleic acid comprising:
a polynucleotide having a sequence selected from the group consisting of (i) the nucleotide sequence of SEQ ID NO:1, (ii) the nucleotide sequence of SEQ ID NO:2, (iii) a nucleotide sequence that is a degenerate variant of the nucleotide sequence of SEQ ID NO:2, (iv) a nucleotide sequence at least 99% identical in sequence to SEQ ID NO:2, (v) a nucleotide sequence that encodes a polypeptide with the amino acid sequence of SEQ ID NO:3, (vi) a nucleotide sequence that encodes a polypeptide at least 99% identical in sequence to SEQ ID NO:3, and (vii) a nucleotide sequence that is the complete complement of the nucleotide sequence of any one of (i)–(vi), wherein said nucleic acid encodes a polypeptide having ATPase activity or a polypeptide capable of binding calmodulin.

4. The isolated nucleic acid of any one of claims 1–3, wherein said nucleic acid encodes a polypeptide having ATPase activity.

5. The isolated nucleic acid of any one of claims 1–3, wherein said nucleic acid encodes a polypeptide capable of binding calmodulin.

6. The isolated nucleic acid of any one of claims 1–3, wherein said nucleic acid is expressed in skeletal muscle and heart muscle.

7. The isolated nucleic acid of any one of claims 1–3, further comprising at least one expression control element, wherein said polynucleotide is operably linked to said at least one expression control element.

8. The isolated nucleic acid of any one of claims 1–3, attached to a substrate.

9. A microarray wherein at least one probe of said array is a nucleic acid according to any one of claims 1–3.

10. A replicable vector comprising the isolated nucleic acid of any one of claims 1–3.

11. A replicable vector comprising the isolated nucleic acid of claim 7.

12. An expression vector comprising the isolated nucleic acid of any one of claims 1–3.

13. A host cell transformed to contain the nucleic acid of any one of claims 1–3, or the progeny thereof containing said nucleic acid.

14. A host cell transformed to contain the replicable vector of claim 10, or the progeny thereof containing said replicable vector.

15. A host cell transformed to contain the replicable vector of claim 11, or the progeny thereof containing said replicable vector.

16. A host cell transformed to contain the expression vector of claim 12, or the progeny thereof containing said expression vector.

17. A method for producing a polypeptide, the method comprising:
   culturing the host cell of claim 15 under conditions in which the protein encoded by said nucleic acid is expressed.

18. The method of claim 17, further comprising the step of:
   isolating said expressed protein.

19. A method for producing a polypeptide, the method comprising:
   culturing the host cell of claim 16 under conditions in which the protein encoded by said nucleic acid is expressed.

20. The method of claim 19, further comprising the step of:
   isolating said expressed protein.

21. The isolated nucleic acid of claim 4, wherein said nucleic acid is expressed in skeletal muscle and heart muscle.

22. The isolated nucleic acid of claim 5, wherein said nucleic acid is expressed in skeletal muscle and heart muscle.

23. The isolated nucleic acid of claim 4, further comprising at least one expression control element, wherein said polynucleotide is operably linked to said at least one expression control element.

24. The isolated nucleic acid of claim 5, further comprising at least one expression control element, wherein said polynucleotide is operably linked to said at least one expression control element.

25. The isolated nucleic acid of claim 4, attached to a substrate.

26. The isolated nucleic acid of claim 5, attached to a substrate.

27. A microarray wherein at least one probe of said array is a nucleic acid according to claim 4.

28. A microarray wherein at least one probe of said array is a nucleic acid according to claim 5.

29. A replicable vector comprising the isolated nucleic acid of claim 4.

30. A replicable vector comprising the isolated nucleic acid of claim 5.

31. A replicable vector comprising the isolated nucleic acid of claim 23.

32. A replicable vector comprising the isolated nucleic acid of claim 24.

33. An expression vector comprising the isolated nucleic acid of claim 4.

34. An expression vector comprising the isolated nucleic acid of claim 5.

35. A host cell transformed to contain the nucleic acid of claim 4, or the progeny thereof containing said nucleic acid.

36. A host cell transformed to contain the nucleic acid of claim 5, or the progeny thereof containing said nucleic acid.

37. A host cell transformed to contain the replicable vector of claim 29, or the progeny thereof containing said replicable vector.

38. A host cell transformed to contain the replicable vector of claim 30, or the progeny thereof containing said replicable vector.

39. A host cell transformed to contain the replicable vector of claim 31, or the progeny thereof containing said replicable vector.

40. A host cell transformed to contain the replicable vector of claim 32, or the progeny thereof containing said replicable vector.

41. A host cell transformed to contain the expression vector of claim 33, or the progeny thereof containing said expression vector.

42. A host cell transformed to contain the expression vector of claim 34, or the progeny thereof containing said expression vector.

43. A method for producing a polypeptide, the method comprising:
   culturing the host cell of claim 39 under conditions in which the protein encoded by said nucleic acid is expressed.

44. A method for producing a polypeptide, the method comprising:
   culturing the host cell of claim 40 under conditions in which the protein encoded by said nucleic acid is expressed.

45. The method of claim 43, further comprising the step of:
   isolating said expressed protein.

46. The method of claim 44, further comprising the step of:
   isolating said expressed protein.

47. A method for producing a polypeptide, the method comprising:
   culturing the host cell of claim 41 under conditions in which the protein encoded by said nucleic acid is expressed.

48. A method for producing a polypeptide, the method comprising:
   culturing the host cell of claim 42 under conditions in which the protein encoded by said nucleic acid is expressed.

49. The method of claim 47, further comprising the step of:
   isolating said expressed protein.

50. The method of claim 48, further comprising the step of:
   isolating said expressed protein.

* * * * *